US012213996B2

(12) United States Patent
Bernstein et al.

(10) Patent No.: US 12,213,996 B2
(45) Date of Patent: Feb. 4, 2025

(54) METHODS OF TREATING OPTIC NERVE DISEASES USING NEURAL PROGENITOR CELL GROWTH FACTORS

(71) Applicants: University of Maryland, Baltimore, Baltimore, MD (US); REGENERATIVE RESEARCH FOUNDATION, Rensselaer, NY (US); Steven Lance Bernstein, Chevy Chase, MD (US); Candace L. Kerr, Westminster, MD (US); Sally Temple Stern, Slingerlands, NY (US)

(72) Inventors: Steven Lance Bernstein, Chevy Chase, MD (US); Candace L. Kerr, Westminster, MD (US); Sally Temple Stern, Slingerlands, NY (US)

(73) Assignees: UNIVERSITY OF MARYLAND, BALTIMORE, Baltimore, MD (US); REGENERATIVE RESEARCH FOUNDATION, Rensselaer, NY (US)

( * ) Notice: Subject to any disclaimer, the term of this patent is extended or adjusted under 35 U.S.C. 154(b) by 500 days.

(21) Appl. No.: 16/966,204

(22) PCT Filed: Feb. 1, 2019

(86) PCT No.: PCT/US2019/016303
§ 371 (c)(1),
(2) Date: Jul. 30, 2020

(87) PCT Pub. No.: WO2019/152812
PCT Pub. Date: Aug. 8, 2019

(65) Prior Publication Data
US 2022/0175844 A1 Jun. 9, 2022

Related U.S. Application Data

(60) Provisional application No. 62/625,593, filed on Feb. 2, 2018.

(51) Int. Cl.
*A61K 35/30* (2015.01)
*A61K 38/18* (2006.01)
*A61P 27/06* (2006.01)

(52) U.S. Cl.
CPC .............. *A61K 35/30* (2013.01); *A61K 38/18* (2013.01); *A61K 38/1825* (2013.01); *A61K 38/1841* (2013.01); *A61K 38/185* (2013.01); *A61K 38/1866* (2013.01); *A61P 27/06* (2018.01)

(58) Field of Classification Search
CPC ..................................................... A61K 35/30
USPC ........................................ 424/570, 351, 1.45
See application file for complete search history.

(56) References Cited

U.S. PATENT DOCUMENTS 9,107,897 B2 * 8/2015 Klassen .................. A61K 35/30
2011/0052678 A1 * 3/2011 Shantha ............. A61K 31/4706
424/94.4

FOREIGN PATENT DOCUMENTS

WO 2016/032263 3/2016
WO 2016/037159 3/2016

OTHER PUBLICATIONS

Bernstein et al., "The optic nerve lamina is a neural progenitor cell niche". Investigative Ophthalmology & Visual Science. Apr. 2014, vol. 55, 1385 (Year: 2014).*
Guo et al., "Age-related Gene Expression Changes in the Murine Optic Nerve Lamina". Investigative Ophthalmology & Visual Science. Apr. 2014, vol. 55, 1376 (Year: 2014).*
Guo et al., "Characterizing Sox2 cell in the adult mouse optic nerve lamina". Investigative Ophthalmology & Visual Science. Jun. 2015, vol. 56, 3576 (Year: 2015).*
International Search Report and Written Opinion of the International Searching Authority, issued Apr. 15, 2019 in corresponding International Patent Application No. PCT/US2019/016303.
Bernstein et al., "The optic nerve lamina is a neural progenitor cell niche", ARVO Annual Meeting Abstract, Investigative Ophthalmology & Visual Science, Apr. 2014, vol. 55, 1385, XP055572323.
Guo et al., "Age-related Gene Expression Changes in the Murine Optic Nerve Lamina", ARVO Annual Meeting Abstract, Investigative Ophthalmology & Visual Science, Apr. 2014, vol. 55, 1376, XP055572483.
Fawcett et al., "Cultivation of mouse neural progenitor cells from the optic nerve", ARVO Annual Meeting Abstract, Investigative Ophthalmology & Visual Science, Jun. 2017, vol. 58, 3328, XP055572545.
Bernstein et al., "Directional Growth of Optic Nerve Axons and Processive Gliogenesis", Microscopy and Microanalysis, 24(S1): 1276-1277 (2018).
Gokuladhas et al., "Ocular progenitor cells and current application in regenerative medicines—Review", Genes & Diseases, 4(2): 88-99 (2017).
Ma et al., "Transplantation of Human Neural Progenitor Cells Expressing IGF-1 Enhances Retinal Ganglion Cell Survival", PLOS One, 10(4): e0125695, XP009512064 (2015).
Johnson et al., "Transplantation prospects for the inner retina", Eye, 23(10): 1980-1984 (2008).

* cited by examiner

*Primary Examiner* — Allison M Fox
*Assistant Examiner* — Hanan Isam Abuzeineh
(74) *Attorney, Agent, or Firm* — Wenderoth, Lind & Ponack, L.L.P.

(57) ABSTRACT

Optic nerve lamina region neural progenitor cells (ONLR-NPCs) are provided. Such cells secrete growth factors and survival factors that can be used in the treatment of optic nerve diseases, such as glaucoma. Also provided are methods of treating or preventing optic nerve diseases, such as glaucoma, using one or more factors secreted by ONLR-NPCs, combinations of factors secreted by ONLR-NPCs, or culture media conditioned by ONLR-NPCs.

17 Claims, 24 Drawing Sheets
(22 of 24 Drawing Sheet(s) Filed in Color)
Specification includes a Sequence Listing.

A

B

C

D

E

F

G

H

I

J

K

L

E

F

G

H

I

J

K

L

M

N

O

E

F

G

H ered by increased intraocular pressure over time. Glaucoma is a progressive disease which can lead to permanent vision loss within a few years in the absence of treatment. There are two types of glaucoma, open-angle glaucoma and angle-closure glaucoma. The majority of cases in the United States and Western Europe are the former type, while the latter is most common in China and other Asian countries. Both types of glaucoma result from improper drainage of aqueous humor from the eye (Weinreb et al., 2016). While angle-closure glaucoma results from improper drainage of aqueous humor from the eye (Weinreb et al., 2016) the causes of open-angle glaucoma are now known to be more complex than simple increase in intraocular pressure (Levin, 2005).

METHODS OF TREATING OPTIC NERVE DISEASES USING NEURAL PROGENITOR CELL GROWTH FACTORS

STATEMENT OF FEDERALLY SPONSORED RESEARCH AND DEVELOPMENT

This invention was made with government support under Grant Number EY015304 awarded by the National Institutes of Health. The government has certain rights in the invention.

SEQUENCE LISTING

A sequence listing in electronic (ASCII text file) format is filed with this application and incorporated herein by reference. The name of the ASCII text file is "2020_2122A_ST25.txt"; the file was created on Dec. 2, 2020; the size of the file is 7 KB.

BACKGROUND

The primary cause of blindness in humans is glaucoma, an optic neuropathy characterized by progressive degeneration of the optic nerve due to increased intraocular pressure over time. Glaucoma is a progressive disease which can lead to permanent vision loss within a few years in the absence of treatment. There are two types of glaucoma, open-angle glaucoma and angle-closure glaucoma. The majority of cases in the United States and Western Europe are the former type, while the latter is most common in China and other Asian countries. Both types of glaucoma result from improper drainage of aqueous humor from the eye (Weinreb et al., 2016). While angle-closure glaucoma results from improper drainage of aqueous humor from the eye (Weinreb et al., 2016) the causes of open-angle glaucoma are now known to be more complex than simple increase in intraocular pressure (Levin, 2005).

The pathophysiology of glaucoma is not well understood, but intraocular pressure is thought to contribute to damage to the optic nerve head with a corresponding loss of retinal ganglion cells. Other causes of damage in open-angle glaucoma include loss of neurotrophic factors and changes in underlying supporting cells such as glia (Almasieh et al., 2012). Current treatments for glaucoma focus only on intraocular pressure reduction and this approach is only partly successful. Alternative and/or supplemental treatments for glaucoma and related optic nerve diseases are needed. The present disclosure is directed to such needs and other important goals.

BRIEF SUMMARY

The optic nerve (ON) is a paired nerve that transmits visual information from the retina of each eye to the brain. The ON is composed of retinal ganglion cell axons and glial cells, with around one million axons of retinal ganglion cells present in the retina of each human eye. Axons passing through the ON that extend from the eye to brain are myelinated in the anterior ON below the optic nerve lamina region (ONLR).

The ONLR is a complex, specialized, unmyelinated boundary tissue present in primates and most mammals that contains a vascular plexus with retinal, choroidal and optic nerve contributions. The ONLR is located at the junction of the optic nerve and the eye, partially embedded in the eye wall (FIGS. 1A & 1B), and it can be further characterized as the region in which unmyelinated retinal ganglion cell axons are myelinated as they combine to form the optic nerve (ON). Animals without an ONLR, such as rabbits, have myelinated retinas suggesting that the ONLR acts as a barrier to the myelination process.

The multiple functions of the ONLR include blocking intraocular myelination, enabling myelination of the growing axons in postnatal individuals, and modulating fluid pressure differences between eye and brain. The ONLR is also hypothesized to be the presumptive primary lesion in age-related open-angle glaucoma (OAG). The precise mechanisms enabling the ONLR to perform all of these widely disparate functions are unknown.

As reported herein, it has been discovered that a mitotically active, age-depletable neural progenitor cell (NPC) population is present in the ONLR of humans and rodents. ONLR-NPCs have a unique genetic signature and they produce growth and survival factors that play a key role in maintaining ocular health and function. It appears that ONLR-NPCs are lost during aging, in glaucoma, and in other optic nerve diseases. Loss of the ONLR-NPCs and therefore loss of the growth and survival factors secreted from these cells likely contributes to optic nerve diseases that become increasingly severe over time. Replacement of these secreted factors in the eye, either alone or in combination with other treatments (e.g., those that reduce ocular pressure), may serve to improve the treatment of glaucoma and other optic nerve diseases.

Using reporter mice with conditional gene expression or inducible selective knockouts, it is shown herein that ONLR-NPCs can generate all macroglial cell forms in the anterior ON. Using a green fluorescent protein reporter, it is shown herein that ONLR-NPCs provide the myelinating oligodendrocytes as growing axons emerge from the eye. The ONLR acts as a gliogenic processing center, ultimately supplying the growing ON with glial cells as growing unmyelinated axons emerge from the eye. Early ONLR-NPC loss results in ON hypoplasia, regional axonal dysfunction and hypomyelination. In mature animals, ONLR-NPCs may also enable glial replacement and remyelination. Age-related ONLR-NPC depletion may help explain why focal ON diseases such as primary open-angle glaucoma progress in severity during aging.

ONLR-NPCs, as defined herein, form the basis of the present invention. The invention thus includes, but is not limited to, ONLR-NPCs, cultures of ONLR-NPCs, ONLR-NPC conditioned media, ONLR-NPC lysates, ONLR-NPC extracts, and compositions comprising one or more of the noted cells, cultures, media, lysates and extracts.

The invention also includes methods of treating or preventing optic nerve diseases, such as glaucoma, using one or more of ONLR-NPCs, cultures of ONLR-NPCs, ONLR-NPC lysates, ONLR-NPC extracts, and compositions comprising one or more of the noted cells, cultures, lysates and extracts.

ONLR-NPCs secrete particular factors, such as growth factors and survival factors, and the invention is directed to the use of these secreted factors as well. The invention thus includes methods of treating or preventing optic nerve diseases, such as glaucoma, using one or more factors secreted by ONLR-NPCs, combinations of factors secreted by ONLR-NPCs, or culture media conditioned by ONLR-NPCs. The factors secreted by ONLR-NPCs include, but are not limited to, growth factors and survival factors.

In particular, and in a first embodiment, the invention is directed to optic nerve lamina region neural progenitor cells (ONLR-NPCs). The ONLR-NPCs of this and the other embodiments and aspects of the invention are characterized, for example, as nestin(+), SOX2(+), GFAP(+), NG2(−) cells. The invention includes single ONLR-NPCs as well as populations of ONLR-NPCs. In one aspect, the invention is directed to an in vitro cell culture comprising one or more ONLR-NPCs. In another aspect, the invention is directed to an in vitro cell culture consisting of one or more ONLR-NPCs.

In a second embodiment, the invention is directed to ONLR-NPC conditioned media, obtained from a culture of ONLR-NPCs, such as an in vitro cell culture of ONLR-NPCs. The ONLR-NPC conditioned media may be prepared by growing the ONLR-NPCs for several days in a defined tissue culture medium containing Fibroblast Growth Factors-2 and -4. The ONLR-NPC conditioned media may be collected by decanting the sterile medium, followed by concentration and dialysis or gel filtration to eliminate both uninvolved medium, ions and large molecular weight compounds such as bovine serum albumen.

In a third embodiment, the invention is directed to an ONLR-NPC lysate. ONLR-NPC lysates comprise the material collected from ONLR-NPCs that are broken apart by mechanical, chemical means or physical means. ONLR-NPC lysates may be prepared by collecting the ONLR-NPCs grown in appropriate medium by centrifugation and washing these cells, followed by lysis via mechanical, chemical means or physical means.

In a fourth embodiment, the invention is directed to an ONLR-NPC extract. ONLR-NPC extracts comprise some or all of the growth factors generated and/or secreted by the ONLR-NPCs. The ONLR-NPC extracts may be a collection of growth factors isolated from cells, or a collection of selected growth factors known to be produced by ONLR-NPCs but produce by means other than the ONLR-NPCs and combined to form an "artificial" ONLR-NPC extract. ONLR-NPC extracts may thus be prepared by direct isolation of growth factors from the ONLR-NPCs via lysis and recovery or via collection from the conditioned medium, as well as by combining selected individual growth factors into an "artificial" ONLR-NPC extract.

In a fifth embodiment, the invention is directed to methods of treating or preventing an optic nerve disease. In one aspect the method comprises administering to a subject in need thereof a therapeutically effective amount of a composition comprising one or more of:
(i) a population of ONLR-NPCs,
(ii) ONLR-NPC conditioned media,
(iii) an ONLR-NPC lysate,
(iv) an ONLR-NPC extract, and
(v) one or more factors secreted by ONLR-NPCs, thereby treating or preventing an optic nerve disease in the subject.

In one aspect, the optic nerve disease is open-angle glaucoma. In another aspect, the optic nerve disease is angle-closure glaucoma. In a further aspect, the optic nerve disease is optic nerve hypoplasia, optic nerve hypomyelination, regional axonal dysfunction, nonarteritic anterior ischemic optic neuropathy (NAION), or optic neuritis. In one aspect, the administering is administration to the eye of the subject via means that include, but are not limited to, topical application (e.g. eye drops), subconjunctival injection, intravitreal injection, and retrobulbar injection.

As indicated above, the ONLR-NPCs of each embodiment and aspect of the invention are characterized based on the expression or lack of expression of certain markers by the cells. For example, in some aspects and embodiments, the ONLR-NPCs are characterized as nestin(+), SOX2(+), GFAP(+), NG2(−) cells. In a related aspect, the ONLR-NPCs are characterized as nestin(+), SOX2(+), GFAP(+), NG2(−), SOX1(+), vimentin(+), BDNF(+) cells. In some aspects, the ONLR-NPCs are further characterized based on their ability to secrete one or more growth factors. These growth factors include Latent Transforming Growth Factor-Beta 1 (TGF-β1), Connective Tissue Growth Factor (CTGF), Nerve Growth Factor (NGF), Fibroblast Growth Factor (FGF-1), Vascular Endothelial Growth Factor (VEGF), Mesenchymal Astrocyte Neurotrophic Factor (MANF) and Insulin-like Growth Factors-1 and -2 (IGF-1 and IGF-2). In a related aspect, the ONLR-NPCs secrete at least five of the growth factors listed in Table 1 (i.e., VGF, TGFB1, LTBP1, LTBP2, PDGFB, CTGF, FGF11, NDNF, PDGFC, TGFβ2, NGF, FGF1, Midkine, VEGFA, MANF, IGF-1, and IGF-2). Alternatively or in addition, the ONLR-NPCs express at least five of the additional proteins listed in Table 2. In a further related aspect, the ONLR-NPCs secrete each of the growth factors listed in Table 1, or express each of the proteins listed in Table 2, or each of the growth factors and proteins listed in Tables 1 and 2.

In one aspect, the composition comprises one or more factors secreted by ONLR-NPCs, wherein the factors are selected from the group consisting of Nerve Growth Factor (NGF), Latent Transforming Growth Factor-Beta 1 (TGF-β1), Fibroblast Growth Factor 1 (FGF1), Vascular Endothelial Growth Factor (VEGF), Mesenchymal Astrocyte Neurotrophic Factor (MANF), Connective Tissue Growth Factor (CTGF), and Insulin-like Growth Factors-1 and -2 (IGF-1 and IGF-2). In a related aspect, the composition comprises each of these factors. In a further related aspect, the composition comprises one or more factors secreted by ONLR-NPCs, wherein the factors are selected from the group set forth in Table 1. In a related aspect, the composition comprises each of these factors.

The foregoing has outlined rather broadly the features and technical advantages of the present invention in order that the detailed description of the invention that follows may be better understood. Additional features and advantages of the invention will be described herein, which form the subject of the claims of the invention. It should be appreciated by those skilled in the art that any conception and specific embodiment disclosed herein may be readily utilized as a basis for modifying or designing other structures for carrying out the same purposes of the present invention. It should also be realized by those skilled in the art that such equivalent constructions do not depart from the spirit and scope of the invention as set forth in the appended claims. The novel features which are believed to be characteristic of the invention, both as to its organization and method of operation, together with further objects and advantages will be better understood from the following description when considered in connection with the accompanying figures. It is to be expressly understood, however, that any description, figure, example, etc. is provided for the purpose of illustration and description only and is by no means intended to define the limits the invention.

BRIEF DESCRIPTION OF DRAWINGS

The patent or application file contains at least one drawing executed in color. Copies of this patent or patent application publication with color drawing(s) will be provided by the Office upon request and payment of the necessary fee.

FIG. 1E, 1G, 1J: 50 um.

FIG. 3B and ONLR; FIG. 3C), or 30d (53d postnatal; FIG. 3D). B. Hippocampal GFP expression 14d post-induction. GFP(+) cells are present on td-Tomato background. C. ONLR-SOX2-driven GFP expression 14d post-induction. GFP expression is low, and limited to the ONLR. D. ONLR SOX2-driven GFP expression 30d post-induction. Inset: GFP is present in short processes parallel to the long axis of the ON, corresponding to myelin segments (arrowheads). E. SOX2-GFP expression is clustered in ONLR-nestin(+) cells (arrows). GFP expression is present in ONLR and in the anterior ON. inset: GFP expression in myelin-containing structures in the ON parallel to the axis. F. 30 um Z-stack ONLR cross-section in a SOX2-GFP animal 30d post-induction. ONLR-GFP expression is concentrated in large cells with a stellate morphology. Scale bar in G: 50 um; all other photos: 100 um.

DETAILED DESCRIPTION

1. Definitions

Figure 1:
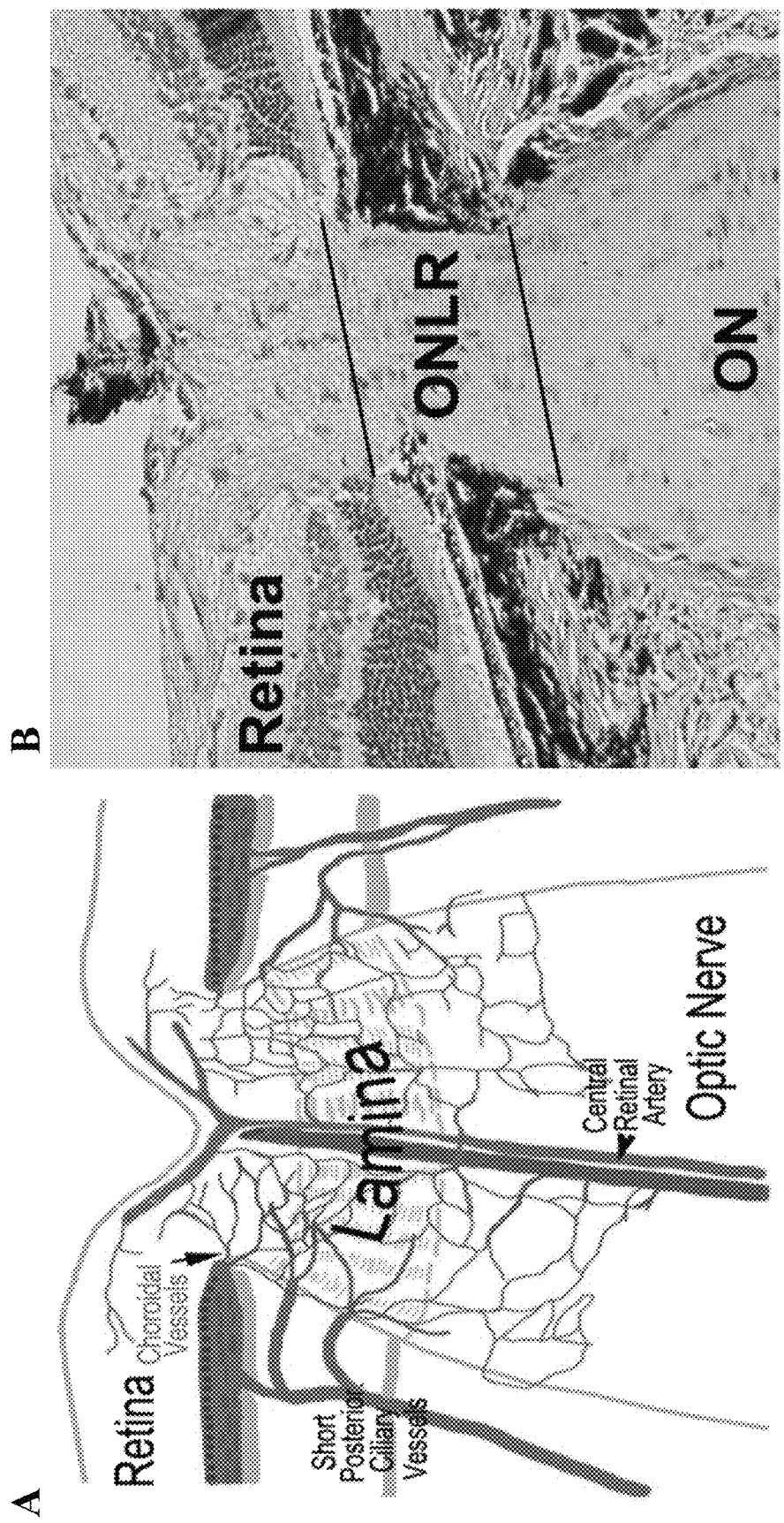
FIG. 1. ONLR Characterization in vivo. A. Schematic of human ONLR vascularization. The ONLR receives inputs from choroid, ON pial vessels, and retinal vessels in the vicinity of the nerve. B. H & E longitudinal section of the mouse ONLR. Retinal neurons define the outer border of the ONLR. C. Two-photon micrograph of fluorescein-filled rodent ONLR vessels. ONLR vasculature is more complex than the overlying retina or ON. Total capillary area quantification of the three areas is shown in the inset. Retina (R) and ONLR (L) have equivalent capillary areas, compared with distal optic nerve (N). Graph constructed from data in (Balaratnasingam et al., 2014) D. Nestin (red)/myelin ($O_4$ antibody; green) localization define the ONLR. Nestin expression is seen as a gradient that declines anterograde, while myelination below the ONLR reveals a counter gradient. E. AQP4 (in green)/nestin (in red) confocal colocalization shows reduced ONLR-AQP4, compared with retina or distal ON. F. ONLR-nestin/GFAP co-localization in the ONLR. Red: Nestin. Green: GFAP. Scale bar: 20 um. G. SOX2(+) nuclei are qualitatively increased in the nestin-enriched ONLR (arrowheads), and SOX2(+) nuclei are present in reduced numbers in the distal ON (FIG. 1G inset: ON). H. Quantification of SOX2(+) nuclei in ONLR and ON. The ONLR is enriched in SOX2 nuclei, in terms of both area (left bars), and SOX2-nuclear ratio (right bars). I. Ki67-mitotic immunoanalysis in the ONLR and ON. There is a qualitative increase in the number of mitotic cells in the 60d mouse ONLR (arrows), compared with the ON. Inset: Ki67(+) nuclei quantification in 60d ONLR and ON. ONLR possesses more mitoses, and more mitoses per unit area, than in distal ON. J. ONLR SOX2/GFAP localization. GFAP expression is stronger in ONLR than the ON, and GFAP cytoplasmic signal is present in cells surrounding SOX2(+) nuclei, suggesting that the ONLR SOX2(+) cells express both proteins. Distal ON (inset) reveals that cells with SOX2(+) nuclei lack GFAP expression. K. NG2 expression is present in the anterior ON adjacent to the ONLR, while the ONLR is deficient in NG2 expression (lines delineate the NG2 band). NG2 expression is also diffusely present throughout the distal ON. Inset: Unmyelinated ONLR defined with nestin (in red) and ON by myelin ($O_4$: in green) L. Higher magnification reveals that NG2(+) cells in the ON have extended cytoplasmic fibrils (arrows), consistent with OPCs. Scale bars in FIG. 1C, 1F, 1L: 20 um.
Figure 1:
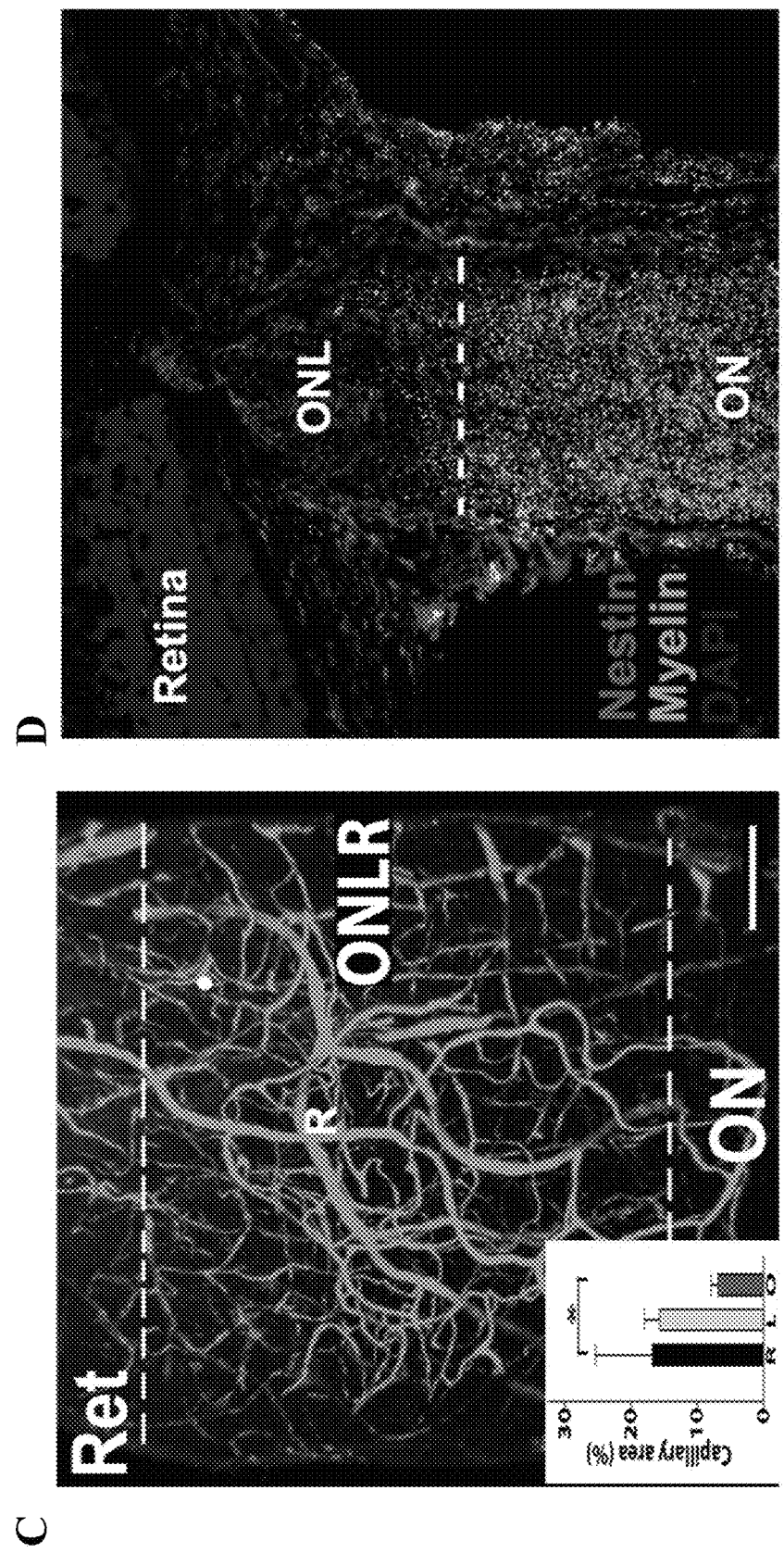
Figure 1:
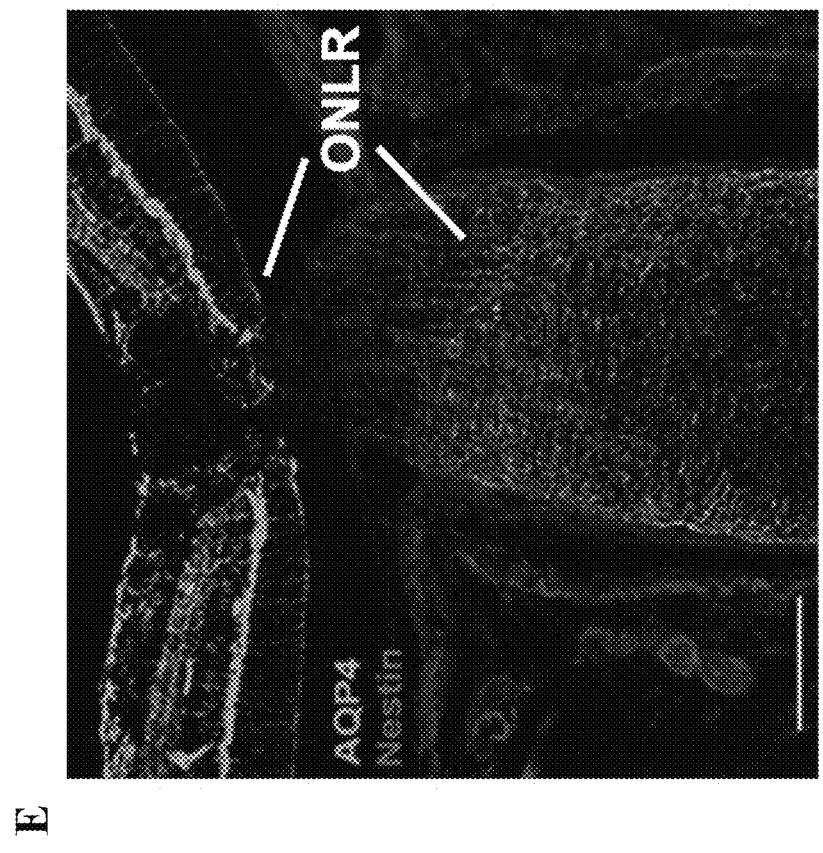
Figure 1:
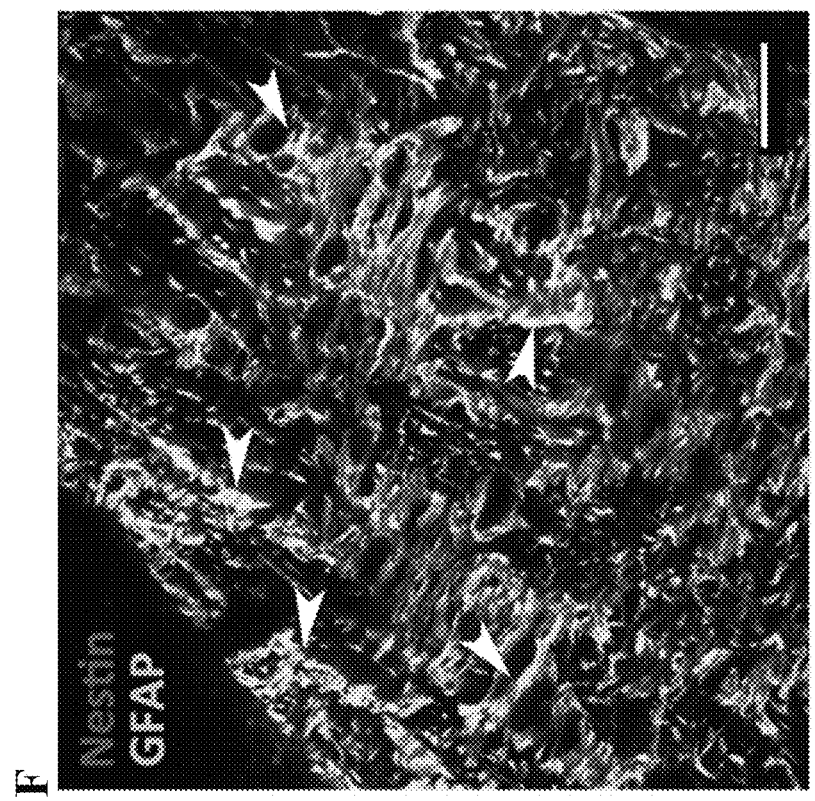
Figure 1:
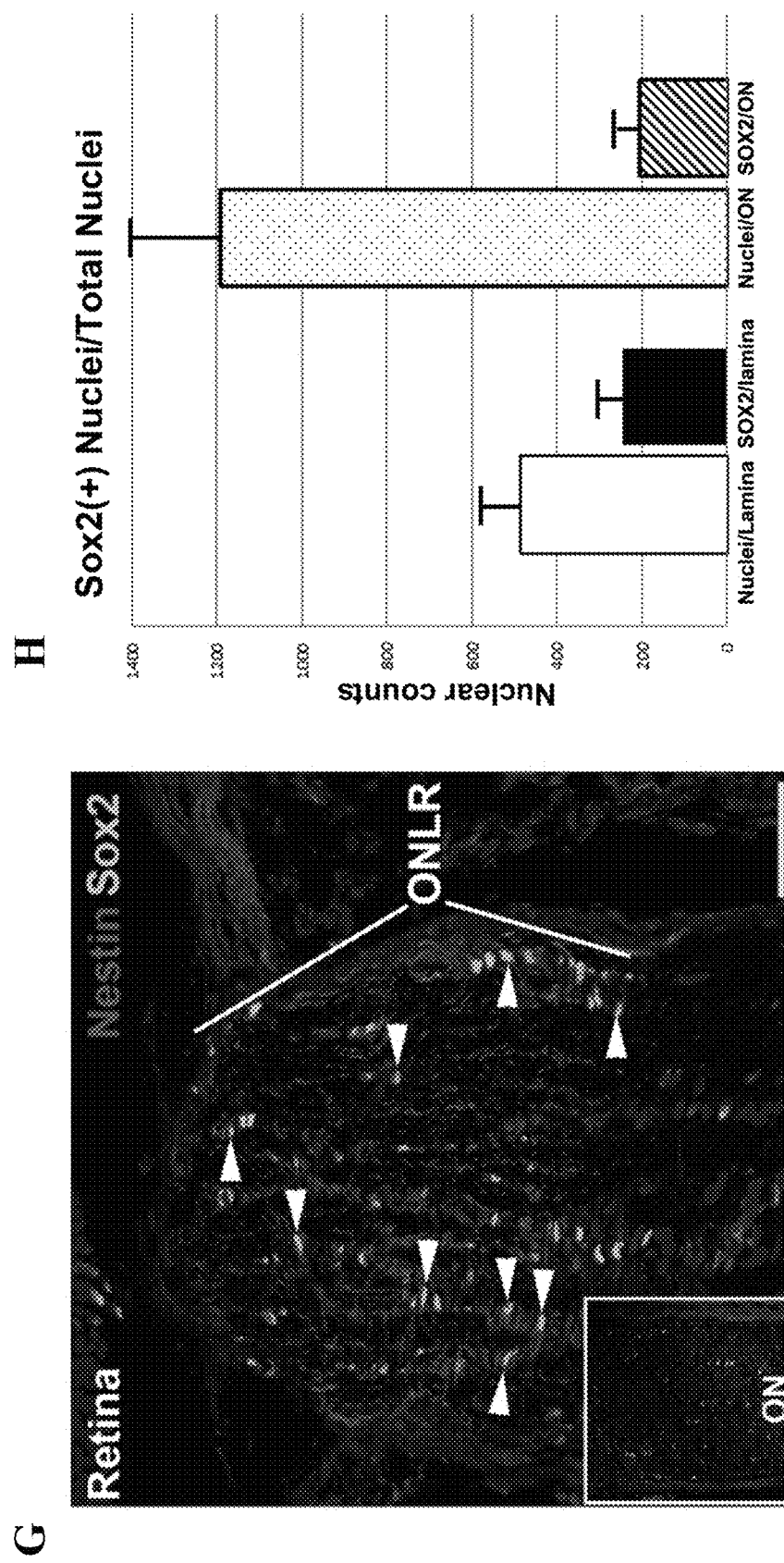
Figure 1:
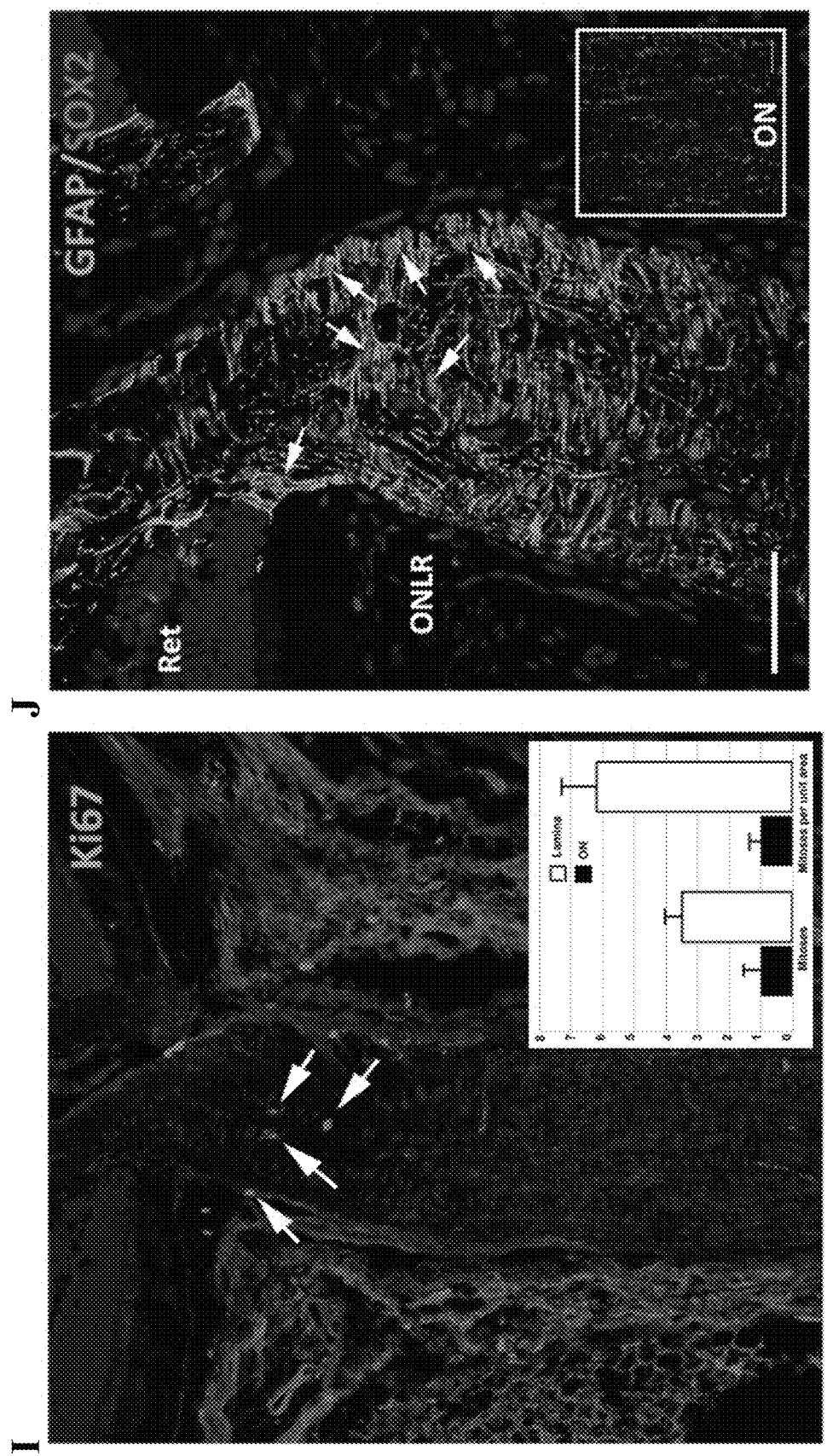
Figure 1:
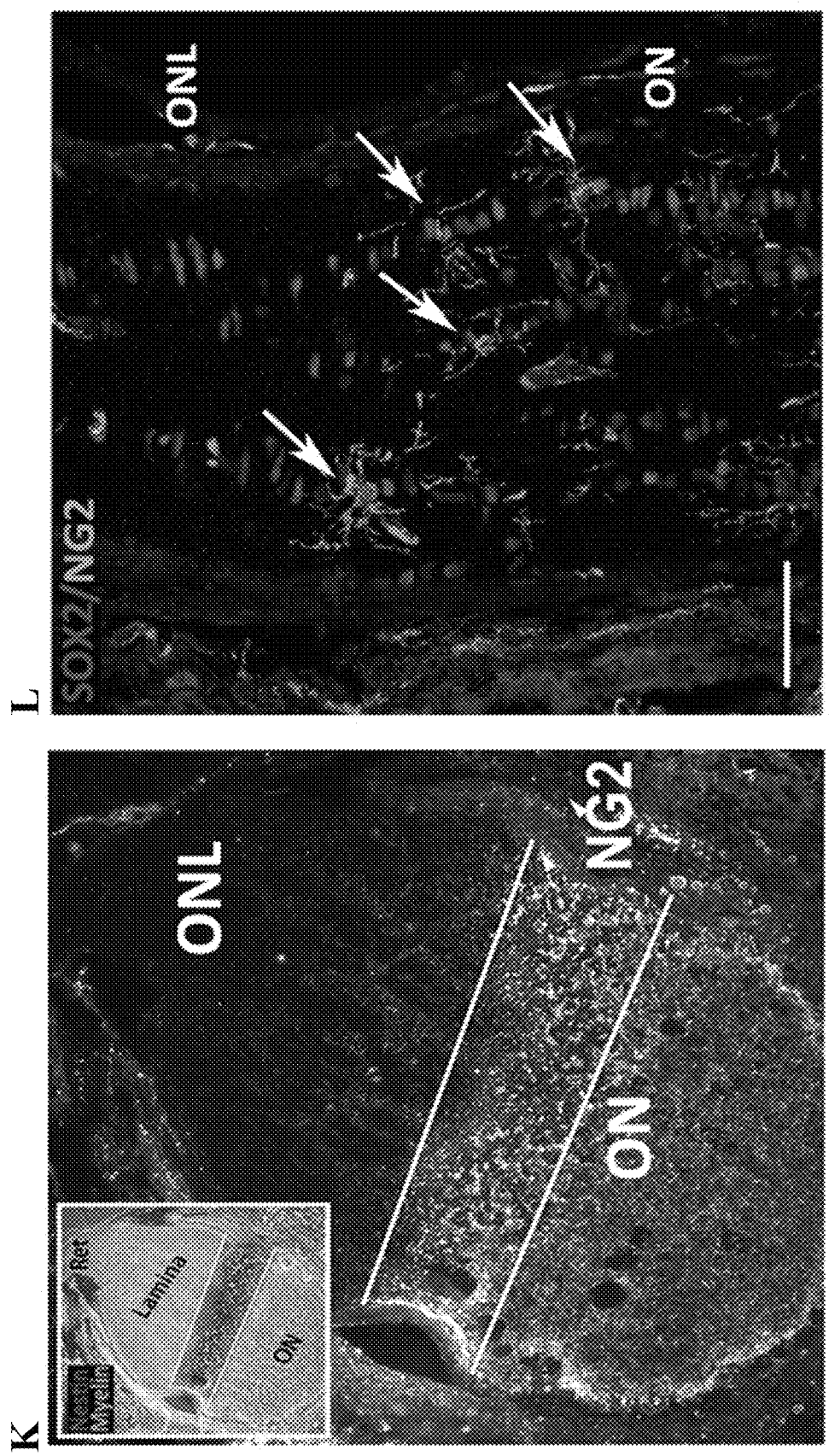

Unless otherwise noted, technical terms are used according to conventional usage. Definitions of common terms in molecular biology may be found, for example, in Benjamin Lewin, Genes XII, published by Jones & Bartlett Learning, 2014 (ISBN 1449659853); Kendrew et al. (eds.); The Encyclopedia of Molecular Biology, published by Blackwell Publishers, 1994 (ISBN 0632021829); and Robert A. Meyers (ed.), Molecular Biology and Biotechnology: a Comprehensive Desk Reference, published by Wiley, John & Sons, Inc., 1995 (ISBN 0471186341); and other similar technical references.

As used herein, "a" or "an" may mean one or more. As used herein when used in conjunction with the word "comprising," the words "a" or "an" may mean one or more than one. As used herein "another" may mean at least a second or more. Furthermore, unless otherwise required by context, singular terms include pluralities and plural terms include the singular.

As used herein, "about" refers to a numeric value, including, for example, whole numbers, fractions, and percentages, whether or not explicitly indicated. The term "about" generally refers to a range of numerical values (e.g., +/−5-10% of the recited value) that one of ordinary skill in the art would consider equivalent to the recited value (e.g., having the same function or result). In some instances, the term "about" may include numerical values that are rounded to the nearest significant figure.

II. The Present Invention

A mitotically active, age-depletable population of neural progenitor cells (NPC) has been discovered in the optic nerve lamina region (ONLR) of the eyes of humans and rodents. As further described herein, these ONLR-NPCs have a unique genetic signature and they produce growth and survival factors thought to play a key role in maintaining ocular health and function.

Because ONLR-NPCs are lost during aging, in glaucoma, and in other optic nerve diseases, loss of ONLR-NPCs and the growth and survival factors they produce are thought to contribute to optic nerve diseases. Replacement of these secreted factors in the eye, either alone or in combination with other treatments (e.g., those that reduce ocular pressure), may serve to improve the treatment of glaucoma and other optic nerve diseases.

As described herein, this population of ONLR-NPCs possess properties typically found in NPCs. For example, ONLR-NPCs co-express SOX1 and SOX2, as well as a number of NPC-specific proteins including nestin, Glial Fibrillary Acidic Protein (GFAP) and vimentin. ONLR-NPCs also express NPC-associated growth factors such as brain derived neurotrophic factor (BDNF). Thus, the postnatal ONLR-NPC niche is capable of generating both types of glial cells in the ON, and enabling normal postnatal ON growth, myelination, fluid regulation and cellular replacement. ONLR-NPCs do not express Neural/Glial Antigen 2 (NG2).

Optic Nerve Lamina Region Neural Progenitor Cells (ONLR-NPCs)

The present invention is directed, in part, to optic nerve lamina region neural progenitor cells (ONLR-NPCs) as defined herein. ONLR-NPCs of the invention are characterized as cells located in the ONLR of humans and rodents.

The ONLR-NPCs of the present invention can be defined based on the expression, or lack thereof, of selected marker proteins. The ONLR-NPCs of the present invention can thus be defined as nestin(+), SOX2(+), GFAP(+), NG2(−) neural cells. SOX2 is the transcription factor SRY (sex determining region Y)-box 2. GFAP is glial fibrillary acidic protein. NG2 is neuron-glial antigen 2. In some aspects of the invention, ONLR-NPCs also express one or more of SOX1, vimentin, and BDNF. Thus, in certain aspects of the invention, the ONLR-NPCs are:

nestin(+), SOX2(+), GFAP(+), NG2(−), SOX1(+); or
nestin(+), SOX2(+), GFAP(+), NG2(−), vimentin(+); or
nestin(+), SOX2(+), GFAP(+), NG2(−), BDNF(+); or
nestin(+), SOX2(+), GFAP(+), NG2(−), SOX1(+), vimentin(+); or
nestin(+), SOX2(+), GFAP(+), NG2(−), SOX1(+), BDNF(+); or
nestin(+), SOX2(+), GFAP(+), NG2(−), vimentin(+), BDNF(+); or
nestin(+), SOX2(+), GFAP(+), NG2(−), SOX1(+), vimentin(+), BDNF(+).

In each aspect of the invention, the cells are positionally defined as residing within the ONLR, but exhibiting nestin (+)/SOX2(+)/NG2(−) characteristics, unlike the cells in the rest of the eye and optic nerve.

Alternatively, or in addition, the ONLR-NPCs of the invention can be defined based on expression of one or more of the secreted factors provided in Table 1. In one aspect of the invention, the ONLR-NPCs of the present invention can be defined as neural cells that secrete one or more of Latent Transforming Growth Factor-Beta 1 (TGF-β1), Connective Tissue Growth Factor (CTGF), Nerve Growth Factor (NGF), Fibroblast Growth Factor (FGF-1), Vascular Endothelial Growth Factor-A (VEGFA), Mesenchymal Astrocyte-derived Neurotrophic Factor (MANF) and Insulin-like Growth Factors-1 and -2 (IGF-1 and IGF-2). In a related aspect, the ONLR-NPCs secrete each of Latent Transforming Growth Factor-beta 1 (TGF-β1), Connective Tissue Growth Factor (CTGF), Nerve Growth Factor (NGF), Fibroblast Growth Factor (FGF-1), Vascular Endothelial Growth Factor-A (VEGFA), Mesenchymal Astrocyte-derived Neurotrophic Factor (MANF) and Insulin-like Growth Factors-1 and -2 (IGF-1 and IGF-2).

The ONLR-NPCs of the present invention can also be defined as neural cells that secrete at least 5, 6, 7, 8, 9, 10, 11, 12, 13, 14, 15, 16 or each of the growth factors provided in Table 1. In one aspect, the ONLR-NPCs secrete each of the growth factors provided in Table 1. In one aspect of the invention, the ONLR-NPCs of the present invention are nestin(+), SOX2(+), GFAP(+), NG2(−) neural cells that secrete at least 5, 6, 7, 8, 9, 10, 11, 12, 13, 14, 15, 16 or each of the growth factors provided in Table 1.

TABLE 1

Secreted factors produced by ONLR-NPCs

VGF Nerve Growth Factor inducible (VGF)
Transforming Growth Factor, beta-1, 68 kDa (TGFβ1)
Latent Transforming Growth Factor Binding Protein Beta 1 (LTBP1)
Latent Transforming Growth Factor Binding Protein Beta 2 (LTBP2)
Platelet-derived Growth Factor beta polypeptide (PDGFB)
Connective Tissue Growth Factor (CTGF)
Fibroblast Growth Factor 11 (FGF11)
Neuron-derived Neurotrophic Factor (NDNF)
Platelet-derived Growth Factor C (PDGFC)
Transforming Growth Factor, beta 2 (TGFβ2)
Nerve Growth Factor (NGF)
Fibroblast Growth Factor 1 (FGF1)
Midkine (Neurite Growth-promoting Factor 2)
Vascular Endothelial Growth Factor A (VEGFA)
Mesencephalic Astrocyte-derived Neurotrophic Factor (MANF)
Insulin-like Growth Factors-1 and-2 (IGF-1 and IGF-2)

The ONLR-NPCs of the invention may be further characterized as positionally isolated and residing within the ONLR (see FIGS. 3D and 3E), but exhibiting nestin(+)/SOX2(+)/NG2(−) characteristics, unlike the cells in the rest of the eye and optic nerve. ONLR-NPCs of the invention may be additionally characterized as exhibiting an extended 'starlike' morphology in living animals (see FIGS. 3F and 3G).

The ONLR-NPCs of the invention may also be characterized based on their ability to express at least 5, 6, 7, 8, 9, 10, 11, 12, 13, 14, 15 or each of the proteins listed in Table 2.

TABLE 2

Additional proteins produced by ONLR-NPCs

Cell Growth Regulator with Ring Finger Domain 1
Dynein Regulatory Complex Subunit 4
Fibroblast Growth Factor 12
Fibroblast Growth Factor 14
Fibroblast Growth Factor Receptor 4
Growth Arrest and DNA Damage-inducible Protein GADD45 beta
Growth Factor Independent 1 Transcriptional Repressor
Growth Hormone Receptor
Placental Growth Factor
Platelet-derived Growth Factor D/Spinal Cord-Derived Growth Factor B
Platelet-derived Growth Factor Receptor-like Protein
Transforming Growth Factor beta-1 Proprotein
Transforming Growth Factor beta-1-induced Transcript 1 Protein
Upper Zone of Growth Plate and Cartilage Matrix Associated Protein
Vascular Endothelial Growth Factor C
UNC-13 Homolog C The present invention includes single ONLR-NPCs, populations of ONLR-NPCs comprising two or more cells, and cultures of ONLR-NPCs, i.e., in vitro cell cultures comprising ONLR-NPCs and in vitro cell cultures consisting ONLR-NPCs.

ONLR-NPC Conditioned Media

The invention is also directed to ONLR-NPC conditioned media. Such media is cell culture media in which ONLR-NPCs have been grown, such as an in vitro cell culture of ONLR-NPCs. Because ONLR-NPCs secrete factors, such as growth factors and survival factors, the media in which the cells are grown becomes conditioned by the presence of the secreted factors.

As used herein, ONLR-NPC conditioned media is any cell culture media in which ONLR-NPCs have been present for at least 5 minutes. In some aspects, ONLR-NPC conditioned media is cell culture media in which ONLR-NPCs have been present for at least 15, 30, 45, 60, 75, 90, 105 or 120 minutes, or 2.5, 3, 3.5, 4, 4.5, 5, 5.5, 6, 6.5, 7, 7.5, 8, 8.5, 9, 9.5, 10, 10.5, 11, 11.5, 12, 13, 14, 15, 16, 17, 18, 19, 20, 21, 22, 23, or 24 hours, or 1.5, 2, 2.5, 3, 3.5, 4, 4.5, 5, 5.5, 6, 6.5, 7, 7.5, 8, 8.5, 9, 9.5, 10, 10.5, 11, 11.5 or 12 days, or more.

ONLR-NPCs are typically grown in Neurobasal™ (ThermoFisher Scientific) medium supplemented with FGF-2 and -4, and B27 supplementation, and grown on enhanced extracellular matrix (matrigel) at concentrations typically exceeding 10% media. However, the skilled artisan will understand that variations in the identity and amounts of the components in such media can be made without altering the health or growth the ONLR-NPCs, or the factors secreted by the cells into the media. It should therefore be understood that the identity of the media in which the cells are cultured is not critical and that it can vary. In a preferred aspect, the media does not include any animal sourced materials (ASM) and is thus ASM-free.

ONLR-NPCs are typically grown under conditions of enriched $CO_2$ (5%), oxygen concentrations ranging from 5-21%, and 95% relative humidity.

ONLR-NPC conditioned media may be collected from cultures of ONLR-NPC through techniques well known in the art, such as simply decanting the media into a separate vessel. ONLR-NPC conditioned media may be stored, such as at 4° C. or frozen, or used immediately. ONLR-NPC conditioned media may be processed to concentrate the media and/or to remove the secreted factors from the media. Suitable processes include concentrating the decanted media, following by dialysis and/or gel filtration to eliminate both uninvolved medium, ions and large molecular weight compounds such as bovine serum albumen.

ONLR-NPC Lysates

The invention is also directed to ONLR-NPC cellular lysates. The ONLR-NPC lysates of the invention comprise all cellular components from a single ONLR-NPC or from a population of ONLR-NPCs.

ONLR-NPC lysates are produced by rupturing cellular membranes and collecting all of the resulting materials. ONLR-NPC lysates may be prepared by collecting the ONLR-NPCs grown in appropriate medium through centrifugation, washing, and disruption of the cells. Means for rupturing cellular membranes include mechanical, ultrasonic, physical, enzymatic, chemical and osmotic mechanisms. Mechanical mechanisms include repeated freeze/thaw cycles, sonication, pressure, and filtration. Chemical mechanisms include detergents such as Triton X-100. Osmotic mechanism include subject the cells to hypo- or hyper-tonic environments. Physical mechanisms include scraping and collecting cells from culture plates.

ONLR-NPC Extracts

The invention is also directed to ONLR-NPC cellular extracts. The ONLR-NPC extracts of the invention comprise less than all of the cellular components from a single ONLR-NPC or from a population of ONLR-NPCs.

ONLR-NPC extracts may be produced from ONLR-NPCs by first rupturing cellular membranes, through such means as described herein, and then collecting or isolating selected cellular materials, such as one or more growth factors.

ONLR-NPC extracts may also be produced from ONLR-NPC cultures by collecting conditioned media into which selected cellular materials, such as growth factors, have been secreted and then isolating selected cellular materials from the collected media.

ONLR-NPC extracts may further be produced by preparing an "artificial" ONLR-NPC extract that comprises selected cellular materials, such as growth factors (e.g. one or more of the growth factors listed in Table 1, i.e. VGF, TGFB1, LTBP1, LTBP2, PDGFB, CTGF, FGF11, NDNF, PDGFC, TGFβ2, NGF, FGF1, Midkine, VEGFA, MANF, IGF-1, and IGF-2), produced by means other than the ONLR-NPCs, such as by collecting the cellular materials from media of cells engineered to produce the selected cellular materials. The "artificial" ONLR-NPC extracts of the invention include (i) those having one or more of the growth factors of Table 1, (ii) those having one or more of the proteins of Table 2, and (iii) those having one or more of the growth factors of Table 1 and those having one or more of the proteins of Table 2.

Means for producing and isolating the cellular materials are well known to the skilled artisan and will vary depending on the identity of the cellular material(s) to be collected or isolated, and the manner in which they are produced. However, suitable means include centrifugation, filters and columns to screen materials based on size, antibody coated chips, plates and columns to isolate peptides/proteins, for example, based on binding affinity.

Compositions Comprising Factors Secreted by ONLR-NPCs

As indicated above, the ONLR-NPCs of the invention can be defined based on expression of one or more of the secreted factors provided in Table 1 and/or expression of one or more of the proteins provided in Table 2. While the factors will be known the one skilled in the art, the present invention also includes (i) compositions comprising at least 5, 6, 7, 8, 9, 10, 11, 12, 13, 14, 15, 16 or each of the secreted factors provided in Table 1, (ii) compositions comprising at least 5, 6, 7, 8, 9, 10, 11, 12, 13, 14, 15, 16 or each of the proteins provided in Table 2, and (iii) compositions comprising at least 5, 6, 7, 8, 9, 10, 11, 12, 13, 14, 15, 16 or each of the secreted factors provided in Table 1 and at least 5, 6, 7, 8, 9, 10, 11, 12, 13, 14, 15, 16 or each of the proteins provided in Table 2.

Methods of Treatment

The invention is also directed to methods of treating or preventing optic nerve diseases. Because ONLR-NPCs are thought to play a role in supporting glial cell growth and development, and by extension, myelination of axons as they emerge from the eye, ONLR-NPCs and the factors they secrete are likely to have activity in treating or preventing optic nerve hypoplasia, regional axonal dysfunction and hypomyelination. ONLR-NPCs and the factors they secrete may also enable glial cell replacement and remyelination.

The methods of treating or preventing optic nerve diseases of the invention comprise administering to a subject in need thereof a therapeutically effective amount of a composition comprising one or more of:

(i) a population of ONLR-NPCs,
(ii) ONLR-NPC conditioned media,
(iii) an ONLR-NPC lysate,
(iv) an ONLR-NPC extract, and
(v) one or more factors secreted by ONLR-NPCs, thereby treating or preventing an optic nerve disease in the subject.

Optic nerve diseases that may be treated using the methods of the present invention include, but are not limited to, open-angle glaucoma, angle-closure glaucoma, optic nerve hypoplasia, optic nerve hypomyelination, regional axonal dysfunction, nonarteritic anterior ischemic optic neuropathy (NAION), and optic neuritis.

In one aspect, the composition comprises one or more factors secreted by ONLR-NPCs, wherein the factors are selected from the group consisting of Nerve Growth Factor (NGF), Latent Transforming Growth Factor-Beta 1 (TGF-β1), Fibroblast Growth Factor 1 (FGF1), Vascular Endothelial Growth Factor (VEGF), Mesenchymal Astrocyte Neurotrophic Factor (MANF), Connective Tissue Growth Factor (CTGF), and Insulin-like Growth Factors-1 and -2 (IGF-1 and IGF-2). In another aspect, the composition comprises one or more of the proteins produced by ONLR-NPCs listed in Table 2. In further aspect, the composition comprises one or more of the secreted factors of Table 1 and one or more of the proteins of Table 2.

In each of the methods of the present invention, a "therapeutically effective amount" of a composition comprising one or more of (i) a population of ONLR-NPCs, (ii) ONLR-NPC conditioned media, (iii) an ONLR-NPC lysate, (iv) an ONLR-NPC extract, and (v) one or more factors secreted by ONLR-NPCs is administered to a subject. The effective amount will vary between subjects and the identity of the optic nerve disease being treated. However, the effective amount is one that is sufficient to achieve the aim or goal of the method.

In the methods of the invention, the composition may be administered to the eye of the subject, such as via topical application to the surface of the eye (e.g. eye drops), via subconjunctival injection, via intravitreal injection into the interior of the eye, or via retrobulbar injection into the space behind the globe of the eye. Such injections include depot injection through the conjunctiva.

Administration of the composition may be via any of the means commonly known in the art. When administered to the eye, such routes include topical and intraocular, subconjunctival and retrobulbar injections. When administered to sites other than the eye, such routes include intravenous, intraperitoneal, intramuscular, subcutaneous and intradermal routes of administration, as well as topical, nasal application, by inhalation, orally, rectally, vaginally, or by any other suitable mode.

The pharmaceutical compositions of the present invention may be formulated, for example, for topical, intraocular, oral, sublingual, intranasal, rectal, transdermal, mucosal, pulmonary, or parenteral administration. Parenteral modes of administration include without limitation, intradermal, subcutaneous (s.c., s.q., sub-Q, Hypo), intramuscular (i.m.), intravenous (i.v.), intraperitoneal (i.p.), intra-arterial, intramedullary, intracardiac, intra-articular (joint), intrasynovial (joint fluid area), intracranial, intraspinal, and intrathecal (spinal fluids). Any known device useful for parenteral injection or infusion of drug formulations can be used to effect such administration. In preferred aspects on the invention, the composition is administered to the subject as a topical drop for ophthalmic administration.

Appropriate doses and dosing schedules can readily be determined by an attending physician without undue experimentation depending on the characteristics of the subject to be treated and the identity of the optic nerve disease. Administration frequencies for the compositions of the present invention include 4, 3, 2 or once daily, every other day, every third day, every fourth day, every fifth day, every sixth day, once weekly, every eight days, every nine days, every ten days, bi-weekly, monthly and bi-monthly. The duration of treatment will be based on the optic nerve disease being treated and will be best determined by the attending physician.

In the methods of the invention, the composition administered to the subject may be in the form of a pharmaceutical formulation comprising (a) one or more of (i) a population of ONLR-NPCs, (ii) ONLR-NPC conditioned media, (iii) an ONLR-NPC lysate, (iv) an ONLR-NPC extract, and (v) one or more factors secreted by ONLR-NPCs and (b) a pharmaceutically acceptable carrier.

Suitable examples of carriers are well known to those skilled in the art and include water, water-for-injection, saline, buffered saline, dextrose, glycerol, ethanol, propylene glycol, polysorbate 80 (Tween-80™), poly(ethylene) glycol 300 and 400 (PEG 300 and 400), PEGylated castor oil (e.g. Cremophor EL), poloxamer 407 and 188, hydrophilic and hydrophobic carriers, and combinations thereof. Hydrophobic carriers include, for example, fat emulsions, lipids, PEGylated phospholipids, polymer matrices, biocompatible polymers, lipospheres, vesicles, particles, and liposomes. The terms specifically exclude cell culture medium. The formulations may further comprise stabilizing agents, buffers, antioxidants and preservatives, tonicity agents, bulking agents, emulsifiers, suspending or viscosity agents, inert diluents, fillers, and combinations thereof.

The subject may be a human, a non-human primate, bird, horse, cow, goat, sheep, a companion animal, such as a dog, cat or rodent, or other mammal.

III. EXAMPLES

A. Experimental Protocols

Mouse Optic Nerve (ON) and Optic Nerve Lamina Region (ONLR) Dissection for Immunohistochemistry (IHC)

ON and ONLR used for IHC were isolated from mice perfused with 4% paraformaldehyde-phosphate buffered saline (PFA), by enucleating eye globes, leaving at least 3 mm of attached ON. The remaining ON was collected following craniotomy, removing the ON and adjacent optic chiasm. Tissues were then placed in 2% PFA, overnight, rinsed and transferred to 30% sucrose for sectioning. Tissue was embedded in optimal temperature cutting solution (OCT), frozen at −80° C.; and 10 um cross- or longitudinal sections were cut using Leica cryostat.

Immunohistochemistry (IHC) Procedure

Sections were subjected to antigen retrieval procedure following fixation. Briefly, sections were incubated in 10 mM sodium citrate buffer for 10 min at 80° C., rinsed and blocked with 2% normal donkey serum for 1 hr, incubated with the primary antibody; see antibody list in Table 4) overnight at 4° C. Sections were then rinsed in PBS containing 0.5% Triton X100, incubated with appropriate secondary antibody for one hour at 25° C., counterstained with DAPI, mounted on a slide with appropriate medium and stored at 4° C. until use.

Dissection and Culture of Mouse Lamina and ON Tissue Neural Progenitor Cells (NPCs)

The globes and attached ONs of appropriately aged (typically 17-18d) mice were enucleated, leaving at least a 3 mm stump of ON attached. Distal ON was obtained separately, measured from the distal stump. Typically, at least 10 laminae were collected for NPC isolation. Tissues were then placed into a 100 mm culture dish with cold Hibernate-A® (GIBCO A12475-01) until dissociation, and the medium changed immediately prior to dissociation.

ONLRs were isolated from the globe by trimming adjacent ON to 3 mm in a laminar flow hood. A small hole was made at the base of the globe 1 mm from the ON stump using a 29 ga needle. Vannas scissors were used to dissect around the ONLR and adjacent ON. The remaining sclera was removed, leaving only the ON and sheath adjacent to the nerve, as it inserts into the globe. ONLR sections were trimmed to 800 microns distally. The ON sheath was carefully dissected from the ONLR by rolling back the sheath with a 29 gauge needle-knife and Vannas scissors, and isolated ONLR tissues were placed into ice-cold Hibernate-A® media. Because of the small size, mouse ONLRs were not further triturated (unlike human, which were triturated using 2-29 ga needles as knives). Two mm of distal ON, separated from the ONLR by at least 2 mm, were isolated in a similar manner and dissected into smaller pieces using 29 ga needle knives. Tissues were placed into a 1.5 ml microcentrifuge tube containing 300 ul of Hibernate-A® media and kept on ice.

ONLR-NPC and ON Cell Cultivation

Plates were coated with 15% Matrigel® (VWR/Corning, cat #354234) diluted in DMEM for a minimum of one hour prior to cell addition at room temperature. Immediately before cell plating, unbound Matrigel was carefully aspirated, and 200 ul of complete NT2 medium (see below) was added per well of a 24-well plate (cat no. 662102 CELL-STAR®).

Briefly, ON/ONLR tissues were centrifuged at 300×g for 3 min. Hibernate-A® media was discarded and replaced with Dulbeccos complete phosphate buffered saline (DPBS) containing penicillin/streptomycin (GIBCO cat #15140-122). The ON/ONLR tissues were placed on ice for 5 min, then centrifuged at 300×g for 3 min. The DPBS solution was discarded, and the ON/ONLR tissue was washed twice with fresh DPBS.

300 ul of collagenase (1 mg/ml in sterile DPBS; GIBCO cat #17104-019) was added to the tissues, and these were incubated at 37° C., for 10-15 mins. The latter time was used depending on the degree of tissue digestion, to eliminate residual undigested tissues. Solutions were aspirated 10-15 times at 10 minutes using a p1000 pipette to homogenize tissues, avoiding air bubbles from forming. Tissue was placed for a further 5 min at 37° C. for digestion if required. An equal volume of complete NT2 medium (see composition below in Table 3) was then added to the tubes, centrifuged at 300×g for 5 min, and the supernatant (containing collagenase) was discarded. The resulting pellet was resuspended 5 times using a p1000 pipettor, to enable even cell distribution into 1 ml of media, containing 0.5 ul/ml of fungizone (GIBCO cat #15290-018), and an aliquot of the dissociated cells were counted manually using a hematocytometer.

Cells were plated according to cell density. Up to two additional volumes of medium were added if the bottom of the cell plate was not visible in the Matrigel® coated 24-well plates. Cells were then placed into a humidity controlled incubator at 37° C. supplemented with 5% $CO_2$. Final volume in each well was ~500 ul. The cells were then left untouched for five days prior to initial feeding to enable cell adherence to the plate prior to addition of new media. Wells were supplemented with 250 ul/well additional fresh medium. Cells were subsequently fed every 2-3 days thereafter with complete NT2 medium. ½ of the old medium (250 ul) was removed during each subsequent feeding. Medium was prepared fresh every 2 weeks. Matrigel was applied to the well one hour prior to cell reseeding.

TABLE 3

Complete NT2 media composition

| Component | Company | Cat # | Final Concentration |
|---|---|---|---|
| Neurobasal | Invitrogen | 21103049 | 48% |
| DMEM/F12 | Invitrogen | 11330032 | 48% |
| B27-50x | Invitrogen | 12587010 | 1% |
| NC-N2 suppl | Invitrogen | 17502048 | 0.5% |
| Insulin | Sigma-Aldrich | 05165 | 0.1% |
| BSA | MP Biomedicals | 199896 | 0.5 mg/ml |
| FGF-2 | R&D Systems | 233-FB | 10 ng/ml |
| FGF-4 | R&D Systems | 235-F4 | 10 ng/ml |
| Gentamicin | Invitrogen | 15750060 | 2 µg/ml |

Immunocytochemistry (ICC) of Cultured Cells

Plated cells used for ICC were aspirated and rinsed twice with DPBS and fixed in 4% PFA for 10 min. Cells were subsequently rinsed twice with DPBS-0.05% Triton (DPBST) for 10 min and incubated with primary antibody (see list of primary antibodies in Table 4) in 5% (Donkey Normal Serum) at 4° C. overnight. Following two additional rinses with DPBST, cells were incubated with appropriate secondary antibodies for 1 hour at RT (1:500 dilution in DPBST-5% normal serum). Afterwards cells were rinsed twice with DPBS (5 min), counterstained with DAPI (1:10K), mounted with fluorescence enhancing media and observed at confocal Zeiss LSM 510 microscope.

TABLE 4

| Antibody | Type | Company | Catalog # |
|---|---|---|---|
| Anti-NG2 Chondroitin sulfate proteoglycan | Monoclonal | Millipore | MAB5384 |
| Anti-Nestin (rat/mouse) clone 401 | Monoclonal | Millipore | MAB353 |
| Anti-Nestin (human) | Polyclonal | Sigma | N5413 |
| Anti-SOX2 (mouse/human) | Polyclonal | Abcam | ab97959 |
| Anti-SOX2 (human/mouse) | Monoclonal | Thermo-Fisher | 20G5/ MA1-014 |
| Anti-SOX1 (human/mouse) | Polyclonal | Cell Signaling | #4194 |
| Anti-NeuN (mouse/human) | Monoclonal | Millipore | MAB377 |
| Anti-TUJ1 (human/mouse) | Monoclonal | DHSB | 6G7 |
| A2B5 (human/mouse) | Monoclonal | Abcam | ab53521 |
| Olig-1 | Monoclonal | Neuromab | N149/25 |
| GFP | ms Polyclonal | Invitrogen | A11122 |
| GFP | ck Polyclonal | Millipore | #06-896 |
| AQP4 (human/mouse) | Polyclonal | Alomone | AQP-014 |
| GFAP (human/mouse) | Monoclonal | Abcam | GF5/ ab10062 |
| GFAP (human/mouse) | Polyclonal | Dako | Z0334 |
| MBP (human/mouse) | Polyclonal | Sigma-Ald | M3821 |
| $O_4$ (human/mouse) | Monoclonal | Millipore | MAB345 |
| Ki67 (human/mouse) | Rbt monocle | Abcam | ab16667 |
| PAX6 (chicken) | Monoclonal | DHSB | P3U1/ ab528427 |
| PAX2 (human) | Polyclonal | Abcam | AB38738 |
| SCA-1 (mouse) | Polyclonal | Millipore | AB4336 |
| STRO-1 (human) | Monoclonal | Millipore | MAB4315 |

Formation and Immunostaining of Neurospheres from Mouse ON/Lamina/SVZ Cultured Cells Formation of neurospheres (NS) was induced from second passage mouse ON/ONLR/SVZ stem cells growing on Matrigel® following growth to approximately 70% confluency. Half of the NT2 media was removed. Cells were carefully detached using a cell scraper and transferred using a p1000 pipette to a new 50 mL tube. An equal volume of fresh NT2 media was added to the tube and the cells were re-distributed evenly in the media by gentle aspiration. The cells were then transferred to an Ultra-Low Attachment Surface 6-well Plate (CORNING cat #3471 Costar®). 500 ul of NT2 media was added to the wells prior to the cell seeding. Fresh NT2 media was added every 2-3 days. NS formation was observed between 4-7 days. NS were counted and imaged. For IHC, NS were collected from the plates and allowed to settle at the bottom of an Eppendorf tube. The excess media was removed and NS were rinsed with DPBS, pipetted gently to ensure even distribution and fixed in 2% PFA for 30 min at 4° C. Subsequently NS were rinsed in 10 mM glycine for 10 min with gentle shaking to prevent clumping, and collected at 300×g for 2 min. Excess glycine was removed and neurospheres were placed in 5% sucrose for 1 hr at 4° C., cryoprotected in 30% sucrose, fixed in OCT at −80° C. and sectioned at 10 um.

In Vivo Transgenic Animal Studies

All experimental protocols and procedures with mice were approved by Institutional Animal Care and Utilization Committee (IACUC; Baltimore, MD, USA). Mice (both genders) were housed in polycarbonate cages with density of 5 mice/cage on a 12-h light/dark cycle. Mice had access to food and water ad libitum. Animals were mated to corresponding strains and tail DNA analyzed using the appropriate PCR primers to ensure appropriate genotype(s). Non-mutant mice of the same background were used as controls.

B6.129(Cg)-Gt(ROSA)26Sortm4(ACTB-tdTomato, -EGFP)Luo/J mice were crossed with B6; 129S-Sox2tm1 (cre/ERT2)Hoch/J. Appropriately identified genotyped double-mutant progeny were used for experimental procedures. These were Tm1(cre/ERT2)Hoch-Sox2/J) X Gt(ROSA)26Sortm td-Tomato, GFP)Luo/JO, and referred as Sox-GFP mice.

B6.129S-Sox2tm1(cre/ERT2)Hoch/J mice were crossed with B6.129P2-Gt(ROSA)26Sortm1(DTA)Lky/J and double mutants were used for experimental procedures. The double mutants are referred as Sox-DTA mice.

Tamoxifen and 4-Hydroxytamoxifen (4OHT) Injections

Tamoxifen or 4OHT injections (intraperitoneal (ip) and local-retrobulbar (RB), respectively) were used to induce Cre recombination. 4OHT was used for local injections because Tamoxifen is a prodrug that needs to be metabolized by the liver to 4OHT which itself is the active form. 30 mg of Tamoxifen (Sigma, cat #5648) was moistened in 100 ul of 100% ethanol, vortexed for 30 sec, and 900 ul of sunflower seed oil (Sigma, cat #5007) was added. The mixture was revortexed, sonicated for 2 min on ice. 80 ul of Tamoxifen was subsequently injected ip (~15-20 mg mouse) four times over 5 days. Retrobulbar 4OHT injections (Cayman, cat #17308) were prepared as a 30 mg/ml suspension in 10% ethanol and 90% ethoxylated castor oil (Kolliphor: Sigma, cat #5135). Five microliters of this mixture was injected behind the eye (RB injection).

Injection and Tissue Harvesting Schedule: Sox-GFP Mice

Tm1(cre/ERT2)Hoch-Sox2/J) X Gt(ROSA)26Sortm td-Tomato, GFP)Luo/JO injections were performed either ip or locally (RB), according to the following times. Postnatal: 19d injection/all sexes; euthanized 14d, 30d and 60d post-injection. Adult: injection at 60d PN/all sexes; euthanized at 14d or 30d post-injection. Adult/aged: 6 mo, 1 y, 2 y ON and ONLR cell culture: tissues were collected postmortem from perfused animals following terminal anesthesia.

SOX2-DTA Mice

These were double mutants consisting of Tm1(cre/ERT2) Hoch-Sox2/J) X Gt(ROSA)26Sortm1(DTA)Lkyb. It was determined that i.p. Tamoxifen injections were routinely fatal within 10 days, likely due to global stem cell suppression. For this reason, local (RB) 4OHT administration was utilized. The local approach had the added advantage of enabling the use of the contralateral eye of each animal as its own vehicle control. Animals were injected on one side with 4OHT, and the contralateral side with vehicle (Kolliphor).

Postnatal: 19d RB injection/all sexes; euthanized at 3d, 14d or 30d post-injection Adult: 60d injection/all sexes; Animals were euthanized at 14d or 30d post-injection Human ONLR Dissections and Stem Cell Cultivation Fixed human tissues used for immunohistochemistry were obtained from a commercial donor source (Lions Eye Institute for Transplant and Research, Tampa, FL), following institutional review board (IRB) exemption. Human tissue used for cultivation was obtained from freshly isolated post-surgical specimens following enucleation for severe, irreparable damage without hope of recovery, and to prevent development of post-damage autoimmune response to the contralateral eye (sympathetic ophthalmia). Specimens were obtained following University of Maryland Medical Center IRB approval. Eye tissues used for this purpose was stripped of identifiable information except for sex. Tissues used for ONLR-NPC cultivation were taken directly from the operating room on ice, with maximum times from enucleation to final cultivation of 3 hours post enucleation.

To minimize contamination, enucleated tissues were initially dipped twice in 5% povidone iodine-DPBS solution, and washed twice in sterile DPBS before dissection. The optic nerve and adjacent lamina entering the globe was located and carefully cut away from the globe, using a sterile Vannas scissors. 5 mm of adjacent nerve emerging from the globe was used for laminar isolation. The optic nerve sheath was removed using the Vannas scissors, as was the scleral wall surrounding the lamina as it emerges from the globe. The anterior 2 mm of the retina entering the scleral wall was excised. The intact ONLR was placed onto a 6-well plate with 1 mL of ice-cold sterile Hibernate-A® media. The isolated ONLR tissue was triturated using Vannas scissors, and tissue transferred into a sterile conical tube and centrifuged at 300 g for 5 min. Hibernate-A® media was discarded and replaced with DPBS containing penicillin/streptomycin (GIBCO cat #15140-122). The ONLR tissue was placed on ice for 5 min. It was then centrifuged at 300×g for 3 min, the DPBS solution discarded, and the ONLR tissue washed twice with DPBS. One mL of collagenase (1 mg/ml in sterile DPBS GIBCO cat #17104-019) was added to the tissue, and manual dissociation of the tissue was used to break up larger pieces. It was then placed into the incubator for activation, at 37° C., for 15-20 mins (dependent on state of tissue digestion).

A p1000 pipette (with a large bore tip) was used to further dissociate the tissue, by aspirating 20-30 times carefully to avoid formation of air bubbles, and then the tissue was placed for a further 5-10 min at 37° C. for digestion. An equivalent volume of complete NT2 medium was added to the tube, centrifuged at 300×g for 5 min, and the supernatant discarded. The pellet was evenly resuspended in 2 ml of NT2 medium containing 0.5 ul/ml of fungizone (GIBCO cat #15290-018) using a p1000 pipette. Cells were plated onto 15% Matrigel® coated 6-well plates and placed into a humidity controlled incubator at 37° C. The cells were then left unmolested for three days to allow the cells to adhere to the plate before the addition of new media.

Human ONLR Neurosphere Formation

Human ONLR cells were grown to 70% confluence and then transferred onto new Matrigel® following each sub-culture (SC). After SC2 human ONLR cells were transferred onto an Ultra-Low Attachment Surface 10 cm Plate (CORNING cat #3262). Half of the NT2 media from the well was removed from the well. Cells were carefully detached using a cell scraper and transferred using a 5 mL serological pipette to a new 50 mL tube. An equal volume of fresh NT2 media was added to the tube and the cells were re-distributed evenly in the media by gentle pipetting up and down using a 5 mL serological pipette. The cells were then transferred to an Ultra-Low Attachment Surface 10 cm plate (CORNING cat #3262). 5 mL of NT2 media was added to the wells prior to the cells being plated. Fresh NT2 media was added every 2-3 days. NS formation took between 7-14 days, upon which NS were counted and imaged. The ONLR NS were also fixed, sectioned and stained.

RNA Isolation from Eye Tissues and Cultures

Because the ONLR region has such a high concentration of extracellular matrix, the standard procedure was modified by combining two RNA isolation procedures: Phenol/Guanidinium (RNAbee: Tel-Test Cat #CS-104B). Initial RNA isolation was followed by genomic DNA removal and further RNA clean up procedure using the Qiagen (RNeasy micro kit, Cat #74004). This combination enhanced carbohydrate removal, and improved RNA yields appreciably. ONLR and ON RNA was isolated from a minimum of 10 pooled samples (5 animals/prep). Total RNA was isolated identically from retina, ONLR and optic nerve. Total RNA was evaluated for yield and A260/A280 ratios using nanodrop, and for quality using an Agilent RNA Nano electropherogram. Samples with RNA integrity number (RIN) below 8 were discarded.

Real Time Qualitative Polymerase Chain Reaction (RT-PCR)

First strand cDNA synthesis was performed using Invitrogen SuperScript First-Strand synthesis system (Cat #11904-018) or Superscript III (Cat #18080-051) with random primers. qPCR was performed using iQ SYBR Green Supermix from Bio-Rad (Cat #170-8882) on an iCycler (Biorad). The 15 ul qPCR reaction contained 1×SYBR Green Supermix, 400 nM gene specific primers and various amounts of first strand cDNA, which was diluted to 1:10 in water depend on the abundance of the gene tested. The gene specific primers were obtained from IDT (Integrated DNA Technologies) pre-designed primers or custom designed using the "Pick Primers" program on the NCBI website. The parameters were set to have a product size of less than 200 bp, 58-61° C. annealing temperature and crossed exon boundaries for forward and reverse primers, to further reduce the chance of results skewed by genomic contamination (sees Table 5 and 6 for detailed information). The optimal primer pair and amount of cDNA used in the reaction were also determined by the standard curve, which was required to yield better than 90% amplification efficiency. qPCR reactions were performed on the following parameter: 95° C. 5 minutes for first denaturation, followed by 40 cycles of denaturation at 95° C. for 30 sec, annealing at 60° C. for 30 sec, and extension at 72° C. for 30 sec, and a final 5 min extension. Reactions which yielded single melting curve were used in the quantitative analysis. The ΔΔCt. method of comparing relative sequence abundance was utilized, employing two internal control genes for quality, consistent with MIQE guidelines. All assays were run in duplicate.

TABLE 5

Nucleotide primers used for gene expression

| Gene symbol Cell type | Acc# | Sequence 5'-3' | Polarity | Product Size (bp) | Tnt ° C. |
|---|---|---|---|---|---|
| Nes NPC | NM_016701 | GAGGCGCTGG AACAGAGATT (SEQ ID NO: 1) CACAGCCAGC TGGAACTTTTC (SEQ ID NO: 2) | Plus Minus | 75 | 60 |
| SOX1 NPC | NM_009233 | GGCAGTCATAC AAAAGTTGGC (SEQ ID NO: 3) GTACAGTATTT ATCGTCCGCAG A (SEQ ID NO: 4) | Plus Minus | 104 | 60 |
| SOX2 NPC | NM_011443 | CAGGAGTTGT CAAGGCAGAGA (SEQ ID NO: 5) CTTAAGCCTC GGGCTCCAAA (SEQ ID NO: 6) | Plus Minus | 133 | 60 |

TABLE 5-continued

Nucleotide primers used for gene expression

| Gene symbol Cell type | Acc# | Sequence 5'-3' | Polarity | Product Size (bp) | Tnt ° C. |
|---|---|---|---|---|---|
| CSPG4/NG2 OPC | NM_139001 | GACCAACCCC CGBGGCGCAC (SEQ ID NO: 7) TGGGCCCGAA TCATTGTCTG (SEQ ID NO: 8) | Plus Minus | 108 | 60 |
| ALDH1L1 NPC/Astro | NM_027406 | GCCTTGTTGA TATCCCGAGT (SEQ ID NO: 9) GCCCATCATG ATCATCTCTG (SEQ ID NO: 10) | Plus Minus | 117 | 60 |
| Gli1 Hedgehog effector | NM_010296 | TGTGTAAGCA GAGCTCATGC (SEQ ID NO: 11) CATAGGGTCT CGGGGTCT (SEQ ID NO: 12) | Plus Minus | 130 | 60 |
| Msi1 NPC | NM_008629 | TGAGAGGGAT AGCTGTGAGC (SEQ ID NO: 13) GTTCCAAGCC ACGACCTAC (SEQ ID NO: 14) | Plus Minus | 140 | 60 |
| PAX6 Early Neuron | NM_013627 | CACGTACAGT GCTTTGCCAC (SEQ ID NO: 15) AACTCCGCCC ATTCACTGAC (SEQ ID NO: 16) | Plus Minus | 134 | 60 |
| Shh Adult NSCs | NM_009170 | CGTAAGTCCT TCACCAGCTTG (SEQ ID NO: 17) GAATCCAAAGC TCACATCCAC (SEQ ID NO: 18) | Plus Minus | 131 | 60 |
| Ppib Reference gene | NM_011149 | GAGACTTCAC CAGGGGAGAT (SEQ ID NO: 19) AAAACCACATG CTTGCCATCC (SEQ ID NO: 20) | Plus Minus | 193 | 60 |
| GAPDH Reference gene | NM_00804 | CAGCAAGGACA CTGAGCAAGA (SEQ ID NO: 21) | Plus Minus | 104 | 60 |

TABLE 5-continued

Nucleotide primers used for gene expression

| Gene symbol Cell type | Acc# | Sequence 5'-3' | Polarity | Product Size (bp) | Tnt °C. |
|---|---|---|---|---|---|
| | | GCCCCTCCTG TTATTATGGGG (SEQ ID NO: 22) | | | |

TABLE 6

Nucleotide primers used for genotyping

| Genotype | Sequence 5'-3' | Tann | Product (bp) |
|---|---|---|---|
| ER2-SOX2-Cre | GCGGTCTGGCAG TAAAACTATC (SEQ ID NO: 23) GTGAAACAGCAT TGCTGTCACTT (SEQ ID NO: 24) | 51.7° C. | 100 |
| ROSA-DTA mt | CGACCTGCAGGT CCTCG (SEQ ID NO: 25) CTCGAGTTTGTC CAATTATGTCAC (SEQ ID NO: 26) | 65° C. | 650 |
| ROSA-DTA wt | CCAAAGTCGCTC TGAGTTGTTATC (SEQ ID NO: 27) GAGCGGGAGAA ATGGATATG (SEQ ID NO: 28) | 65° C. | 604 |
| Td-Tom common | CTCTGCTGCCT CCTGGCTTCT (SEQ ID NO: 29) | 62° C. | 575 |
| Td-Tomato mt | TCAATGGGCGG GGGTCGTT (SEQ ID NO: 30) | 69° C. | 250 |
| Td-Tomato wt | CGAGGCGGATC ACAAGCAATA (SEQ ID NO: 31) | 62° C. | 330 |

Vascular Imaging Using Fluorescein-Linked Bovine Serum Albumin (FITC-BSA).

FITC-BSA was prepared and dissolved in porcine gelatin (Sigma-Aldrich) as previously described (Nicholson et al, 2012). Terminally anesthetized animals were transcardially-perfused with the dissolved reagent after clamping the descending aorta and allowing for continuous flow through the opened right atrium. The neck vasculature was clamped following perfusion, and the animal immersed in an ice water bath for 30 minutes to set the gelatin. The eyes and adjacent ON were dissected and post-fixed in 4% PF-PBS for three days. ONLR and ONs were dissected as previously described, and the tissue imaged using a Zeiss two-photon microscope to a depth of 500 um.

Transmission Electron Microscopy

Terminally anesthetized mice were transcardially-perfused with 2% PF-PBS and ocular tissues isolated and post-fixed in buffered fixative containing paraformaldehyde and glutaraldehyde. Tissues were stained with uranyl acetate and embedded in Epon, and cross-sectioned at 200 nm. The anterior ON region was evaluated 1 mm from the globe (avoiding the ONLR), and the distal ON 4 mm from the globe, using a Tecnai transmission electron microscope at 2100× and 4400×. Quantification of the differences in relative axonal myelination was performed by counting axons using 5-2100× micrographs per optic nerve.

ON-Myelin Thickness Ratio (Q-Ratio)

Q-ratios were evaluated from five cross sections/optic nerve at 4400× using quantification of individual axons provided by Image J. The inner (unmyelinated) and outer (myelinated) area of each axon was defined using the freehand outline-polygon function, and each area was converted to their circular equivalents. The ratio of inner/outer radius for each axon was determined; data from axons were pooled into very small (<400 nm), small (400-600 nm) medium (600-800 nm), large (800-1000 nm), very large (1000-1200 nm), and giant (>1220 nm) axons.

B. ONLR Structure is Consistent with an NPC Niche

The mammalian ONLR in humans and rodents presents as a narrow band of unmyelinated tissue directly adjacent to the retina (FIG. 1B). The mouse ONLR's cellular organization was examined, with its boundaries defined by an absence of myelin, using the oligodendrocyte- and OPC-specific 04 antibody (Table 4) (FIG. 1D, in green). Expression of the NPC-expressed intermediate filament protein nestin was also evaluated (Park et al., 2010). Filamentous nestin expression in the ON is localized to the unmyelinated ONLR (FIG. 1D, in red). Glial fibrillary acidic protein (GFAP), another adult NPC marker (Gorris et al., 2015), is co-expressed by the majority of ONLR-nestin expressing cells (FIG. 1F). The water channel protein aquaporin 4 (AQP4) is expressed at high levels in astrocytes (Cavazzin et al., 2006), and at reduced levels in NPC niche sites (Tavazoie et al., 2008). Confocal analysis revealed that ONLR-AQP4 expression levels are reduced (FIG. 1E, in green), despite the abundant presence of astrocytes, compared with either retina or distal ON (FIG. 1E, Retina and ON).

Whether cells in the ONLR express SOX2 protein, another hallmark of NPCs, was examined. Many cells in the ONLR that express both filamentous nestin and SOX2 were found (FIG. 1G, arrowheads), while nearly all cells in the distal ON do not (inset, FIG. 1G). SOX2-expressing cells make up nearly 50% of all nuclei in the 60d mouse lamina (FIG. 1H, 247±31.8 SOX2(+) nuclei/ONLR v. 486±41.6 total ONLR nuclei, n=3 eyes; ±sem), while comprising only 17% of nuclei in the mid-ON region (FIG. 1H; 207±17.9 SOX2(+) nuclei/ON v. 1193±127 nuclei/ON, n=3; ±sem). Nestin/GFAP expression is lost in the distal ON (FIGS. 1G and J insets). ONLR-SOX2-expressing cells also express GFAP (FIG. 1J). Hence, the ONLR includes numerous cells co-expressing these three characteristic markers of adult NPCs.

To determine ONLR cell proliferation, in vivo mitotic activity was quantified using Ki67 antibody (Table 4) in 60d (adult) ONLR, and compared to the distal ON region (FIG. 1I). The ONLR contains ~6.2 times as many mitotic nuclei (per unit nuclei) and 3.5-fold higher mitotic nuclei (per unit area) than the distal ON (inset, FIG. 1, N=3 eyes/group). An increased mitotic index of ONLR-NPCs relative to surrounding tissue is consistent with their role in adult neural cell replacement (Stoll et al., 2011).

NPCs in the adult CNS in vivo give rise to neurons as well as astrocyte and oligodendrocyte progeny (Ahlenius et al., 2009). However, no expression of the early neuronal markers doublecortin, PAX6 or NeuN was found in the ONLR (data not shown). SOX2(+) ONLR cells are NG2(−) (FIG. 1K, ONL and also compare ONL and ON in FIG. 1L). NG2(+)/nestin (−) OPCs were detectable as a band of cells in the area immediately below the ONLR. Their location adjacent to the ONLR is consistent with possible derivation from ONLR-NPCs (FIG. 1K and inset; also FIG. 1L, arrows). These results suggest that ONLR-resident SOX2 expressing cells constitute a population distinct from SOX2 (+)/NG2(+) OPCs. Together these results reveal that the ONLR is a mitotically active region of the ON, enriched with a unique population of SOX2(+)/nestin(+)/GFAP(+) cells, consistent with other NPC niches in the central nervous system (CNS).

CNS-NPC niches have a vascular plexus (Shen et al., 2008; Tavazoie et al., 2008). The ONLR vasculature is a plexus (schematic, FIG. 1A) derived from three distinct vascular supplies: retina, choriocapillaris and optic nerve. Rat ONLR vasculature was evaluated using two-photon microscopy, and mouse ONLR vasculature by serial section and reconstruction using neuroleucida (MBF; Williston VT) following filling with a fluorescein-gelatin mixture (rat vasculature is shown in FIG. 1C) (Nicholson et al., 2012). ONLR vascular complexity is greater than that of the distal ON (FIG. 1C; quantification in 1C inset) and similar to the adjacent retina (FIG. 1C inset; data adapted from Balaratnasingam et al., 2014). The ONLR's increased vascular complexity is another characteristic of CNS-NPC niches (Shen et al., 2008; Tavazoie et al., 2008).

C. NPCs are Concentrated in the ONLR

Figure 2:
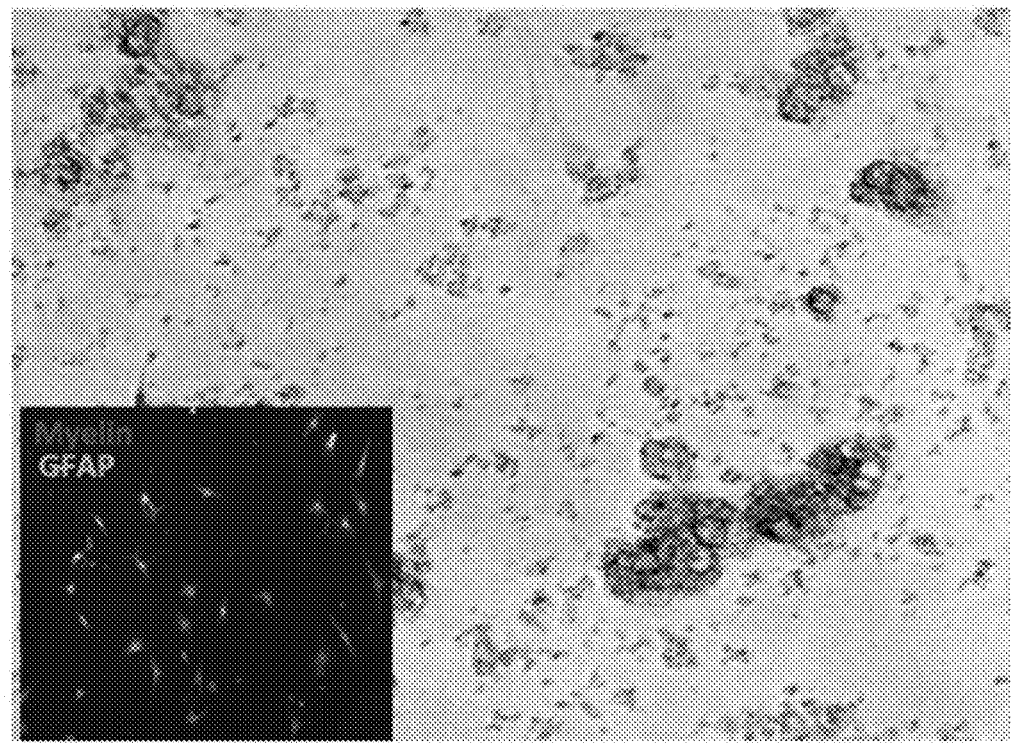
FIG. 2. Characterization of murine ONLR cell cultures and differential gene expression of ONLR. A. 21d ONLR culture (no supplementation). Cells exhibit poor growth, and rapid differentiation into GFAP(+) astrocytes and $O_4$(+) oligodendrocytes (inset). B. 21d culture of ONLR cells, matrigel supplementation. Cells generated colonies; cells had extended processes consistent with neural and/or astrocytic morphology. Inset: Attached neurosphere on a coated plate. C. Early ONLR neurospheres. Inset shows subventricular zone (SVZ)-derived neurospheres from the same animals for comparison. Scale: 100 um. D. ONLR cells grown on matrigel express NPC markers nestin (green) and SOX2 (red). Left inset: individual ONLR-NPCs express both markers. Right inset: nestin(+)/SOX2(+) SVZ-NPCs (arrows) from the same animal grown in similar conditions. E. Neurosphere formation quantification from pup (17d) and adult (60d) ONLR- and distal ON segments. Neurosphere formation ability is greatest in ONLR of both ages. F. Cultured ONLR-NPCs express SOX2 and GFAP (arrows). GFAP (in red), SOX2 (in green). G. SOX2/A2B5 co-expression. H. Nestin/NG2 expression. There is minimal colocalization and cells strongly expressing NG2 do not express nestin (arrowhead), suggesting that nestin(+) progenitors give rise to OPCs. I. SOX2/NG2 expression in one-month cell cultures. NG2(+) (green) cells have multiple cytoplasmic projections, and SOX2(+) nuclei (in red). J. Nonprogenitor A2B5(+) cells (red) alongside NPC-derived OPCs. These cells have a flattened, monotonous morphology. OPCs are A2B5(+)/NG2(+). K. Tuj1 (early neuronal) expression in 21d ONLR cultures (arrow). L. ONLR cultures after differentiation with FBS. Nestin expression is absent. Cells rapidly develop into either $O_4$(+) (red) myelinating cells with prolific membranes consistent with oligodendrocytes, or GFAP(+) (green) cells with astrocyte-consistent morphology. M. Expression characteristics table of the two main cell types found in non-differentiated ONLR cultures (NPCs: 10% of cells; non-NPCs: 90% of cells). ONLR-NPCs simultaneously express nestin, SOX2 and GFAP, while non-NPCs do not. N. rqPCR of total RNA obtained from retina, ON, and ONLR. ONLR expresses the highest level of nestin, and expresses other progenitor-expressed proteins such as Sox1 and Sox2.
Figure 2:
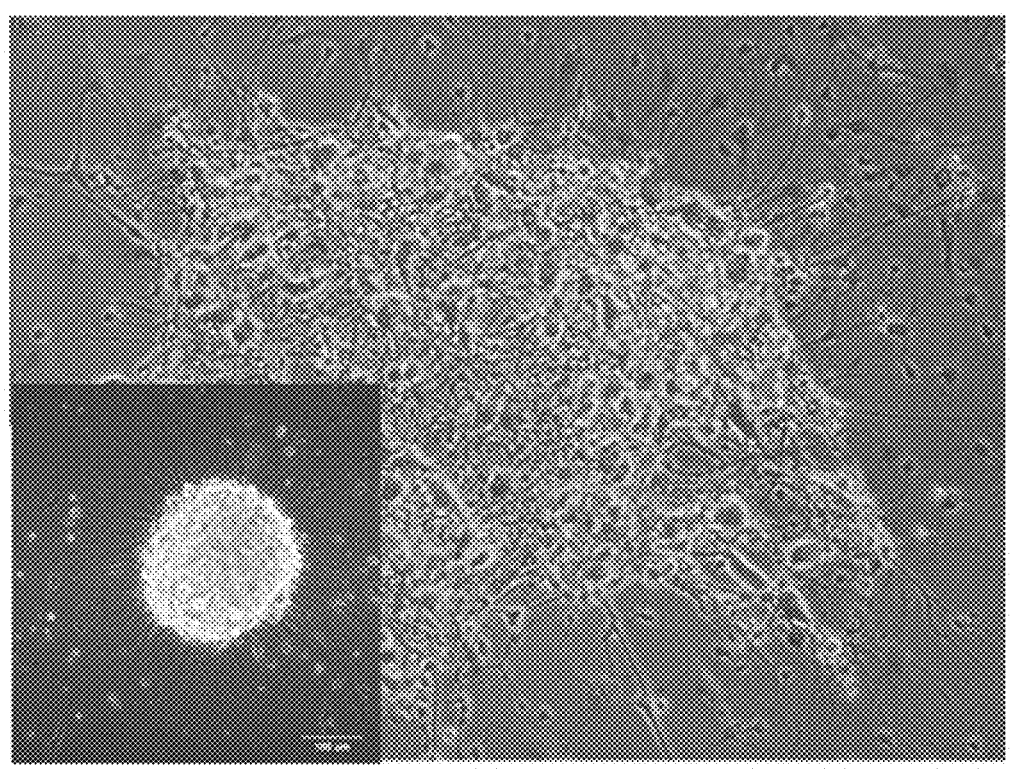
Figure 2:
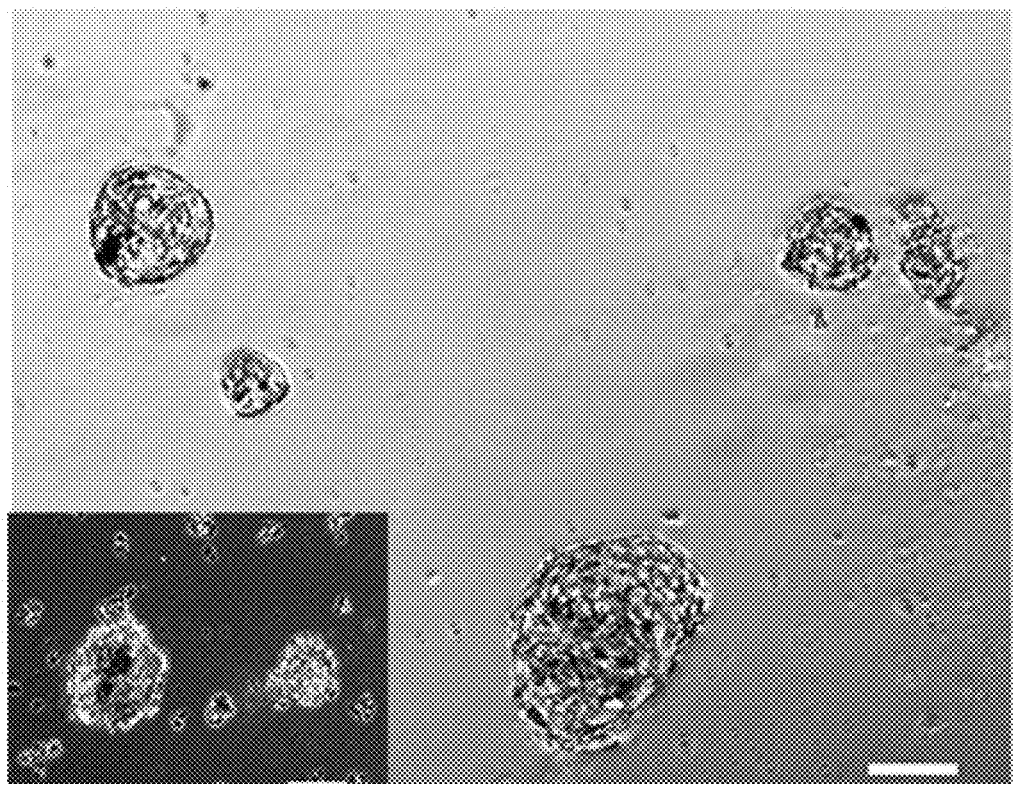
Figure 2:
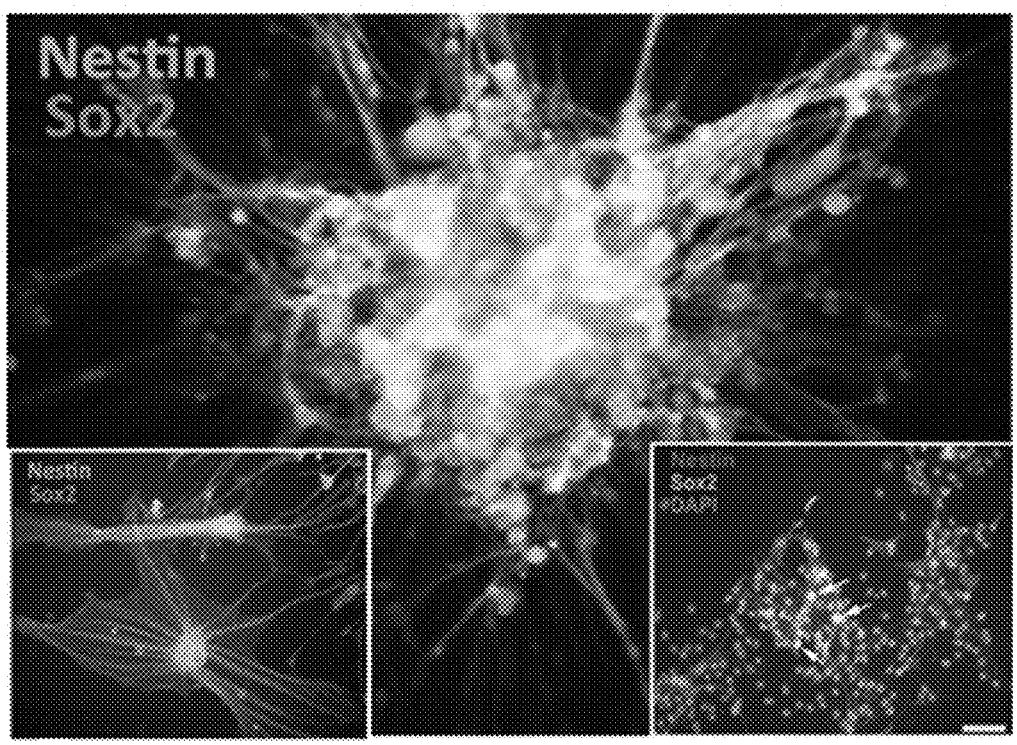
Figure 2:
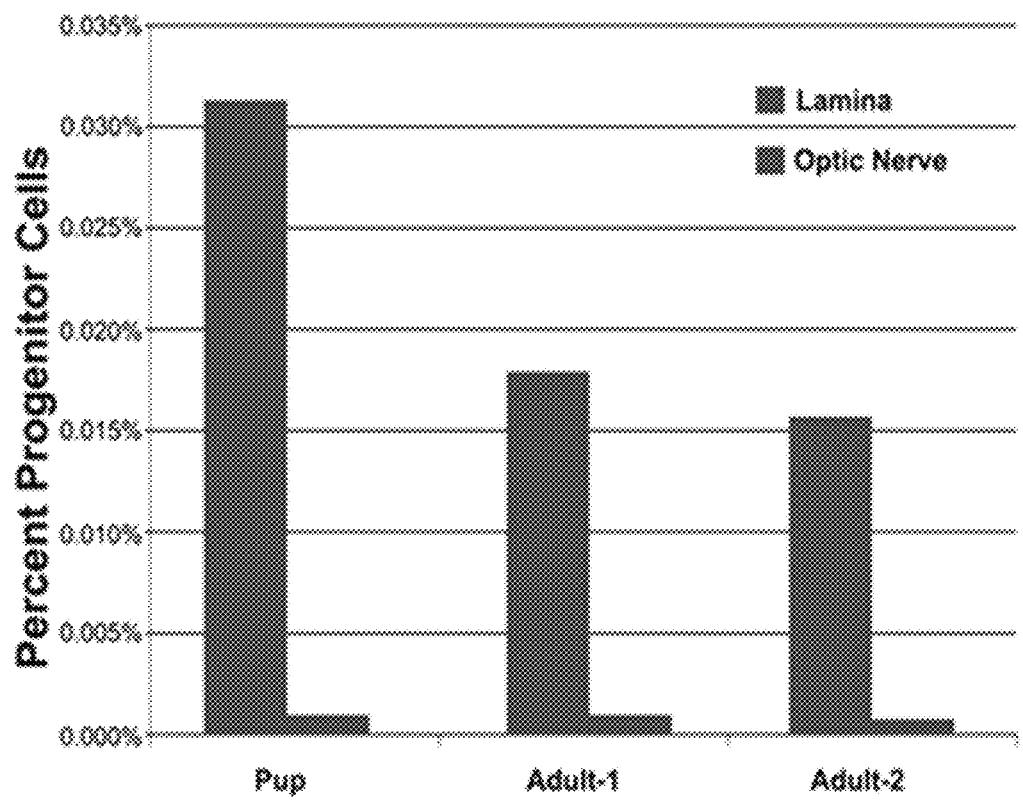
Figure 2:
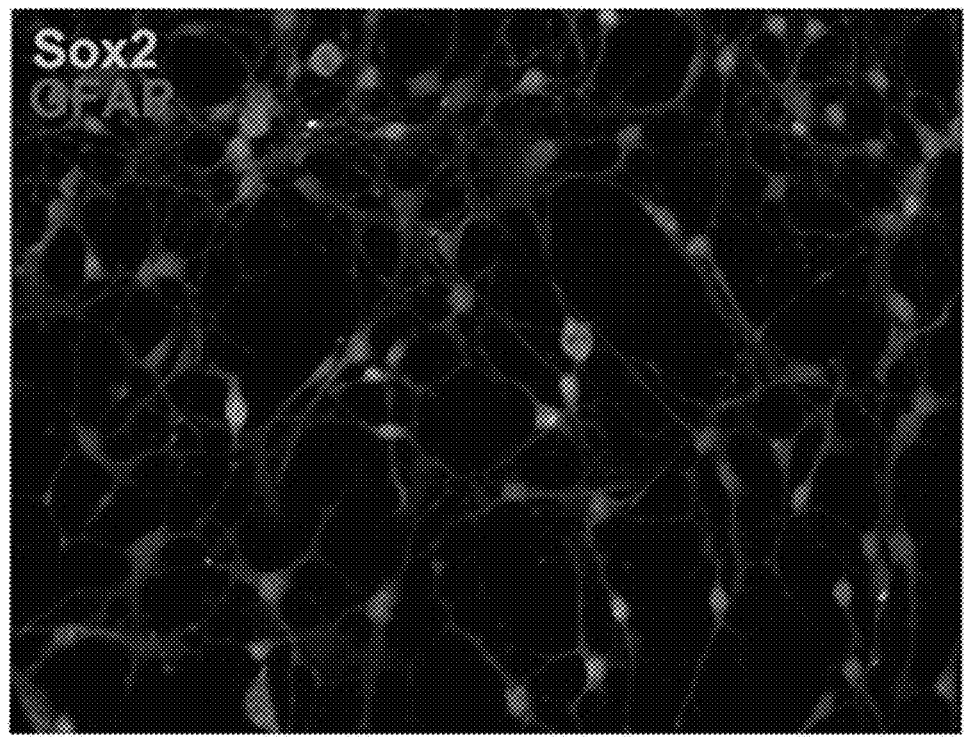
Figure 2:
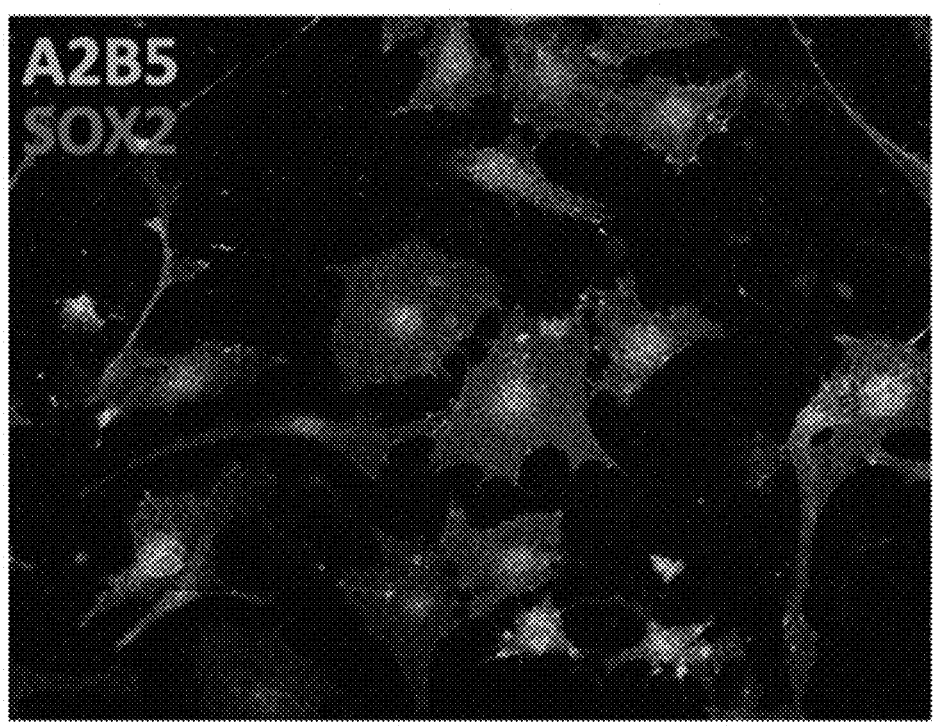
Figure 2:
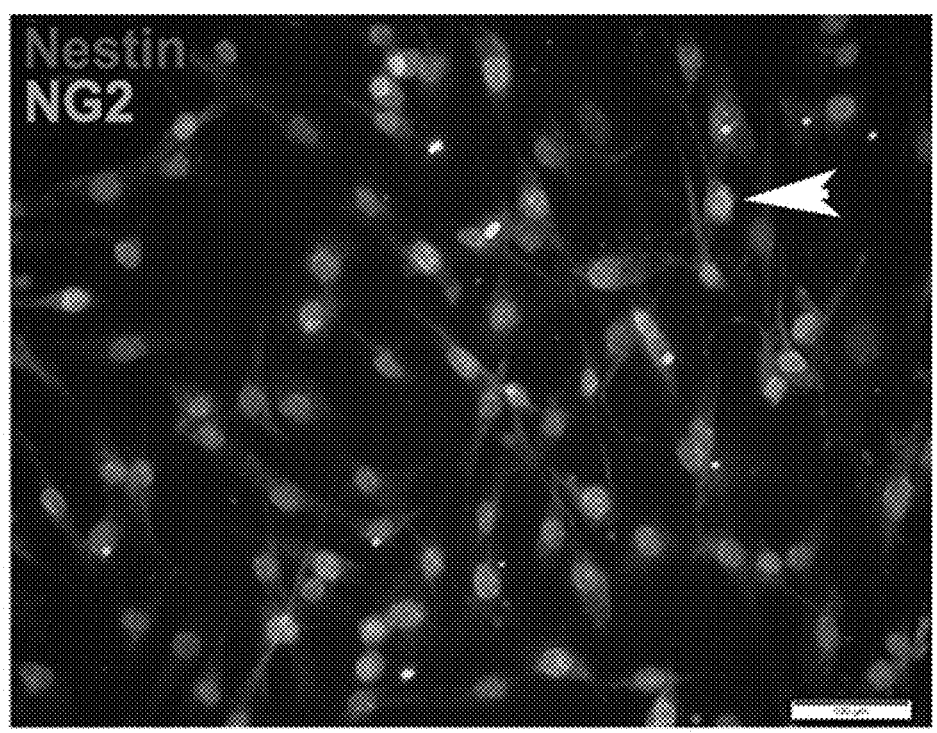
Figure 2:
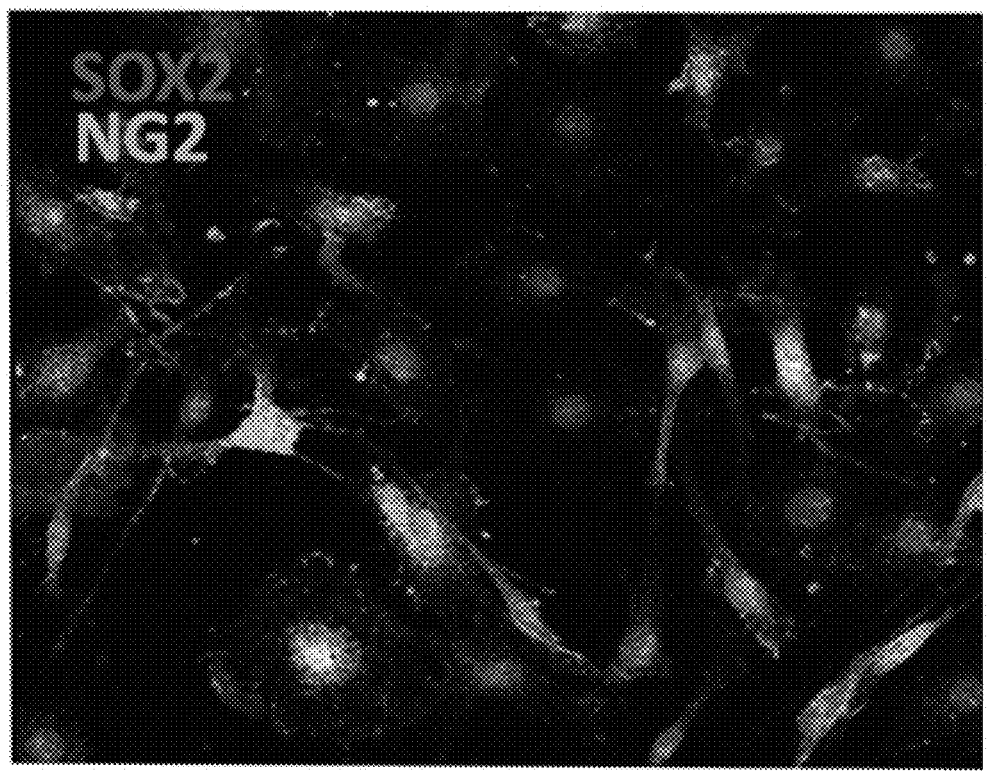
Figure 2:
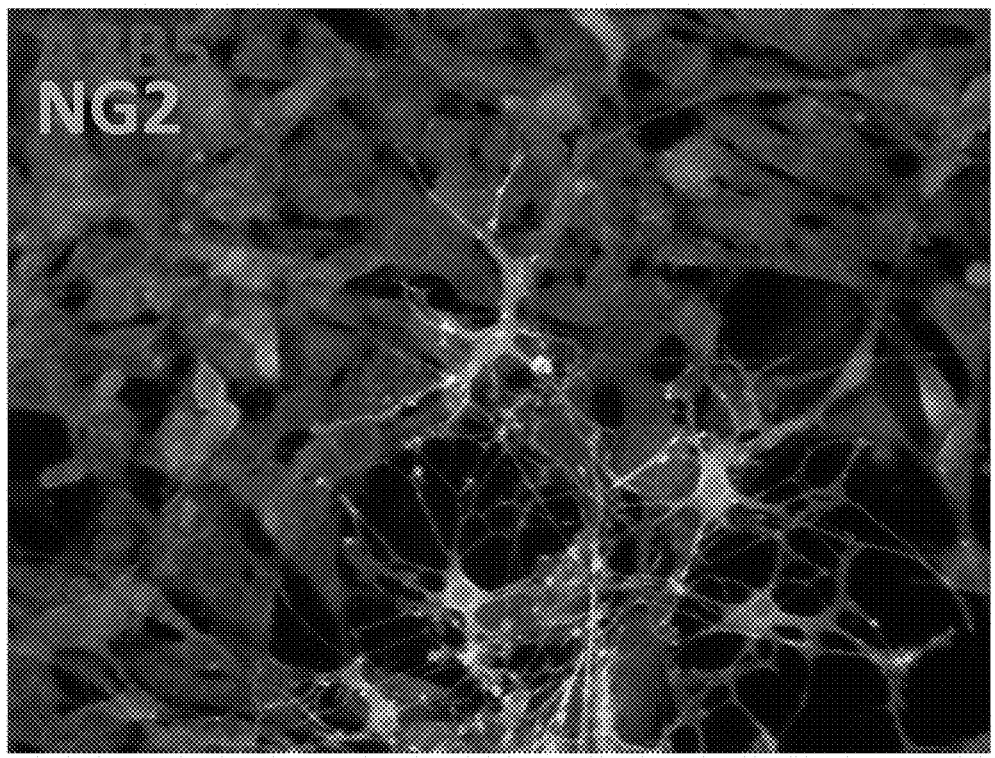
Figure 2:
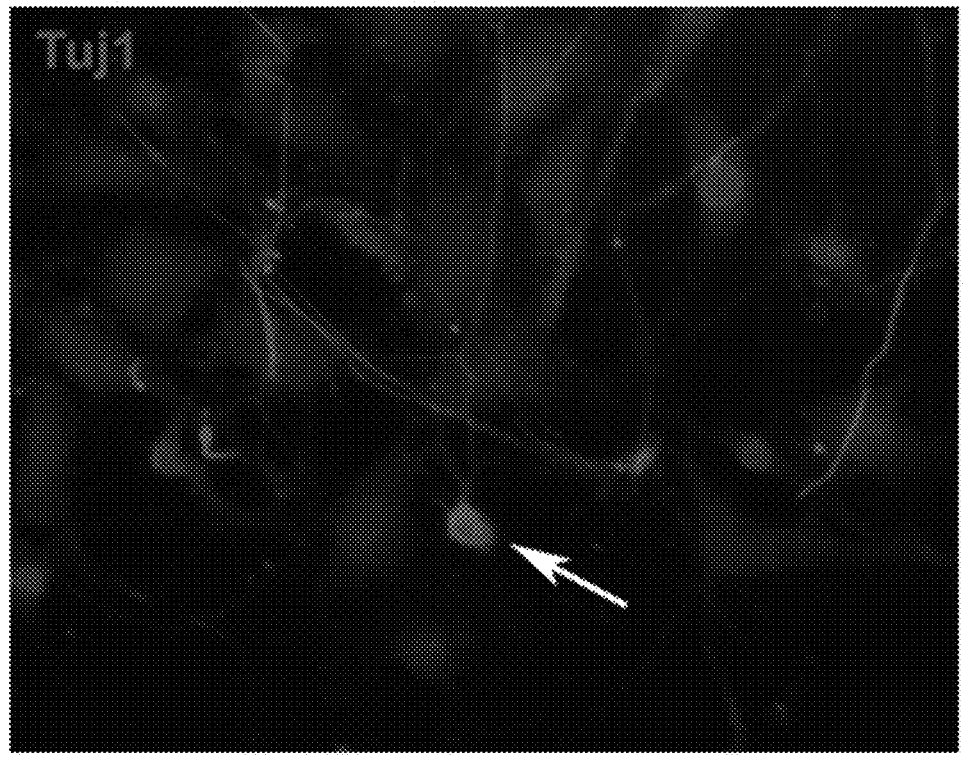
Figure 2:
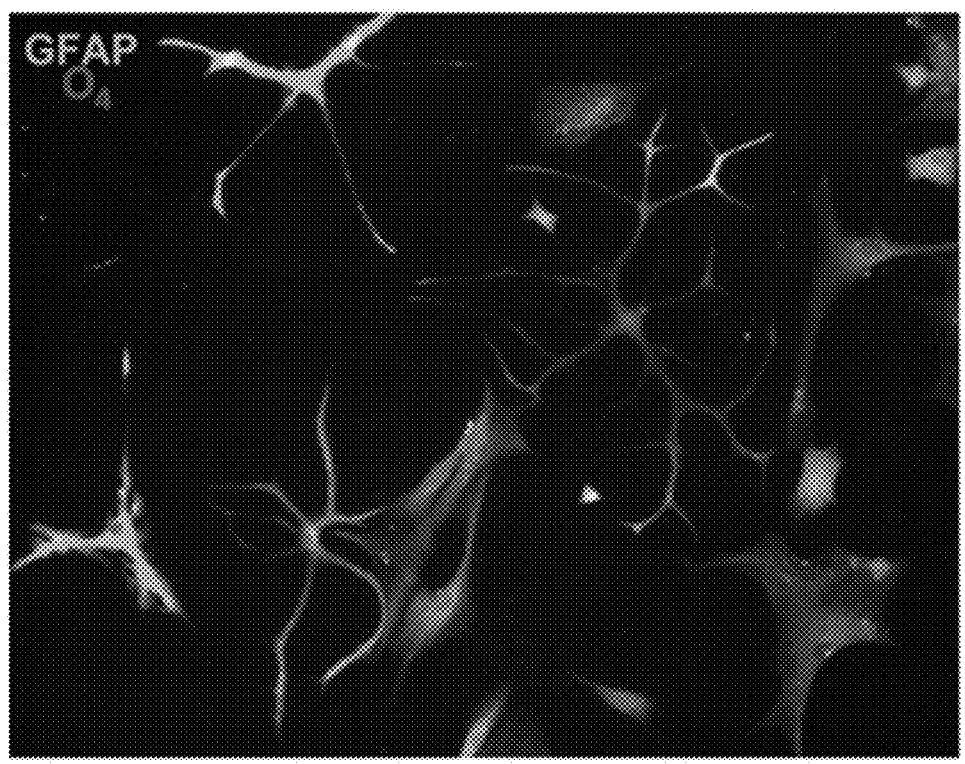
Figure 2:
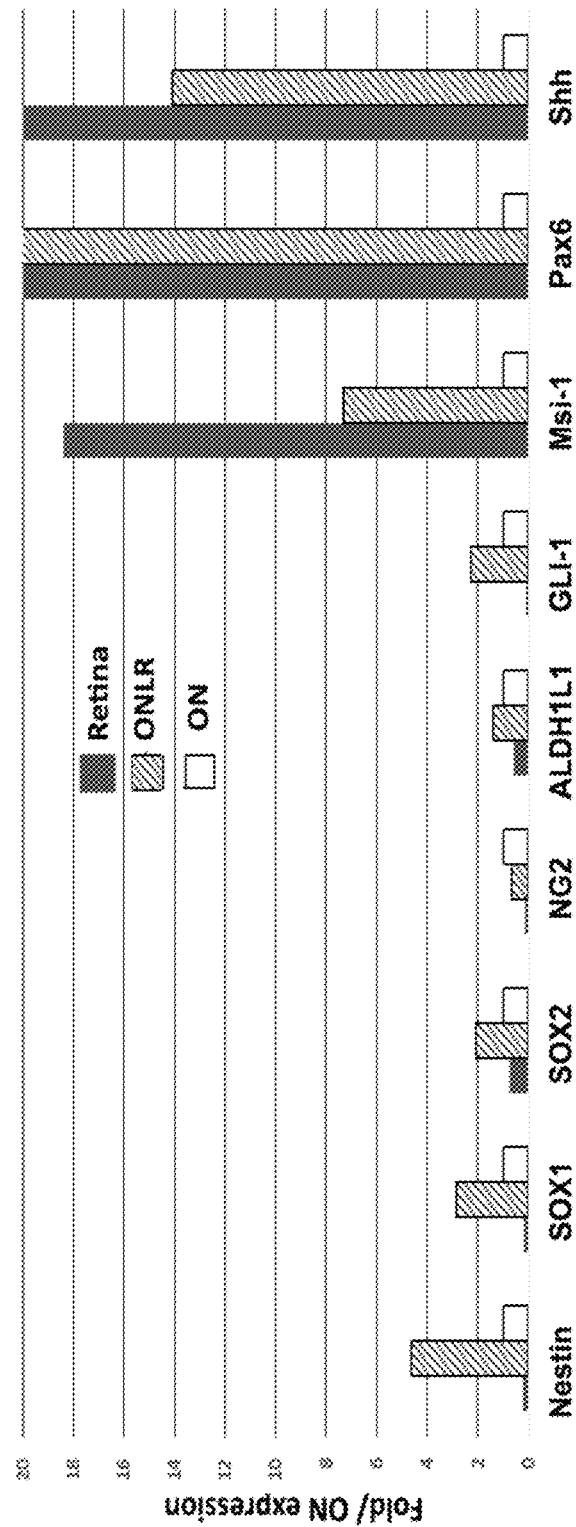

Cells from ONLR (the first 500 µm of ON behind the globe) and distal ON (>2 mm from the globe) tissues were dissociated from young (PN 20d) and adult (60d) animal. Cells were cultured utilizing medium supplemented with FGF2 and Matrigel. Without Matrigel, there was poor growth from both laminar and ON cultures (FIG. 2A; ONLR), with cells on adherent surfaces expressing either GFAP or $O_4$ (FIG. 2A, inset) and were morphologically similar to astrocytes and oligodendrocytes. Optimal propagation of ONLR cultures required concentrations of 10-15% Matrigel (methods) (FIG. 2B). Distal ON cultures consistently yielded few colonies, even with Matrigel (FIG. 2E, in red).

Matrigel-supplemented ONLR cells initially formed flattened colonies (FIG. 2B), containing numerous cells with a NPC-like appearance, although cultures were consistent with a mixed cell population. ONLR colonies on low adhesion medium from the second passage onward formed neurospheres after dissociation (FIG. 2C), similar to those seen with NPC derived from the SVZ (FIG. 2C; inset). Neurospheres regrown on coated plates developed cells with fine processes (FIG. 2B, inset). Two major cellular populations were detected: a minor fraction (10% of cells) with NPC-like morphology (FIG. 2B), and these were shown to be mitotically active by Ki67 staining (data not shown), as well as nestin(+) and SOX2(+). These cells co-expressed nestin and SOX2 (FIG. 2D, and left inset), SOX2 and GFAP (FIG. 2F), and A2B5/SOX2(+) (FIG. 2G; arrows). The ONLR NPC-like cells provided a continual source of astrocytes, distinguishable by their morphology and GFAP immunostaining. Along with astrocytes, NG2(+)/nestin (−) cells were detected (arrowhead, FIG. 2H). As nestin(+) cells gradually acquired NG2 expression, their nestin signal progressively declined. This data is consistent with the in vivo results shown in FIGS. 1K and L.

While many nestin(+)/SOX2(+) and SOX2(+)/NG2(+) cells were seen in culture (FIG. 2I), the loss of nestin in NG2(+) cells, coupled with the enhanced ability of ONLR cultures to form neurospheres, suggests that ONLR-nestin (+)/SOX2(+) cells are distinct from the NG2(+)-OPC population but capable of giving rise to SOX2(+)/NG2(+) OPCs. This observation is important because it suggests that ONLR-nestin expressing cells are at a more primitive progenitor stage than OPCs. ONLR cultures gave rise to rare (0.016%) NeuN/Tuj1 (+) cells (FIG. 2K). Thus, ONLR Sox2/Nestin/GFAP(+) cells represent a distinct NPC population that can potentially give rise to all neural cell types, including OPCs. ONLR cultures supplemented with 10% FBS generated either GFAP(+) astrocyte-type cells (FIG. 2L, in green) or $O_4$(+) membranous oligodendrocyte-type cells (FIG. 2L, in red). ONLR-NPCs are thus pro-gliogenic, with the propensity to differentiate into macroglia in vivo, in culture, but in culture can also give rise to neurons.

Despite the ONLR's enhanced ability to form neurospheres, most (90%) ONLR-derived cultured cells were distinctly different from cells with NPC morphology. These were flattened, often stellate in appearance (FIG. 2J), A2B5 (+)/SOX2 (−)/nestin (−), making them distinct from NG2(+) OPCs (FIG. 2J, in green). Culture results are summarized in FIG. 2M.

ONLR cell neurosphere-forming ability was quantified using $2^{nd}$ subculture passage-dissociated cells in low adhesion medium. ONLR cultures generated neurospheres (FIG. 2C) co-expressing NPC markers nestin and SOX2. 0.016-0.03% of ONLR cells could generate neurospheres (graph FIG. 2E). NPC frequency in the ONLR population is similar to that previously reported for hippocampus and subcortical white matter (WM) (Lojewski et al., 2014). Dissociated distal ON cells were capable of generating less than 1 neurosphere per $10^6$ cells (0.0007-0.0009%; FIG. 2E, red bars; n=3 experiments), implying that cells in the distal ON of both young and old animals have little self-renewal capacity. ONLR-neurospheres could be generated from both 17d pups and mature (60d) animals, but ONLR from mature animals generated fewer neurospheres compared with pups (FIG. 2E, compare blue bars in pup vs adult). A diminished capacity of cells from mature animals to generate neurospheres in vitro corresponds with the in vivo data showing reduced nestin expression and declining numbers of SOX2 (+) cells in the ONLR of aged animals (FIGS. 5A and 5B), suggesting that this progenitor cell population declines during aging.

NPC-associated gene expression was compared from adult mouse (60d) retina, ONLR and ON tissues via rq-PCR (FIG. 2N). ONLR tissue expressed high nestin, Sox1- and -2 and Msi-1 levels (FIG. 2N). While ONLR expressed higher levels of Pax6, Brn3b and Shh, than did ON (compare ON and ONLR; FIG. 2N), this expression may be due to ONLR sample contamination due to the ONLR's retinal proximity (FIG. 2N; compare retina and ONLR).

D. Transgenic Confirmation of ONLR-NPCs

A number of the current generation of commercially available SOX2 antibodies cross-react with other SOX family members (unpublished data; for comparison see Tiwari et al., 2014). A cross-reacting SOX2 mouse monoclonal antibody initially resulted in overestimates of ONLR and ON-SOX2(+) nuclear numbers. Later studies utilized a rabbit polyclonal antibody that confirmed the relative SOX2 expression pattern seen in the transgenic experiments (below).

In vivo SOX2 expression was confirmed in ONLR and ONs using a reporter mouse strain expressing Cre under control of the SOX2 promotor, where Cre expression is further restricted by the use of the ER2 receptor that binds only tamoxifen or its active metabolite, causing activation only in cells with active SOX2. This mutant gene is referred to as SOX2-Cre. This enabled selective identification of the timing of postnatal SOX2 activity, and also allowed utilization of constructs whose expression would be fatal during embryogenesis (see below).

Figure 3:
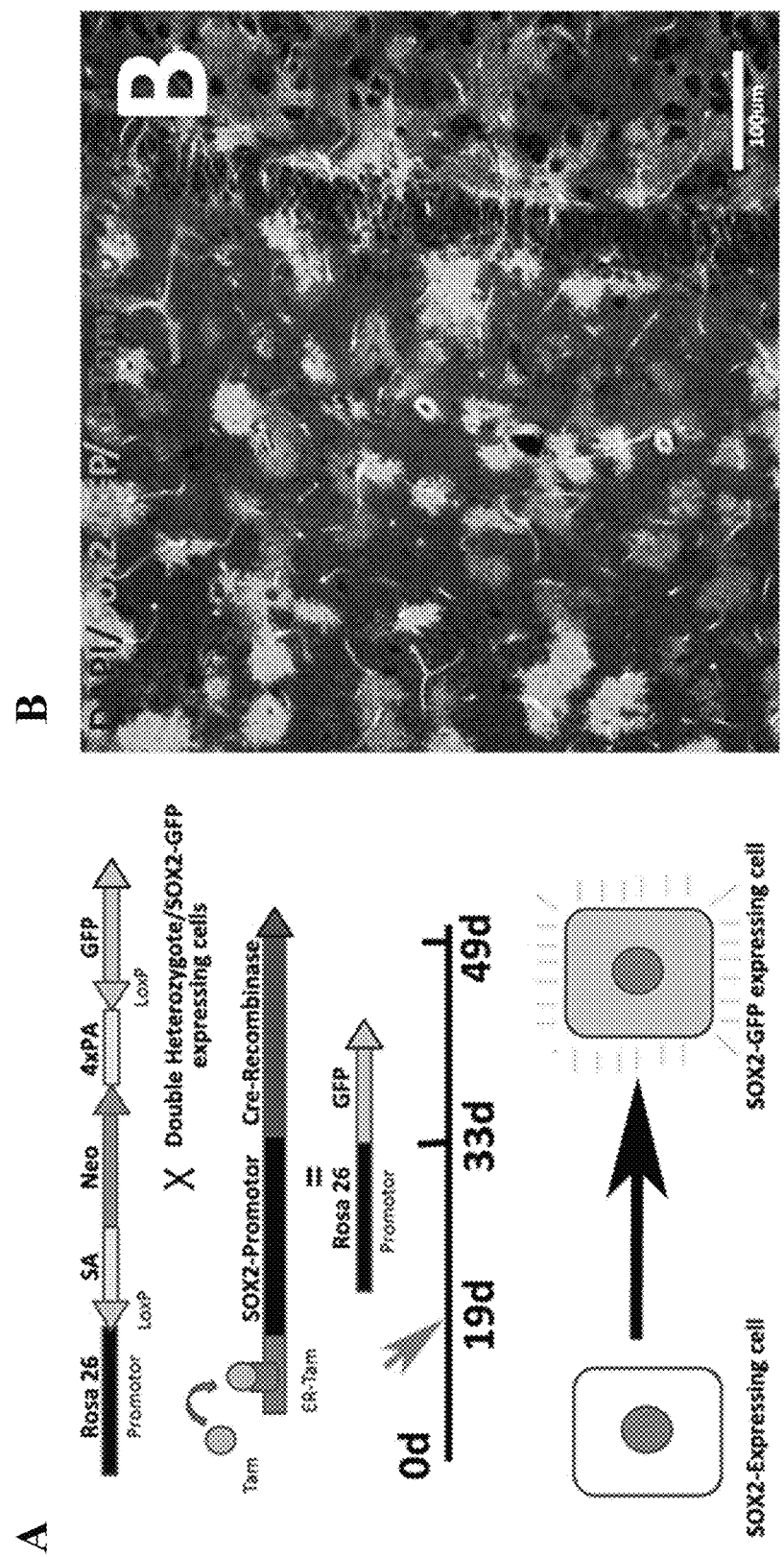
FIG. 3. GFP induction patterns in SOX2-Cre reporter mice. A. Schematic of 4OHT/Tamoxifen induction in 19d PN SOX2-GFP animals. The unrecombined ROSA26 locus constitutively expresses td-Tomato (red cytoplasm; background cells in panel 3B). Tamoxifen enables Cre recombinase expression in SOX2-expressing cells, with recombined cells expressing GFP in parents and their progeny. Animals were injected systemically (IP) with tamoxifen or locally (retrobulbar) with 4OHT (Schematic, FIG. 3A; orange arrow). Tissues were collected either at 14d post-induction (33d postnatal brain.
Figure 3:
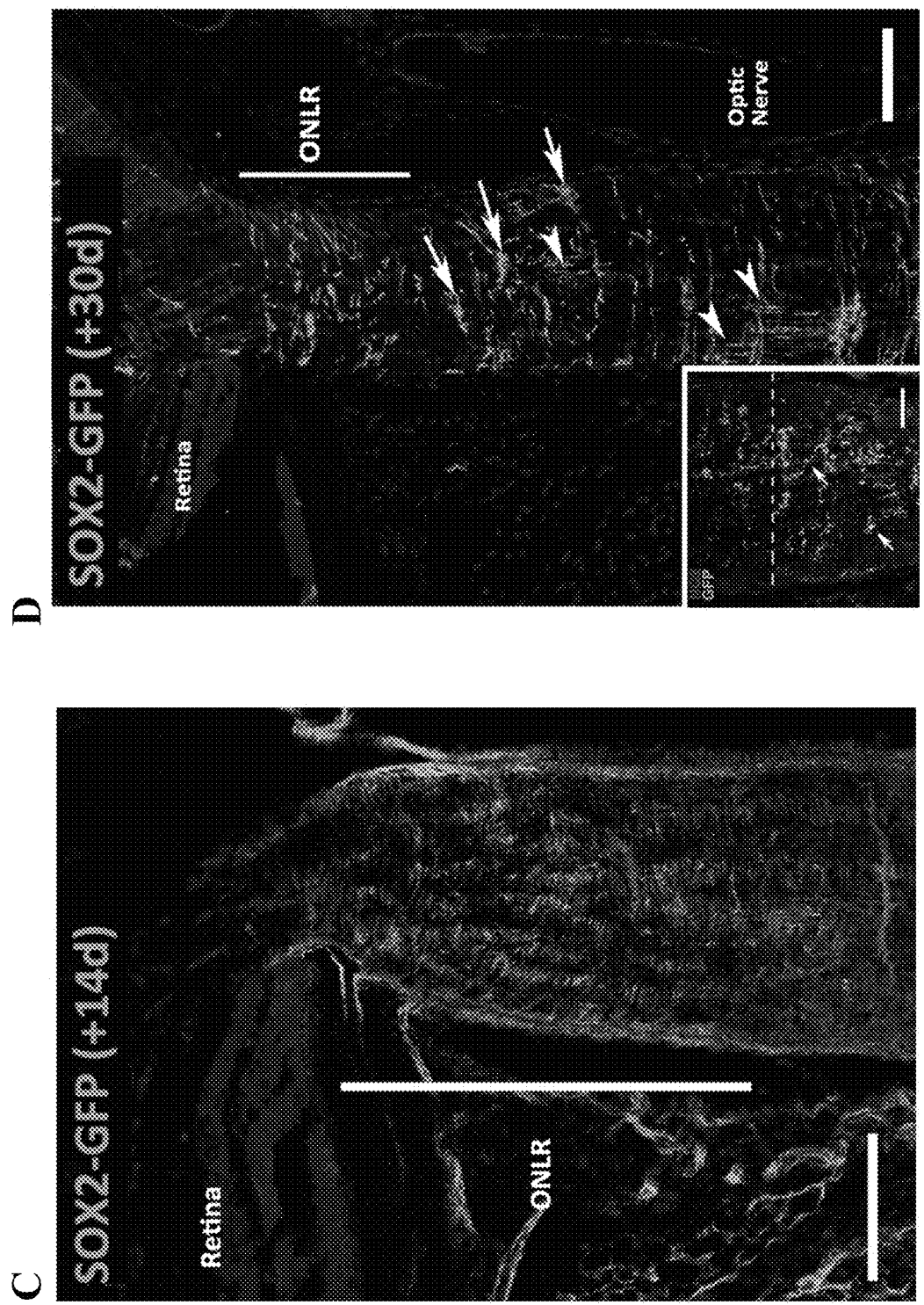
Figure 3:
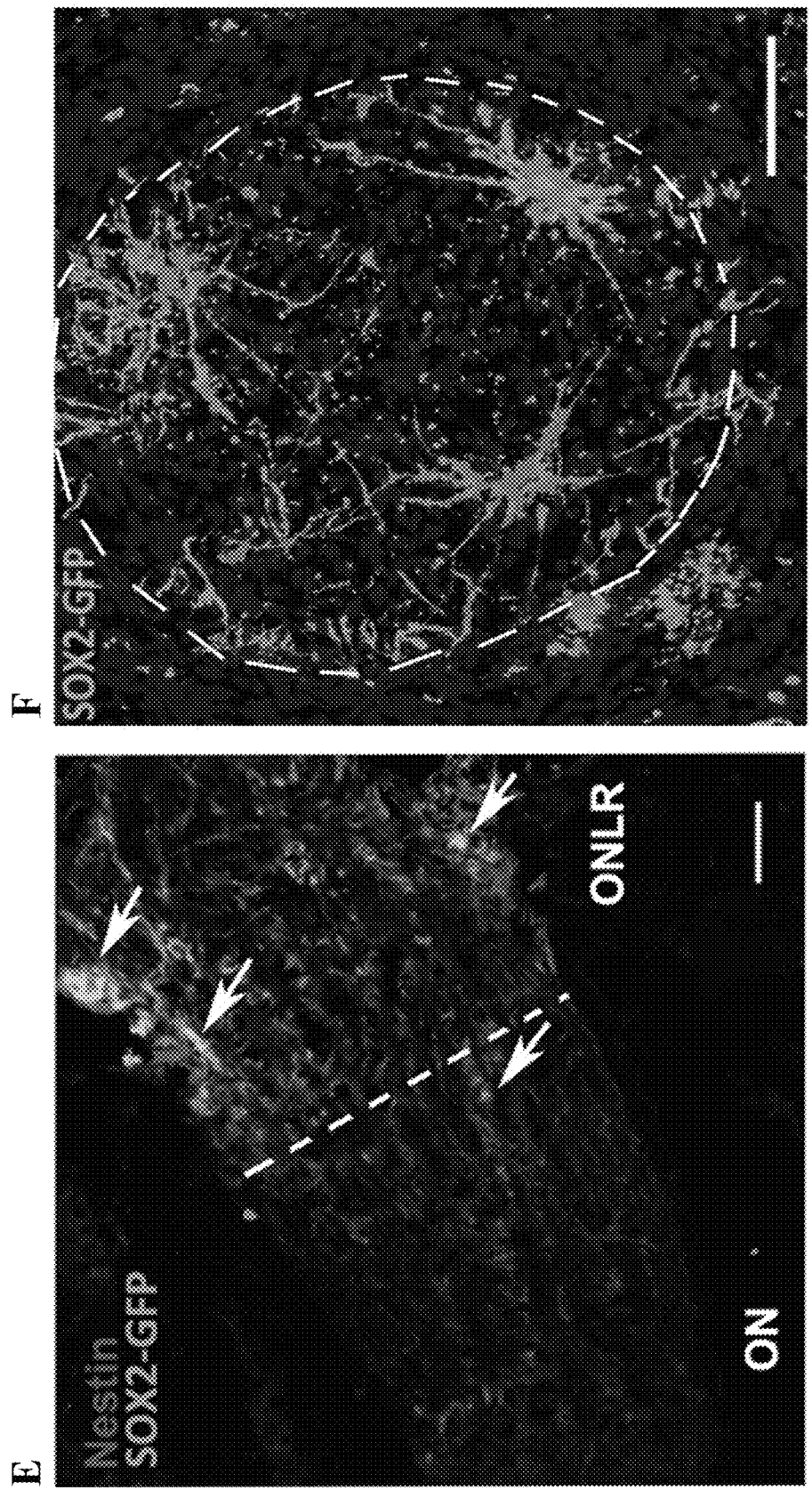
Figure 3:
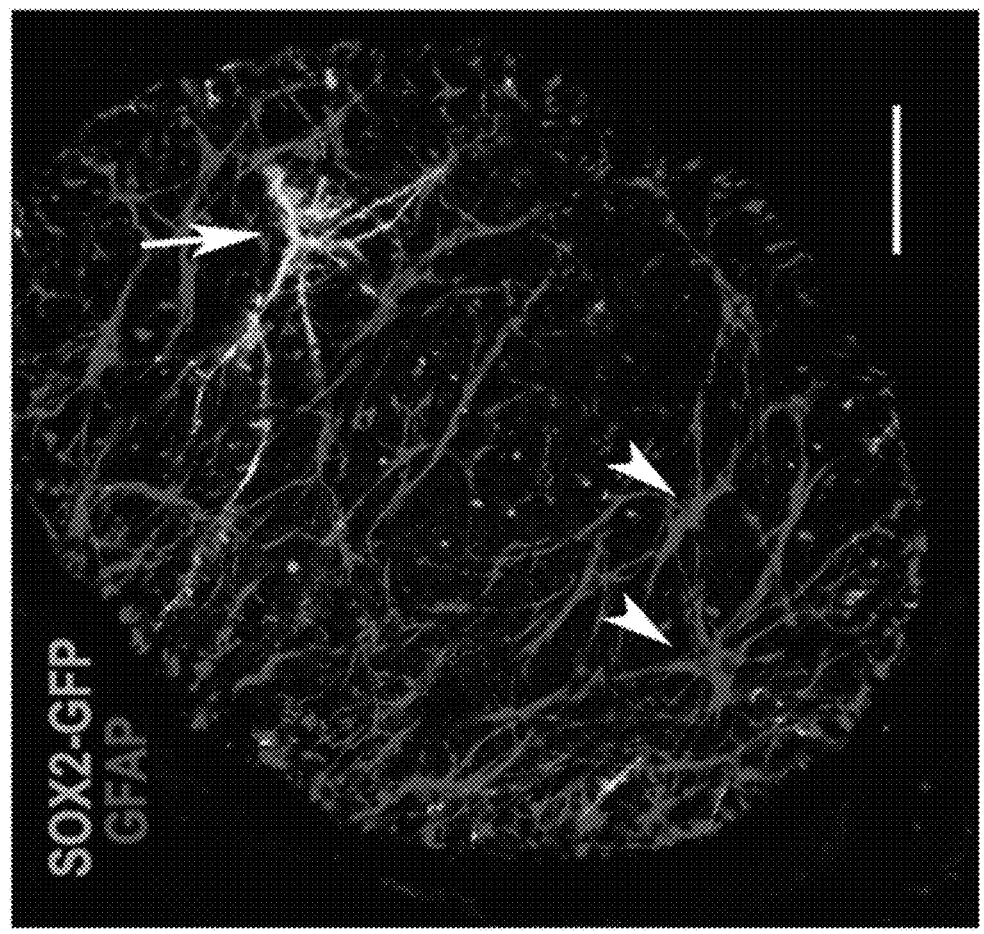

In one set of experiments, SOX2-Cre mice were crossed with a strain expressing td-Tomato reporter- and incorporating a FLOXed GFP-protein constructed in the ROSA26 locus (referred to as SOX2-GFP mice). SOX2-GFP mice constitutively express td-tomato, expressing GFP only following tamoxifen or 4-OH tamoxifen induction in SOX2(+) cells and their descendants (FIG. 3A). This enabled precise identification of the SOX2 expressing cells and their subsequent progeny post-injection.

Tamoxifen was administered to 19d PN animals (schematic, FIG. 3A). Robust GFP expression was seen in hippocampus 14d post-administration (FIG. 3B). SOX2-GFP expression 14d post-tamoxifen was localized to the ONLR but was indistinct (FIG. 3C). A 30d interval following injection was necessary to identify distinct cell patterns (FIG. 3D). Recombination efficiency in the lamina 30d post-induction was ~40%, based on the number of GFP(+) cells expressing on the td-Tomato background (Badea et al., 2003). 30d post-tamoxifen, ONLR-GFP expression was identifiable in processes transverse to the long axis of the nerve (3D: ONLR). In the ONLR, GFP co-localized with nestin (FIG. 3E; arrows), but not in the anterior ON. ONLR 30 μm thick cross section Z-stack reconstructions revealed individual large GFP(+) cells (FIG. 3F).

GFP expression was also present in the anterior ON in cells consistent with NG2 morphology at 30d (FIG. 3D; arrows). These cells co-expressed NG2 and GFP (3D inset; arrows). SOX2-driven GFP expression 30d post-induction was also present in structures parallel with the long axis of the ON, consistent with axon-myelinating segments (FIG. 3D; arrowheads), and co-localizing with antibody to myelin basic protein (MBP: data not shown). Below the ONLR, GFAP(+)/GFP(+) cells were identified (FIG. 3G; arrow) as well as GFP (−)/GFAP(+) cells consistent with astrocytic morphology (FIG. 3G; arrowheads). The data supports the hypothesis that ONLR-SOX2/nestin(+) NPCs can give rise postnatally to both ON-NG2(+) OPCs, as well as directly to astrocytes. These differentiating daughter cells can migrate into the anterior ON, ultimately generating mature glial forms. This functional strategy enables focused ON anterior myelination and astrocyte production during the late postnatal ON growth phase. Resident SOX2(+)/NG2(+) cells enables oligodendrocyte replacement in the mature animal, as previously noted (Kang et al., 2010).

The effect of postnatal SOX2-NPC ablation in the ONLR was examined using transgenic animals constructed with the ER2-SOX2-Cre transgene and the FLOXed diphtheria toxin A (DTA) protein in the ROSA26 locus (referred to as SOX2-DTA animals). Cre-based recombination induces DTA protein (Saito et al., 2001), enabling selective deletion of SOX2-expressing cells following tamoxifen administration. SOX2-DTA animals thus provide a highly sensitive tool for analyzing effects of ONLR-SOX2(+) cell loss, since DTA ablates them. Local administration of 4-hydroxytamoxifen (4OHT) via retrobulbar injection, enabled selective elimination of SOX2-expressing cells in one eye (Bernstein et al, manuscript in preparation). Local administration efficacy was confirmed using SOX2-GFP animals (FIG. 3D-F).

Figure 4:
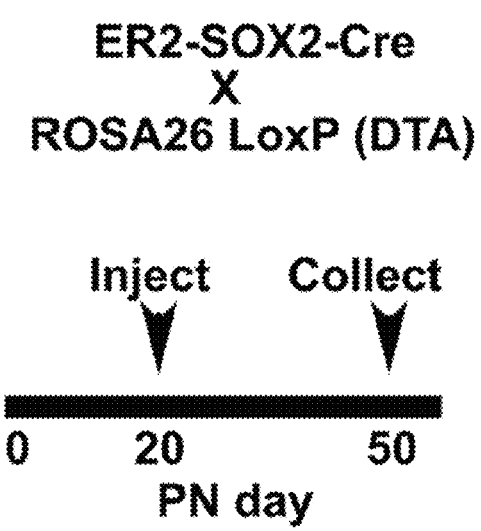
FIG. 4. Late postnatal deletion of SOX2(+)/Nestin (+) ONLR-NPCs affects postnatal ON growth and myelination. A. Transgenic cross and induction schedule. SOX2-DTA animals treated 19d PN with either vehicle or 4OHT, and analyzed 14d post-treatment (33d). B and C. Gross ON appearance (Vehicle: V and Experimental: 4OHT) 14d post-treatment. 4OHT-treated ONs are thinner (arrowheads), and the contralateral post-chiasmal optic tract, (axons of the treated nerve) is reduced (arrow), compared with vehicle treated ONs. D-G: Immunohisto-chemical analysis: Loss of SOX2 and nestin expression in the ONLR of 4OHT-induced SOX2-DTA nerves. D and E: Nestin expression. Reduced nestin immunoreactivity in 4OHT treated nerves (E); compare with vehicle, D. Low power magnification (Insets in D and E) indicate the relative level of nestin expression in the anterior ONs. F and G: SOX2 expression. Vehicle treated nerve (F): left panel; 4OHT treated nerve (G) right panel. Reduced SOX2(+) nuclear staining in the 4OHT treated nerve. Inset, G: SOX2(+) quantification in the ONLR of WT (white bar) vs 4OHT treated nerves (Black bar); results±sem; n=3 animals/group. H. ON ultrastructural analysis-strategy schematic after vehicle or 4OHT-DTA induction in SOX2-DTA double mutants. Letters indicate the analyzed ON regions. I-L: TEM ultrastructure 14d post-induction. I. Anterior ON, 4OHT treated (1.5 mm from the eye). J. Distal ON, 4OHT treated (5 mm from the eye). L: Anterior ON, vehicle treated. K. Distal ON, vehicle treated. Axons in vehicle treated anterior and distal ON regions are closely packed, with dense myelination. Axons in the anterior 4OHT treated ONs have reduced packing density, and increased extracellular vesicles, compared to vehicle ONs and more distal portion of the same nerve. The axon anterior segments have reduced myelination, compared to more distal segments. Scale bar in I: 500 nm. M. Mean axon diameter quantification of anterior and posterior ON segments from Vehicle (white bars) and 4OHT treated (black bars) nerves. ±sd. N. Mean G-ratios of vehicle (white bars) and 4OHT treated (black bars). ±sem; n=3 animals. A statistically significant increase in the G-ratio of 4OHT treated nerves occur in the anterior ON in animals treated at 19d postnatally, after local injection of 5 ul of vehicle (V) or 4OHT. Data from 6 random 164 um$^2$ fields from each nerve region. O. Individual G-ratios for the different axon size classes from vehicle (white bars) and 4-OHT treated (black bars) nerves. There was an increase in the G-ratio for all size classes of 4-OHT treated ONs, and a loss of the smallest axon diameter class in the anterior segment of 4-OHT treated nerves (absence of black bar). +/−sd.
Figure 4:
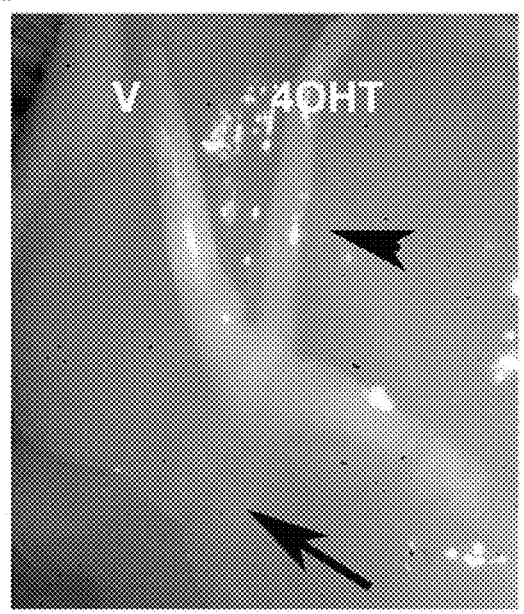
Figure 4:
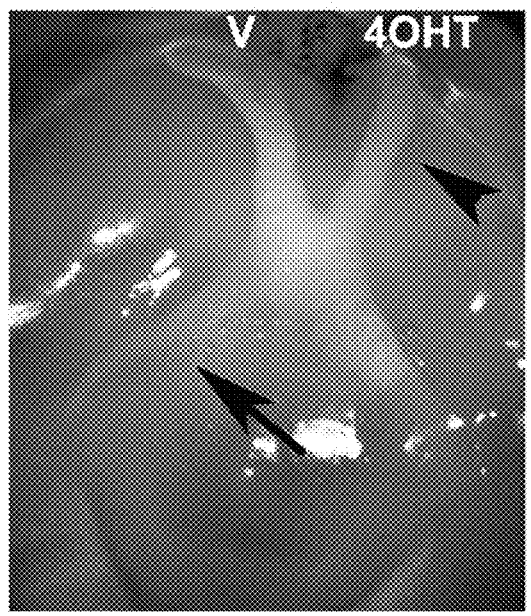
Figure 4:
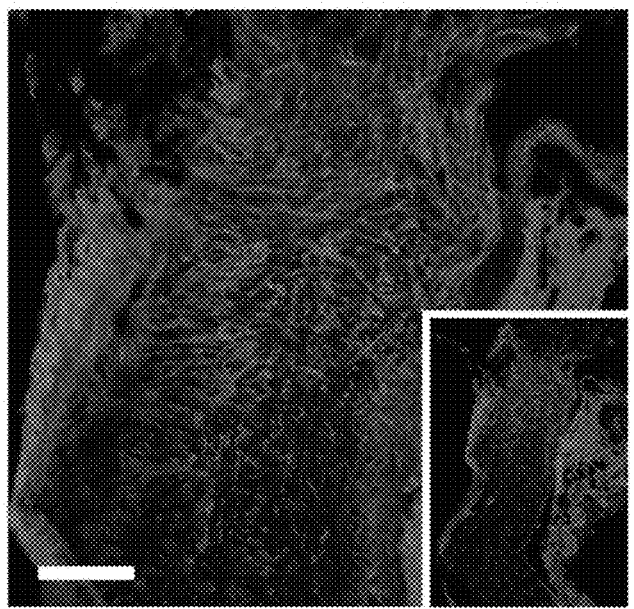
Figure 4:
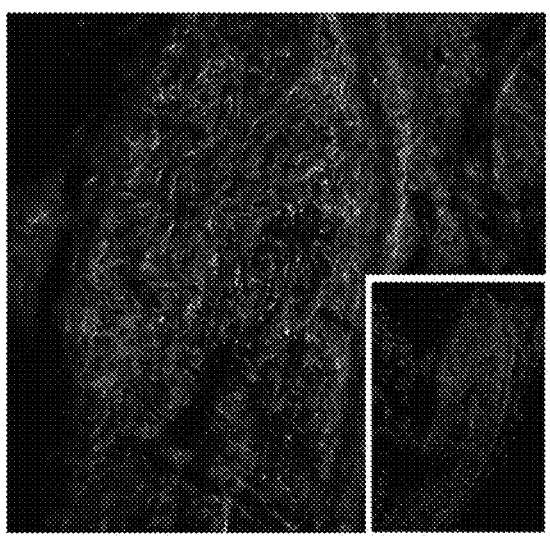
Figure 4:
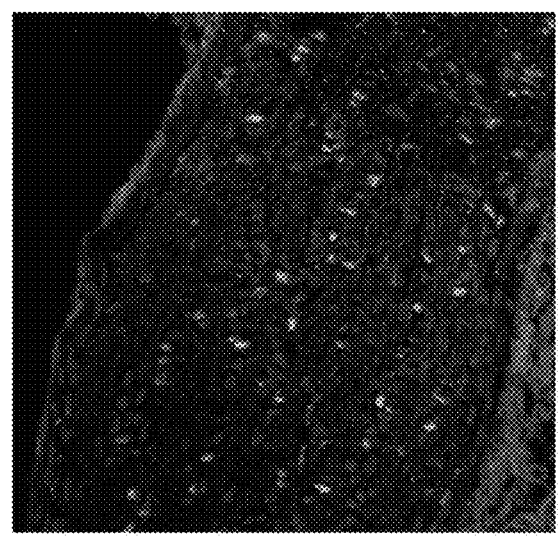
Figure 4:
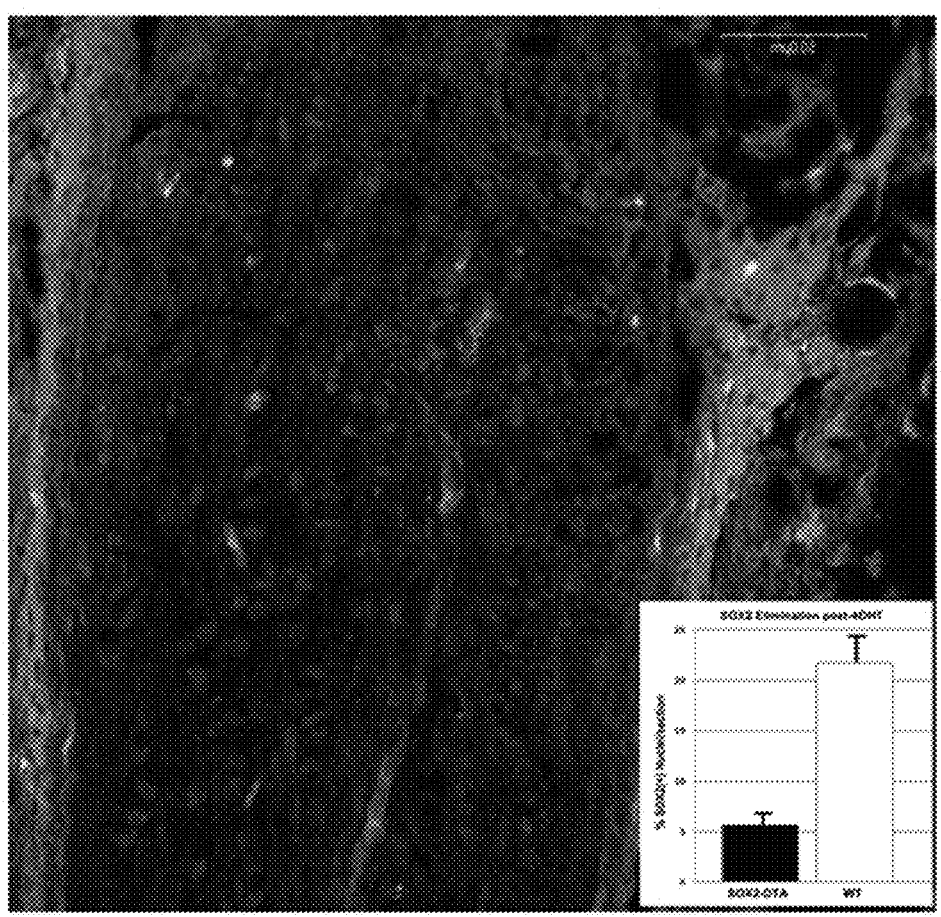
Figure 4:
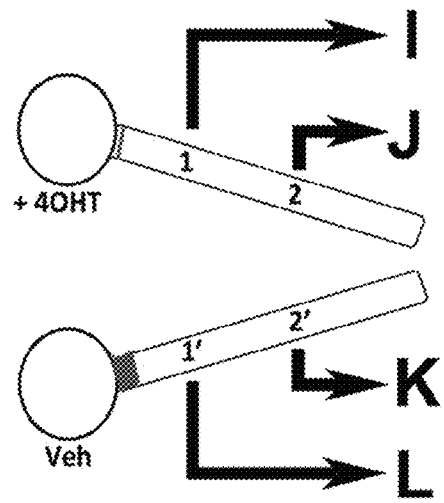
Figure 4:
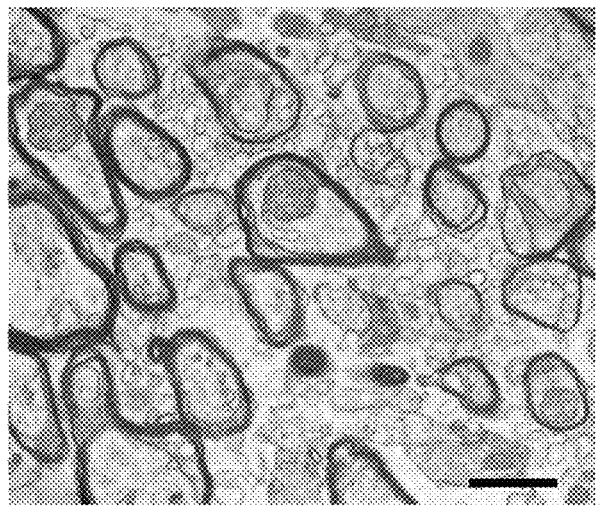
Figure 4:
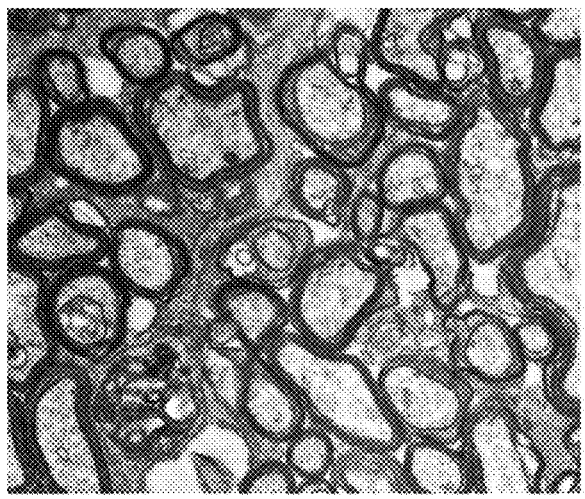
Figure 4:
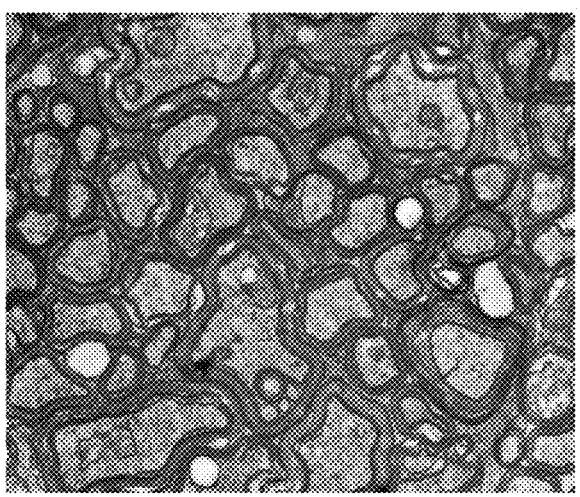
Figure 4:
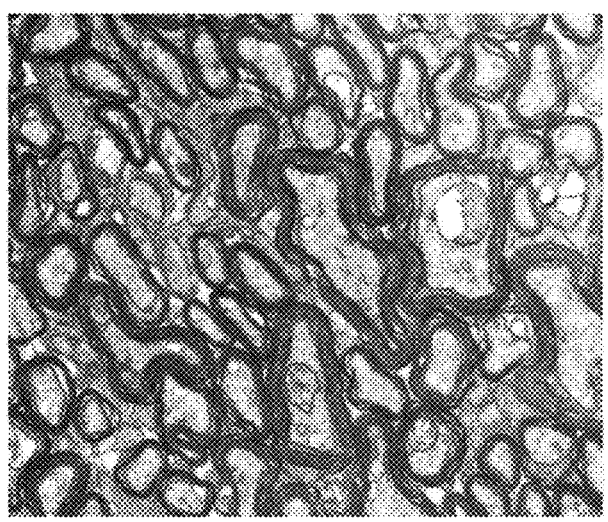
Figure 4:
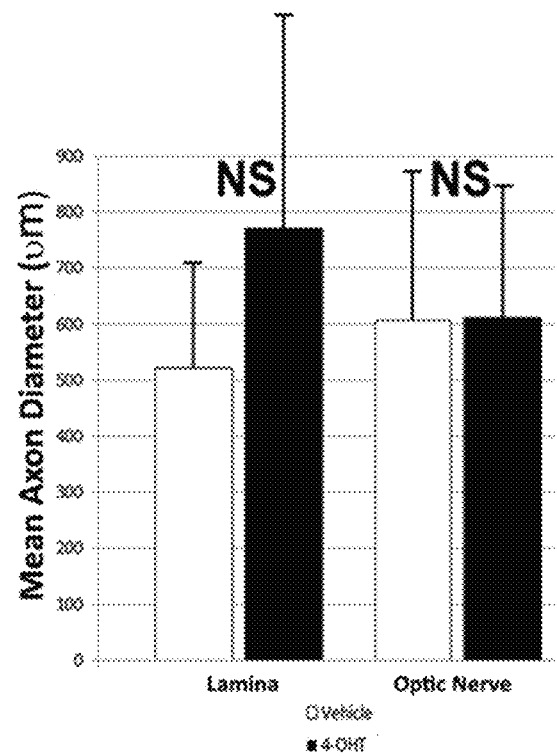
Figure 4:
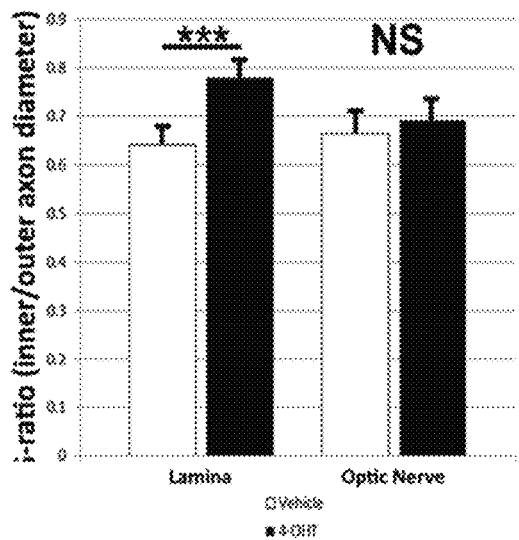
Figure 4:
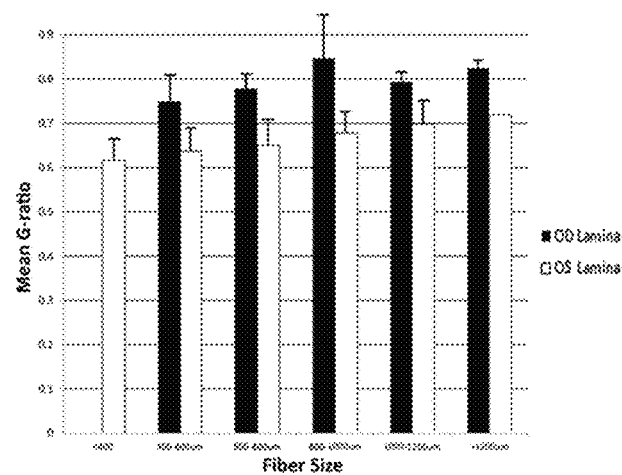

ON morphology was compared between 4OHT and contralateral vehicle (Kolliphor) treated animals 14d and 30d post-administration. Ocular tissues were compared for size and appearance (FIG. 4A). Post-fixed tissues were evaluated for ONLR SOX2—(see FIGS. 4F and G) and nestin-(FIGS. 4D and E) expression. ON ultrastructure was examined using transmission electron microscopy (TEM) (FIGS. 4I and L).

Nerves of SOX2-DTA animals given vehicle were normal appearing (see FIGS. 4B and C: 'V'), with a normal contralateral optic tract (FIGS. 4B and C: arrow). In contrast, 4OHT-treated ONs 14d post-induction were hypoplastic (FIGS. 4B and C: compare V and 4OHT: arrowheads indicate nerve of the 4OHT-treated side). The optic tracts associated with 4OHT-treated nerves also had a reduced appearance, compared with vehicle-treated ON tracts (FIGS. 4B and C: arrow).

DTA-induced NPC cell loss post-4OHT was assessed in 33d PN animals. There was selective loss of nestin and SOX2 signal in 4OHT treated ONLR- and ONs (FIG. 4E; nestin and G; SOX2), compared with vehicle-treated nerves (FIG. 4D; nestin and F; SOX2). Thus, deletion of SOX2(+) ONLR cells drastically reduced anterior nestin expression and altered normal ONLR structure.

Quantification of SOX2 nuclear expression at 4d post-4OHT administration revealed a loss of over ⅔ of SOX2 nuclei in the ONLR compartment, compared with WT animals (FIG. 4G inset: 6.9±1.9% SOX2(+) nuclei in the ONLR of 4-OHT treated SOX2-DTA animals v. 21.8±4.9% in the ONLR of WT; n=3 animals group, ±sem). These data suggest that the loss of SOX2(+) nuclei post-induction is not due simply to tamoxifen-related drug toxicity or retrobulbar injection, but rather a loss of NPCs.

The ONLR extends ~300 μm from the 60d PN mouse eye (Wang et al., 2017 and FIG. 1). It was hypothesized that the postnatal retinal ganglion cell (RGC) axon grows unidirectionally from the unmyelinated region, with postnatal myelination supplied by glia derived from ONLR-NPCs. With this pattern, anterior myelination in the growing ON would occur focally as a distinct zone directly below the ONLR, as unmyelinated axons emerge from the lamina. To examine this, myelination patterns were compared in the anterior- and mid-ON from postnatal SOX2-DTA animals, in which active ON growth was still occurring (FIG. 4H-K). Animals were treated at 19d PN, and evaluated at 33d PN (14d post-treatment). ONs were ultrastructurally analyzed using TEM at their anterior-(1.5-2 mm from eye) and distal (5 mm from the eye) segments (schematic, FIG. 4H). WT animals injected either with vehicle or 4OHT showed no gross alterations or significant axonal loss (data not shown).

Ultrastructural results in nerves of SOX2-DTA animals treated with vehicle were similar to those of WT animals (FIG. 4L, anterior, and 4K. distal segments). Relative myelin thickness to axon diameter (G-ratio) was unchanged, and similar at both anterior and distal segments (FIG. 4N, white bars). In contrast, 4OHT-treated nerves of SOX2-DTA animals revealed axonal hypomyelination in the anterior ON segment, with a corresponding increase in the G-ratio (FIG. 4N, black bars: compare anterior ON (lamina) and distal (optic nerve), along with axonal loss and reduced packing density (FIG. 4I), compared to vehicle treated anterior nerve from the same animal (compare FIG. 4L, vehicle, with 4J, 4-OHT treated). Comparing mean relative axon size in the anterior and distal segments, a trend toward a larger mean axon diameter was seen in anterior ON segments (FIG. 4M; 522±190 nm for vehicle v. 771±382 nm for 4OHT), due to a loss of the smallest axon class (<400 nm diameter) in 4OHT treated nerves (absence of a black bar in the <400 um size class in the individual G-ratio axon size graph in FIG. 4O). This suggests that either small axons are selectively lost with 4OHT treatment, or there is an increase in the relative diameter of the smallest axons, possibly due to swelling from intra-axonal fluid accumulation. The latter explanation is most likely since a comparison of relative mean axon diameter from the distal ON segments of both treatment groups revealed little, if any differences in mean axonal diameter (607±261 nm for vehicle v. 612±228 nm for 4OHT) and a similar packing density. In distal ON segments of 4-OHT-treated nerves, (FIG. 4J), myelination was similar to that of vehicle-treated nerves (compare 4J with 4K; vehicle).

The G-ratio was calculated for each axon size class in Vehicle and 4-OHT treated nerves (FIG. 4O). There was an increase in the G-ratio in every axon size class in 4-OHT treated nerves, an exception being the loss of the smallest diameter axons (<400 nm in diameter) in 4-OHT treated ON. 4-OHT treatment resulted in a mean increase in the G-ratio, indicating a relative thinning of the myelin sheaths of axons in the anterior region (FIG. 4N; Anterior ON: 4OHT=0.79±0.04 (sd) v. Vehicle=0.67±0.03 (sd)), compared with vehicle treated nerves from the same animal (two tailed t-test; $p<0.001$). This was not apparent in the distal segment, where the mean distal ON G-ratio for 4OHT- and vehicle-treated nerves were similar (FIG. 4N: ON. 4OHT; 0.69±0.08 v. vehicle; 0.66±0.09) from the same animal(s).

The anterior ON of 4OHT-treated nerves also had decreased axon packing density (increased distance between axons) and increased vacuoles were observed in the anterior portion of 4OHT treated-compared with vehicle-treated nerves from the same animal (compare axonal packing in FIG. 4I; 4OHT treated, with 4L; vehicle treated).

Despite anterior ON hypomyelination, distal axon segment myelination was similar in both 4OHT- and vehicle-treated nerves (compare FIG. 4J, 4OHT-treated and 4L, vehicle-treated, respectively).

Randomized axonal counts from six fields revealed a mean 40.5% loss in 4OHT treated ONs, (mean 126±27.6 axons/field in vehicle v. 76±9.9 axons in 4OHT per 165 um$^2$ field) from SOX2-DTA animals (white bars), compared with vehicle treated eyes ($p<0.05$, Fisher exact test). These results reveal that selective postnatal deletion of SOX2(+)/nestin(+) ONLR-NPCs during active ON growth results in a pattern of regional loss of anterior myelination. These results are consistent with the hypothesis that, in addition to axonal loss, ONLR-NPCs contribute to progressive development and migration of newly formed oligodendrocytes and astrocytes in the growing postnatal ON.

E. Age-Related Quantitative Changes in NPCs in Rodent and Human ONLR

Adult NPC numbers decline during aging (Encinas et al., 2011), and ONLR-NPC decline may be associated with the aged ON's reduced reparative ability (Malik et al., 2014). Age-related ONLR-NPC-associated changes were quantified in mice by two approaches: 1) immunohistochemical analysis and quantification of SOX2 nuclei in the ONLR of 1, 7 and 24 m/o mice (FIG. 5A-C); 2) nestin mRNA quantification in 1, 6 and 12 m/o mice using rq-PCR (n=6 animals/prep) (FIG. 5D).

Figure 5:
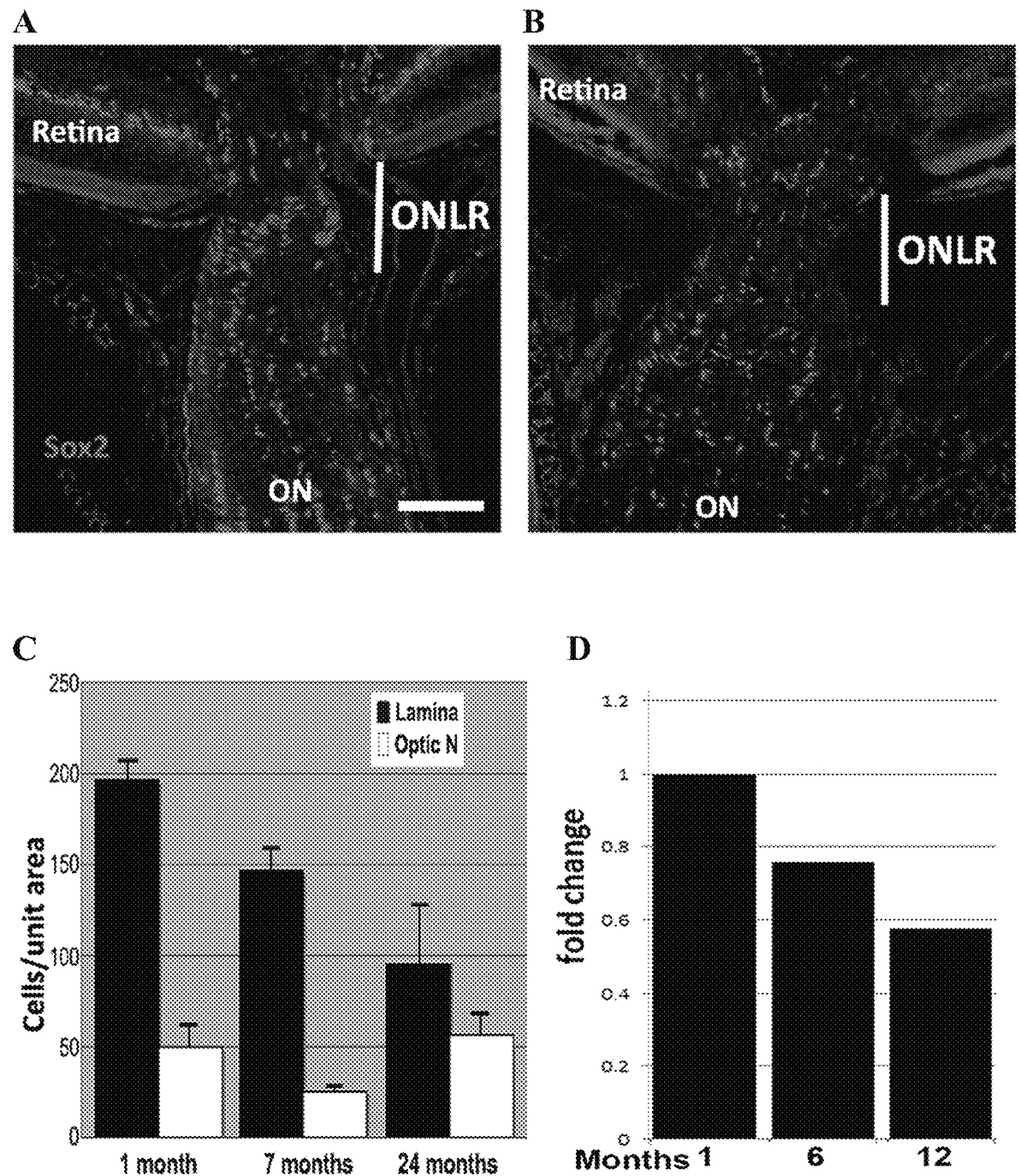
FIG. 5. Age-related NPC depletion in mouse and human ONLR, and neurosphere development from human donors. A. SOX2 nuclear expression in 7 mo mouse ONLR. SOX2 (+) nuclei are present in nests within the ONLR, and in high numbers in the anterior ON. B. SOX2 nuclear expression in a 2 y (24 mo) mouse ONLR. There are fewer SOX2(+) nuclei in both ONLR and anterior ON, compared with 7 mo animals. C. SOX2 nuclear quantification in ONLR and ON during aging. SOX2 nuclei decline twofold from 1 mo-2 y (black bars) while SOX2 nuclear numbers in distal ON (white bars) remain relatively constant during this time (n=6 nerves/group; Data±sem). D. rq-PCR analysis of nestin mRNA expression in mouse ONLR (n=6 nerves pooled/group). Nestin mRNA levels decline >40% in the first year of life. Only one pooled prep was prepared for each age group: there are no error bars. E-H: Analysis of human ONLR-nestin and −SOX2 expression, with SOX2 immunostaining (green) and Nestin (red). E. 7 month fetal ONLR. Strong SOX2 nuclear staining and nestin expression is concentrated in the ONLR. F. 9 y/o ONLR. Strong filamentous nestin staining is indicated (arrows). G. 40 y/o. Reduced nestin expression, but SOX2(+) nuclei are still numerous. H. 50 y/o. Reduced filamentous nestin expression, with remaining nestin present almost exclusively in the vasculature, and greatly reduced SOX2(+) nuclei. Inset: 71 y/o ONLR. The elderly ONLR reveals both a total lack of filamentous nestin and an absence of SOX2(+) nuclei. I. Densitometric analysis of age-related human ONLR nestin expression. Nestin expression declines linearly from 9 y/o to 45 y/o, with severe loss in individuals >50 y of age. The inset shows donor history. J. Human ONLR neurosphere formation (33 y/o donor). K. SOX2/nestin expression in human neurospheres generated from 3$^{rd}$ passage ONLR culture (33 y/o individual). K. SOX2 (green)/nestin (red) Immunolabeling of human neurosphere from culture shown in J. Individual cells express both SOX2 and nestin L. Nestin (red)/GFAP (green) expression in human neurosphere. Nestin and GFAP colocalize in individual cells. Scale bar: 100 um.
Figure 5:
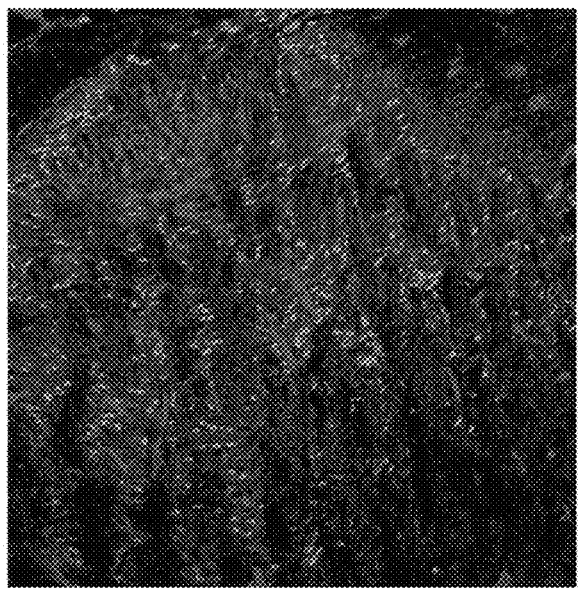
Figure 5:
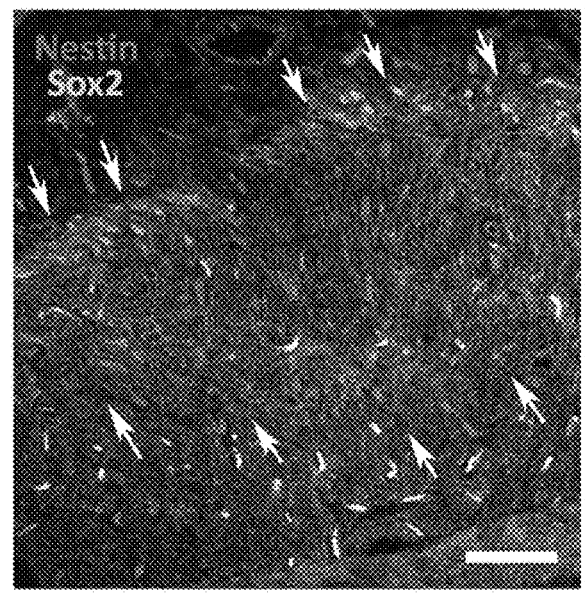
Figure 5:
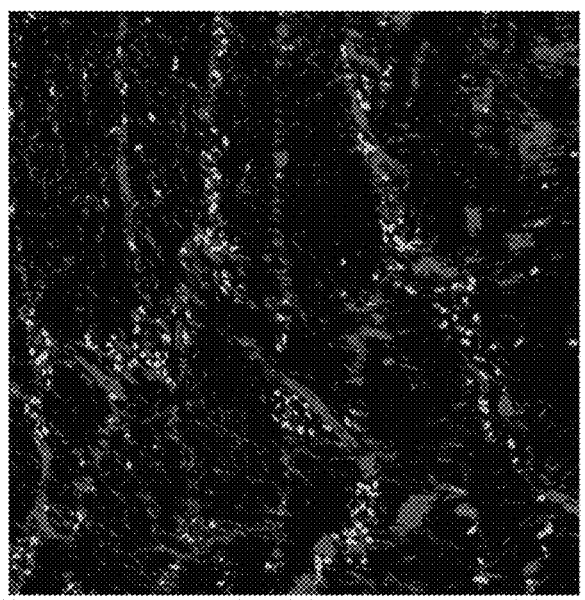
Figure 5:
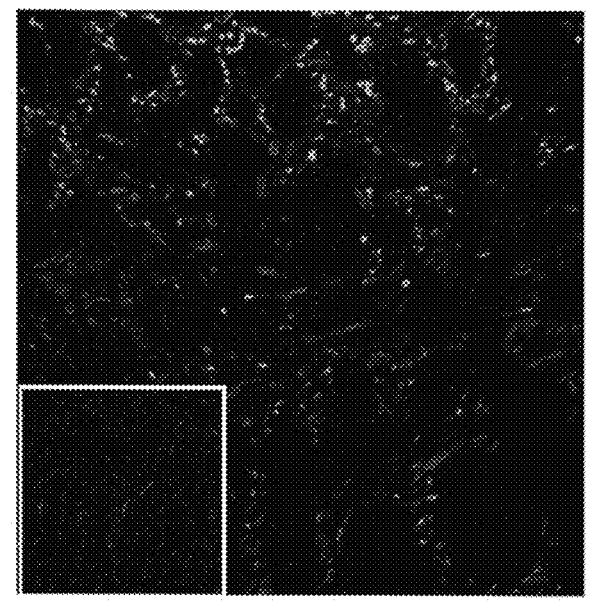
Figure 5:
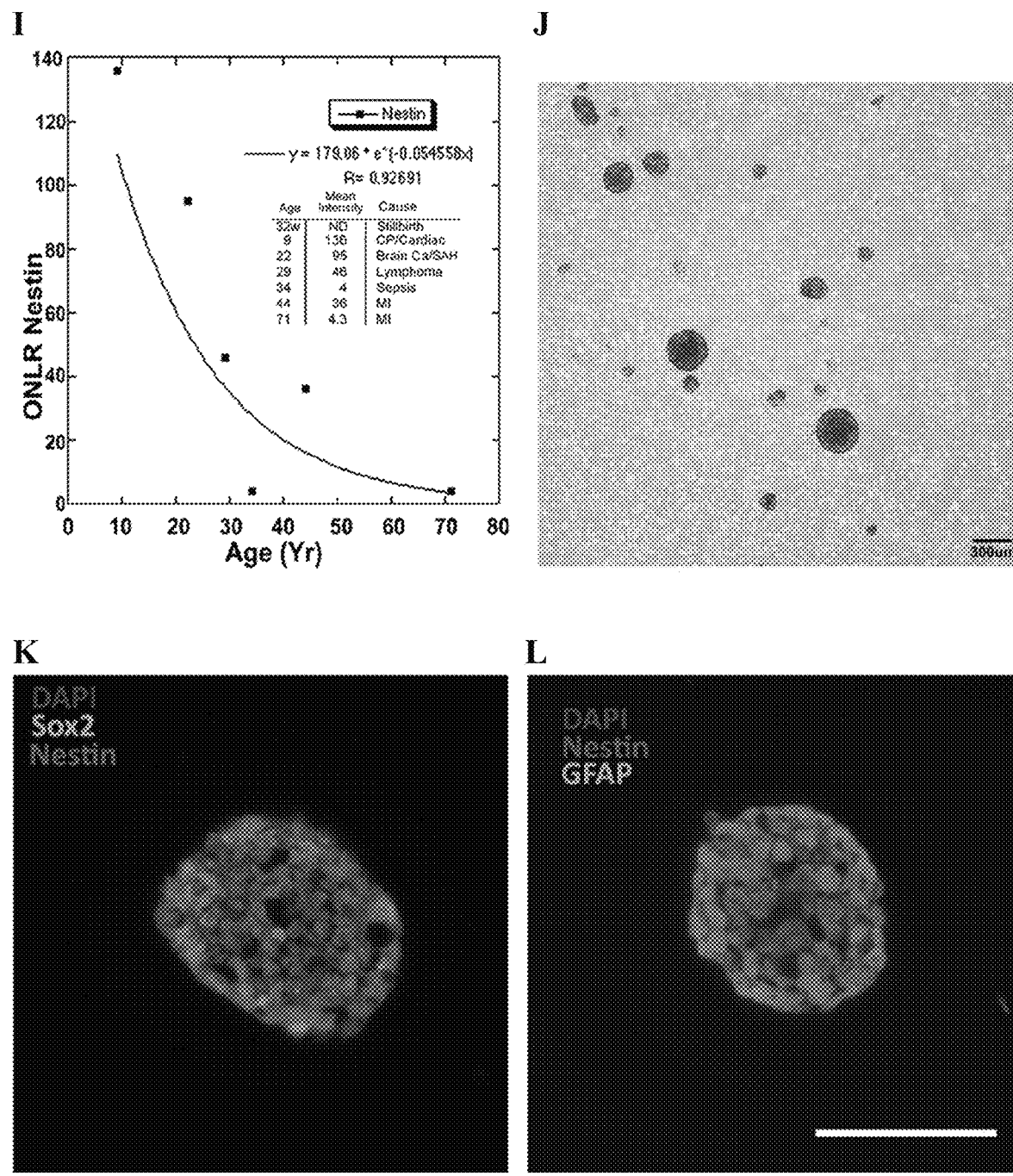

For 1), SOX2(+) nuclear numbers in ONLR sections were compared using equivalent relative surface area per region (45,000 um$^2$×3 sections/animal; n=3 animals FIG. 5C). ONLR-SOX2(+) nuclear numbers declined 73% in 24 m/o animals, compared with 1 m/o animals (FIG. 5C, black bars: 53±36 v. 197±10; SEM; n=6 nerves/group). Interestingly, ONLR has a greater number of SOX2(+) nuclei than distal ON, but the number of SOX2(+) cells in distal ON remains relatively constant during aging (FIG. 5C; white bars). Similarly, for 2), mouse ONLR nestin mRNA levels declined by 56% by 12 m/o, compared with nestin mRNA levels seen in 1 m/o animals (FIG. 5D; compare 1 m/o and 12 m/o). ONLR thus exhibits an age-dependent decline in both NPC-associated proteins, suggesting that ONLR-NPCs diminish with age.

F. The Human ONLR Contains an Age-Depletable NPC Niche

The primate laminar structure is more elaborate than rodents (Anderson and Hoyt, 1969), but the pattern of overall ONLR organization is similar in both phylogenetic families (Albrecht, 2008). Young human ONLRs strongly express filamentary nestin and possess abundant SOX2(+) nuclei, (FIG. 5A, 7 m/o fetal ONLR and 5B, 9 y/o donors). Younger donors generally showed increased SOX2(+) nuclear expression compared with tissue from older donors. However, young donor tissues obtained with prolonged times (>24 hours) from demise until preservation showed reduced SOX2 signal (compare 5F, 9 y/o and G, 40 y/o). This preservation time-dependent decline of SOX2 expression resulted in variability between donors of similar ages.

Nestin expression was found to be less dependent on time to preservation, possibly because structural proteins are more stable than nuclear factors. Densitometric quantification of age-associated changes in donor human ONLR nestin expression is shown in FIG. 5E-H. ONLR-nestin expression declined precipitously with donor age (compare signals from youngest donors: 7 mo fetal in 5E and 9 y/o in 5F, with reduced signal from tissues of intermediate age donors 40 y/o (FIG. 5G) and 50 y/o (FIG. 5H)). Filamentous nestin was absent in the ONLR of the oldest donors (5H inset). Human ONLR-nestin expression declined >90% by age 60 y (linear regression statistic, r=0.92; FIG. 5I). Tissue from elderly donors, even those having minimal time from collection to preservation contained few, if any, ONLR-SOX2(+) nuclei or nestin. These data suggest that the human ONLR, like mice, contains an age-depletable cell niche of ONLR-NPCs.

To confirm the presence of human ONLR-NPCs, ONLRs were dissociated from freshly obtained human surgical specimens (approved by the UMB-institutional review board (IRB)). Human cultures utilized media conditions identical to those used for mouse ONLR cultivation. Initial growth on adherent plates with Matrigel-supplemented medium generated mixed cultures, similar to those seen in rodent. Cells with a bipolar morphology were a prominent feature in early passage cultures grown on adherent plates. Neurospheres were generated when cells were regrown in low adherence conditions (FIG. 5J). Immunostaining of passage 3 human ONLR-neurospheres yielded cells co-expressing SOX2, GFAP and nestin, consistent with NPC characteristics (FIGS. 5K and 5L).

G. ONLR Stem Cell Niche Gene Expression

The ONLR contains a neural stem cell niche. To determine whether the ONLR stem cell niche plays a role in the prevention or resistance to glaucoma, gene expression of cells from the niche was examined. Fresh (<1 hr old) tissue from young (4-6 year old) male and female rhesus macaque monkeys that previously had no ocular disease or conditions that would alter ocular gene expression was isolated. This included the eye and attached optic nerve. This tissue was kept on ice until further dissection. The retina, the optic nerve lamina containing the neural stem cell niche (first 0.5 cm of the optic nerve, containing the optic nerve head), and distal optic nerve tissues (>1 cm behind the laminar region) was dissected. These tissues were isolated from the original tissue and stored at −80° C. until use.

Total RNA was isolated using a sequential purification via RNA Bee (guanidinium thiocyanate-phenol), followed by resuspension in solution provided in the Qiaprep RNA isolation kit. The resuspended RNA was re-isolated through Qiaprep RNA isolation columns, yielding ultrapure total RNA. Total RNA was used for sequence analysis. Two independent analyses were performed. First, RNA was utilized from one sample of lamina and one sample of optic nerve. These RNA samples were sent to the Yale sequencing facility for further processing into complementary strand RNA and illumina RNA sequencing and sequence comparison using standard sequence analysis procedures. Total RNA prepared from a new lamina tissue (the second animal), as well as total RNA from retina from two animals and two optic nerves were sent to the University of Maryland, Baltimore, Biocore for further processing into complementary strand DNA and illumina RNA sequencing. Thus, there were a total of two retina samples, two lamina samples and two optic nerve samples used for sequencing. Analysis was performed using the Qiagen sequence ingenuity program analysis (IPA) analysis software package. Gene expression was compared by combining CPM sequence results from retina and optic nerve, and related to lamina CPM, using the following formula:

$$\frac{\text{Lamina } CPM \text{ results}}{\text{Retina1 } CPM + \text{Retina2 } CPM + \text{Optic Nerve}} = \text{Laminar niche/surrounding tissue ratio}$$

Results from genes associated with growth factors were identified and then grouped together. The growth factors with Lamina/Retina +Optic Nerve ratios >3.0 were further identified. Two groups of genes were thus established: 1) total gene comparison, and 2) growth-factor associated genes that are differentially expressed at higher levels in the lamina stem cell niche.

Genes with laminar niche/surrounding tissue ratios ≥3.0 and Laminar CPM counts ≥90 were identified. The chromosomal localization of each gene was confirmed using Genecards (see the website having the URL ending with genecards.org/), and a Google search was performed to determine whether this chromosomal location was reported to be associated with the optic nerve disease glaucoma (either primary open-angle glaucoma, juvenile open-angle glaucoma, normal tension glaucoma, or congenital glaucoma). The results presented in Table 7 are strong evidence that the ONLR neural stem cell niche expresses genes that are responsible for resistance to developing glaucoma, and also identify the growth factors and related proteins that are involved in this resistance. The products of these genes can be either prepared as the active peptide, or the whole protein, and administered as a cocktail of the individual factors, such as in the artificial ONLR-NPC extracts of the invention defined herein.

TABLE 7

ONLR stem cell niche gene expression

| name | 233_ret | 240_ret | 241_lam | 242_on | gene | Ratio = Lam/Ret + ON | Name |
| --- | --- | --- | --- | --- | --- | --- | --- |
| ENSMMUG00000005603 | 0 | 0 | 90 | 1 | UCMA | 90 | Upper Zone of Growth Plate and Cartilage Matrix Associated Protein |
| ENSMMUG00000005068 | 1 | 0 | 94 | 1 | GFI1 | 62.66667 | Growth Factor Independent 1 Transcriptional Repressor |
| ENSMMUG00000002875 | 5 | 3 | 194 | 2 | FGF14 | 32.33333 | Fibroblast Growth Factor 14 |
| ENSMMUG00000004919 | 0 | 0 | 95 | 3 | FGFR4 | 31.66667 | Fibroblast Growth Factor Receptor 4 |
| ENSMMUG00000000896 | 6 | 13 | 534 | 10 | TGFB1I1 | 27.38462 | Transforming growth factor beta-1-induced transcript 1 protein |
| ENSMMUG00000005353 | 2 | 0 | 92 | 3 | PDGFD | 23 | Platelet Derived Growth Factor D/Spinal Cord-Derived Growth Factor B |
| ENSMMUG00000002909 | 0 | 3 | 148 | 5 | PGF | 22.76923 | Placental Growth Factor |
| ENSMMUG00000003468 | 5 | 3 | 139 | 5 | GADD45B | 15.44444 | Growth arrest and DNA damage-inducible protein GADD45 beta |
| ENSMMUG00000000332 | 10 | 33 | 596 | 18 | TGFBI | 15.08861 | Transforming growth factor beta-1 proprotein: Both latency and factors |
| ENSMMUG00000001153 | 0 | 1 | 292 | 21 | PDGFRL | 13.5814 | Platelet-derived growth factor receptor-like protein |
| ENSMMUG00000002235 | 25 | 24 | 219 | 0 | IGF1 | 8.938776 | Insulin growth factor-1 |
| ENSMMUG00000003748 | 2 | 5 | 137 | 14 | VEGFC | 7.828571 | Vascular Endothelial Growth Factor C |
| ENSMMUG00000000401 | 59 | 81 | 594 | 28 | GAS8 | 6.061224 | Dynein regulatory complex subunit 4 |

TABLE 7-continued

ONLR stem cell niche gene expression

| | | | | | | | |
|---|---|---|---|---|---|---|---|
| ENSMMUG00000001336 | 13 | 3 | 235 | 40 | GHR | 4.895833 | Growth Hormone Receptor |
| ENSMMUG00000004594 | 22 | 25 | 128 | 11 | CGRRF1 | 3.710145 | Cell Growth Regulator With Ring Finger Domain 1 |
| ENSMMUG00000000949 | 61 | 41 | 336 | 56 | FGF12 | 3.140187 | Fibroblast growth factor 12 |

| name | Chromosome | Disease linkage |
|---|---|---|
| ENSMMUG00000005603 | 10p13 | Normal Tension glaucoma |
| ENSMMUG00000005068 | 1p22.2 | Primary open-angle glaucoma (POAG) |
| ENSMMUG00000002875 | 13q33.1 | Pseudoexfoliative glaucoma |
| ENSMMUG00000004919 | 5q35.2 | POAG |
| ENSMMUG00000000896 | 16p11.2 | Congenital glaucoma |
| ENSMMUG00000005353 | 11q22.3 | POAG |
| ENSMMUG00000002909 | 14q24.3 | Primary congenital glaucoma (GLC3C) |
| ENSMMUG00000003468 | 19p13.3 | GLC10 glaucoma gene site |
| ENSMMUG00000000332 | 19q13.2 | POAG |
| ENSMMUG00000001153 | 8p22 | POAG |
| ENSMMUG00000002235 | 12p23.2 | increased levels enhance retinal ganglion cell survival/reduce glaucoma loss (Ma et al., 2015) |
| ENSMMUG00000003748 | 4q34.3 | POAG |
| ENSMMUG00000000401 | 2p23.3 | POAG |
| ENSMMUG00000001336 | 5p13.1 | POAG |
| ENSMMUG00000004594 | 14q22.2 | glaucoma locus GLC3C |
| ENSMMUG00000000949 | 3q28-q29 | Low tension glaucoma |

This data demonstrates that the rodent and human postnatal ONLR contains nestin (+)/SOX2(+)/NG2(−) NPCs that give rise to oligodendrocyte progenitor cells (OPCs) and astrocytes. Self-replenishing neural-derived cells that are found within a dedicated vascular plexus give rise to culturable neurospheres, express multiple stem cell marker proteins, differentiate into multiple neural forms, and are age-depleted; these cells that fulfill the criteria of adult NPCs. ONLR-NPCs are distinct from the nestin (−)/NG2 (+)ON-OPCs, which are distinguished by their relative inability to generate neurospheres, grow poorly, and give rise mainly to oligodendrocytes. ONLR-NPCs resemble 'atypical astrocytes' previously reported to occur in the ONLR region (Wang et al., 2017). It is hypothesized that ONLR-NPCs likely perform multiple functions: during the early postnatal period, these cells enable focal myelination in the growing axons, enhancing directional polarization of axonal myelination and also generate astrocytes for the growing ON. ONLR-NPCs may provide a gliogenic processing center during ON growth, contributing to myelination and astrocyte production. In the mature ON, ONLR-NPCs enhance cellular replacement from stress-related loss and may also supply specific growth factors needed for normal axonal survival and function, similar to that seen in other CNS niches (Lu et al., 2003).

NG2(+) cells comprise 2-8% of the ON (Kang et al., 2010), yet the ON has reduced capacity for remyelination compared with spinal cord (SC) (Lachapelle et al., 2005). If ON remyelination capacity arises from the ONLR-NPC population, then effective repair can occur only in the anterior nerve, while SC-NPC remyelination can occur throughout the spinal cord.

The increased ratio of SOX2(+) nuclei to ONLR total nuclei in 2 m/o adult mice, vs the distal ON, is maintained through at least 7 PN months. Supporting these findings, the mouse ONLR formed neurospheres at a much higher frequency compared with distal ON tissue (graph, FIG. 2E). The ONLRs ability to form neurospheres was present in both young and adult animals. It is also present in ONLR from young human donors. The culture data confirms that that SOX2(+) cells in human and rodent ONLR-derived neurospheres co-express nestin(+). These data support the hypothesis that the SOX2(+)/nestin(+) cells present in the mammalian ONLR likely represent a replicating NPC population, endowing the ONLR with a greater response repertoire than that of the distal ON.

Many NG2(+) cells were generated during ONLR-NPC culture, suggesting a preference for NPC>OPC differentiation. Terminal differentiation of cells from ONLR cultures generated both astrocytes and oligodendrocytes, with few (<3%) NeuN (+) or Tuj1(+) cells. This is consistent with the ONLR-NPCs' hypothesized role in glial replenishment. This was confirmed by ON immunohistochemistry following induction of SOX2-GFP double mutants, which yields GFP (+)/NG2(−) cells in the ONLR, and GFP(+) cells with both astrocytic and oligodendroglial cell morphology in the anterior ON, whereas GFP(+) cells in the distal portion of same nerves exhibit only either NG2(+) or oligodendrocyte morphology. These results support the hypothesis that one role for ONLR-NPCs is to enable in vivo generation of mature glia.

Postnatal axonal growth can occur at specific stress points located at myelin: unmyelinated junctions (Goldberg, 2003). Since the region adjacent to the ONLR is where RGC axonal myelination begins, these results suggest that postnatal ON growth occurs by axonal extension from the unmyelinated retina, with myelination directly associated with emergence from the ONLR. ONLR-NPCs provide a source of oligodendrocytes and astrocytes during intensive postnatal ON growth. Without adequate ONLR-NPCs, axons either remain hypomyelinated or die. The data herein show both axonal loss and anterior hypomyelination following selective depletion of ONLR-NPCs following exposure to 4-OHT in SOX2-DTA reporter mice. In contrast, more distal axonal segments had a nearly normal myelination pattern.

In adults, overall oligodendrocyte generation declines, but the ONLR continues to have an increased Ki67(+) mitotic index, suggesting that the ONLR niche continues to contribute to adult glial cell replacement. It is hypothesized that ONLR-NPCs have distinct roles during early postnatal and adult stages: in the young, ONLR-NPCs contribute to ON growth, while in the adult they contribute to glial cell replacement.

Mouse ONLR-SOX2(+) nuclear numbers decline during aging, but remain relatively constant in the distal ON. An age-related decline in human ONLR-nestin expression is demonstrable (see FIG. 5i). These data indicate age-dependent ONLR-NPC loss. Human ONLR-NPCs are ultimately lost during aging, and this loss may alter the balance between degeneration, repair and the emergence of age-related ON diseases.

An important age-associated ON disease is open-angle glaucoma (OAG) (Lee et al., 2014), a progressive neuropathy associated with the ONLR. Progressive resistance to glaucoma treatment occurs in elderly individuals (Rossetti et al., 2010). ONLR-NPC depletion may contribute to OAG progression by reducing gliogenic support and associated neurotrophic factors such as brain-derived growth factor (BDNF), important for retinal ganglion cell (RGC) survival under stress, and which is secreted by cultured lamina-derived cells (Lambert et al., 2004). It is hypothesized that ONLR-NPCs present in younger individuals may protect against disease progression, and the age-related loss of ONLR-NPCs may contribute to disease progression via the inability to repair stress-related damage.

In summary, the ONLR in both humans and mice is not a non-proliferative barrier, but rather contains an NPC niche, which may have a role in both postnatal ON development and in adult ON support and repair. Age-related ONLR-NPC loss likely contributes to ON diseases such as OAG and understanding the roles of ONLR-NPCs enables new therapeutic strategies to treat ON disease.

While the invention has been described with reference to certain particular embodiments thereof, those skilled in the art will appreciate that various modifications may be made without departing from the spirit and scope of the invention. The scope of the appended claims is not to be limited to the specific embodiments described.

REFERENCES

All patents and publications mentioned in this specification are indicative of the level of skill of those skilled in the art to which the invention pertains. Each cited patent and publication is incorporated herein by reference in its entirety. All of the following references have been cited in this application:

Ahlenius, H., Visan, V., Kokaia, M., Lindvall, O., and Kokaia, Z. (2009). Neural stem and progenitor cells retain their potential for proliferation and differentiation into functional neurons despite lower number in aged brain. J Neurosci 29, 4408-4419.

Albrecht, M. C. (2008). Comparative anatomy of the optic nerve head and inner retina in non-primate animal models used for glaucoma research [In Process Citation]. Open Ophthalmol J 2, 94-101.

Almasieh, A., Wilson, A. S., Morquette, B., Cuega Vargas, J. L., and DiPolo, A. (2012). The molecular basis of retinal ganglion cell death in glaucoma. Progress in retinal and eye research 31, 152-181.

Anderson, D. R., and Hoyt, W. F. (1969). Ultrastructure of intraorbital portion of human and monkey optic nerve. Arch Ophthalmol 82, 506-530.

Badea, T. C., Wang, Y., and Nathans, J. (2003). A noninvasive genetic/pharmacologic strategy for visualizing cell morphology and clonal relationships in the mouse. J Neurosci 23, 2314-2322.

Balaratnasingam, C., Kang, M. H., Yu, P., Chan, G., Morgan, W. H., Cringle, S. J., and Yu, D. Y. (2014). Comparative quantitative study of astrocytes and capillary distribution in optic nerve laminar regions. Exp Eye Res 121, 11-22.

Cavazzin, C., Ferrari, D., Facchetti, F., Russignan, A., Vescovi, A. L., La Porta, C. A., and Gritti, A. (2006). Unique expression and localization of aquaporin-4 and aquaporin-9 in murine and human neural stem cells and in their glial progeny. Glia 53, 167-181.

Encinas, J. M., Michurina, T. V., Peunova, N., Park, J. H., Tordo, J., Peterson, D. A., Fishell, G., Koulakov, A., and Enikolopov, G. (2011). Division-coupled astrocytic differentiation and age-related depletion of neural stem cells in the adult hippocampus. Cell Stem Cell 8, 566-579.

Goldberg, J. L. (2003). How does an axon grow? Genes & Development 17, 941-958.

Gorris, R., Fischer, J., Erwes, K. L., Kesavan, J., Peterson, D. A., Alexander, M., Nothen, M. M., Peitz, M., Quandel, T., Karus, M., et al. (2015). Pluripotent stem cell-derived radial glia-like cells as stable intermediate for efficient generation of human oligodendrocytes. Glia 63, 2152-2167.

Kang, S. H., Fukaya, M., Yang, J. K., Rothstein, J. D., and Bergles, D. E. (2010). NG2+CNS Glial Progenitors Remain Committed to the Oligodendrocyte Lineage in Postnatal Life and following Neurodegeneration. Neuron 68, 668-681.

Lachapelle, F., Bachelin, C., Moissonnier, P., Nait-Oumesmar, B., Hidalgo, A., Fontaine, D., and Baron-Van Evercooren, A. (2005). Failure of remyelination in the non-human primate optic nerve. Brain Pathol 15, 198-207.

Lambert, W. S., Clark, A. F., and Wordinger, R. J. (2004). Neurotrophin and Trk expression by cells of the human lamina cribrosa following oxygen-glucose deprivation. BMC Neurosci 5, 51-51.

Lee, J. M., Caprioli, J., Nouri-Mahdavi, K., Afifi, A. A., Morales, E., Ramanathan, M., Yu, F., and Coleman, A. L. (2014). Baseline prognostic factors predict rapid visual field deterioration in glaucoma. Invest Ophthalmol Vis Sci 55, 2228-2236.

Levin, L. A. (2005). Pathophysiology of the progressive optic neuropathy of glaucoma. Ophthalmol Clin North Am 18, 355-335v.

Lojewski, X., Hermann, A., Wegner, F., Arauzo-Bravo, M. J., Hallmeyer-Elgner, S., Kirsch, M., Schwarz, J., Scholer, H. R., and Storch, A. (2014). Human adult white matter progenitor cells are multipotent neuroprogenitors similar to adult hippocampal progenitors. Stem Cells Transl Med 3, 458-469.

Lu, P., Jones, L. L., Snyder, E. Y., and Tuszynski, M. H. (2003). Neural stem cells constitutively secrete neurotrophic factors and promote extensive host axonal growth after spinal cord injury. Exp Neurol 181, 115-129.

Ma J, Guo C, Guo C, Sun Y, Liao T, Beattie U, et al. (2015) Transplantation of Human Neural Progenitor Cells Expressing IGF-1 Enhances Retinal Ganglion Cell Survival. PLOS ONE 10 (4): e0125695. https://doi.org/10.1371/journal.pone.0125695.

Malik, M. T., Healy, B. C., Benson, L. A., Kivisakk, P., Musallam, A., Weiner, H. L., and Chitnis, T. (2014). Factors associated with recovery from acute optic neuritis in patients with multiple sclerosis. Neurology 82, 2173-2179.

Nicholson, J. D., Puche, A. C., Guo, Y., Weinreich, D., Slater, B. J., and Bernstein, S. L. (2012). PGJ2 Provides Prolonged CNS Stroke Protection by Reducing White Matter Edema. PLOS One 7, e50021.

Park, D., Xiang, A. P., Mao, F. F., Zhang, L., Di, C. G., Liu, X. M., Shao, Y., Ma, B. F., Lee, J. H., Ha, K. S., et al.

(2010). Nestin Is Required for the Proper Self-Renewal of Neural Stem Cells. Stem Cells 28, 2162-2171.

Rossetti, L., Goni, F., Denis, P., Bengtsson, B., Martinez, A., and Heijl, A. (2010). Focusing on glaucoma progression and the clinical importance of progression rate measurement: a review. Eye (Lond) 24 Suppl 1, S1-S7.

Saito, M., Iwawaki, T., Taya, C., Yonekawa, H., Noda, M., Inui, Y., Mekada, E., Kimata, Y., Tsuru, A., and Kohno, K. (2001). Diphtheria toxin receptor-mediated conditional and targeted cell ablation in transgenic mice. Nat Biotech 19, 746-750.

Shen, Q., Wang, Y., Kokovay, E., Lin, G., Chuang, S. M., Goderie, S. K., Roysam, B., and Temple, S. (2008). Adult SVZ stem cells lie in a vascular niche: a quantitative analysis of niche cell-cell interactions. Cell Stem Cell 2008 Sep. 11; 3, 289-300.

Stoll, E. A., Habibi, B. A., Mikheev, A. M., Lasiene, J., Massey, S. C., Swanson, K. R., Rostomily, R. C., and Horner, P. J. (2011). Increased re-entry into cell cycle mitigates age-related neurogenic decline in the murine subventricular zone. Stem Cells 29, 2005-2017.

Tavazoie, M., Van der Veken, L., Silva-Vargas, V., Louissaint, M., Colonna, L., Zaidi, B., Garcia-Verdugo, J. M., and Doetsch, F. (2008). A specialized vascular niche for adult neural stem cells. Cell Stem Cell 3, 279-288.

Tiwari, S., Dharmarajan, S., Shivanna, M., Otteson, D. C., and Belecky-Adams, T. L. (2014). Histone deacetylase expression patterns in developing murine optic nerve [In Process Citation]. BMC Dev Biol 14, 1-18.

Wang, R., Seifert, P., and Jakobs, T. C. (2017). Astrocytes in the Optic Nerve Head of Glaucomatous Mice Display a Characteristic Reactive PhenotypeAstrocytes in the Optic Nerve Head of Glaucomatous Mice. Investigative Ophthalmology & Visual Science 58, 924-932.

What is claimed is:

1. A method of treating or preventing an optic nerve disease in a subject comprising administering to a subject in need thereof a therapeutically effective amount of a composition comprising one or more of:
   (i) a population of optic nerve lamina region-neural progenitor cells (ONLR-NPCs),
   (ii) ONLR-NPC conditioned media,
   (iii) an ONLR-NPC lysate, and
   thereby treating or preventing an optic nerve disease in the subject.

2. The method of claim 1, wherein the optic nerve disease is selected from the group consisting of open-angle glaucoma, angle-closure glaucoma, optic nerve hypoplasia, optic nerve hypomyelination, regional axonal dysfunction, non-arteritic anterior ischemic optic neuropathy (NAION), and optic neuritis.

3. The method of claim 1, wherein the composition is administered to the eye of the subject.

4. The method of claim 1, wherein the composition is administered to the subject via one or more of topical application, subconjunctival injection, intravitreal injection, and retrobulbar injection.

5. The method of claim 1, wherein the composition administered to the subject is a pharmaceutical formulation comprising a pharmaceutically acceptable carrier.

6. The method of claim 1, wherein the subject is a human.

7. The method of claim 1, wherein the ONLR-NPCs are nestin(+), SOX2(+), GFAP(+), NG2(−) cells.

8. The method of claim 1, wherein the ONLR-NPCs are nestin(+), SOX2(+), GFAP(+), NG2(−), SOX1(+), vimentin(+), BDNF(+) cells.

9. The method of claim 1, wherein the ONLR-NPCs express one or more of Latent Transforming Growth Factor-Beta 1 (TGF-β1), Connective Tissue Growth Factor (CTGF), Nerve Growth Factor (NGF), Fibroblast Growth Factor (FGF-1), Vascular Endothelial Growth Factor (VEGF), Mesenchymal Astrocyte Neurotrophic Factor (MANF) and Insulin-like Growth Factors-1 and -2 (IGF-1 and IGF-2).

10. The method of claim 1, wherein the ONLR-NPCs express at least five growth factors selected from the group consisting of VGF, TGFβ1, LTBP1, LTBP2, PDGFB, CTGF, FGF11, NDNF, PDGFC, TGFβ2, NGF, FGF1, Midkine, VEGFA, MANF, IGF-1, and IGF-2.

11. The method of claim 1, wherein the ONLR-NPCs express each of VGF, TGFβ1, LTBP1, LTBP2, PDGFB, CTGF, FGF11, NDNF, PDGFC, TGFβ2, NGF, FGF1, Midkine, VEGFA, MANF, IGF-1, and IGF-2.

12. The method of claim 1, wherein the ONLR-NPCs express one or more proteins selected from the group consisting of Cell Growth Regulator with Ring Finger Domain 1, Dynein Regulatory Complex Subunit 4, Fibroblast Growth Factor 12, Fibroblast Growth Factor 14, Fibroblast Growth Factor Receptor 4, Growth Arrest and DNA Damage-inducible Protein GADD45 beta, Growth Factor Independent 1 Transcriptional Repressor, Growth Hormone Receptor, Placental Growth Factor, Platelet-derived Growth Factor D/Spinal Cord-Derived Growth Factor B, Platelet-derived Growth Factor Receptor-like Protein, Transforming Growth Factor beta-1 Proprotein, Transforming Growth Factor beta-1-induced Transcript 1 Protein, Upper Zone of Growth Plate and Cartilage Matrix Associated Protein, Vascular Endothelial Growth Factor C and UNC-13 Homolog C.

13. The method of claim 1, wherein the ONLR-NPCs express each of Cell Growth Regulator with Ring Finger Domain 1, Dynein Regulatory Complex Subunit 4, Fibroblast Growth Factor 12, Fibroblast Growth Factor 14, Fibroblast Growth Factor Receptor 4, Growth Arrest and DNA Damage-inducible Protein GADD45 beta, Growth Factor Independent 1 Transcriptional Repressor, Growth Hormone Receptor, Placental Growth Factor, Platelet-derived Growth Factor D/Spinal Cord-Derived Growth Factor B, Platelet-derived Growth Factor Receptor-like Protein, Transforming Growth Factor beta-1 Proprotein, Transforming Growth Factor beta-1-induced Transcript 1 Protein, Upper Zone of Growth Plate and Cartilage Matrix Associated Protein, Vascular Endothelial Growth Factor C and UNC-13 Homolog C.

14. The method of claim 1, wherein the composition comprising one or more factors secreted by ONLR-NPCs comprises one or more of Latent Transforming Growth Factor-Beta 1 (TGF-β1), Connective Tissue Growth Factor (CTGF), Nerve Growth Factor (NGF), Fibroblast Growth Factor (FGF-1), Vascular Endothelial Growth Factor (VEGF), Mesenchymal Astrocyte Neurotrophic Factor (MANF) and Insulin-like Growth Factors-1 and -2 (IGF-1 and IGF-2).

15. The method of claim 1, wherein the composition comprising one or more factors secreted by ONLR-NPCs comprises each of Latent Transforming Growth Factor-Beta 1 (TGF-β1), Connective Tissue Growth Factor (CTGF), Nerve Growth Factor (NGF), Fibroblast Growth Factor (FGF-1), Vascular Endothelial Growth Factor (VEGF), Mesenchymal Astrocyte Neurotrophic Factor (MANF) and Insulin-like Growth Factors-1 and -2 (IGF-1 and IGF-2).

16. The method of claim 1, wherein the composition comprising one or more factors secreted by ONLR-NPCs comprises at least five of growth factors selected from the group consisting of VGF, TGFβ1, LTBP1, LTBP2, PDGFB, CTGF, FGF11, NDNF, PDGFC, TGFβ2, NGF, FGF1, Midkine, VEGFA, MANF, IGF-1, and IGF-2.

17. The method of claim 1, wherein the composition comprising one or more factors secreted by ONLR-NPCs comprises each of VGF, TGFβ1, LTBP1, LTBP2, PDGFB, CTGF, FGF11, NDNF, PDGFC, TGFβ2, NGF, FGF1, Midkine, VEGFA, MANF, IGF-1, and IGF-2.

* * * * *

SEQUENCE LISTING

```
<160> NUMBER OF SEQ ID NOS: 31

<210> SEQ ID NO 1
<211> LENGTH: 20
<212> TYPE: DNA
<213> ORGANISM: Artificial Sequence
<220> FEATURE:
<223> OTHER INFORMATION: chemically synthesized primer sequence

<400> SEQUENCE: 1
gaggcgctgg aacagagatt                                                   20

<210> SEQ ID NO 2
<211> LENGTH: 21
<212> TYPE: DNA
<213> ORGANISM: Artificial Sequence
<220> FEATURE:
<223> OTHER INFORMATION: chemically synthesized primer sequence

<400> SEQUENCE: 2
cacagccagc tggaactttt c                                                 21

<210> SEQ ID NO 3
<211> LENGTH: 21
<212> TYPE: DNA
<213> ORGANISM: Artificial Sequence
<220> FEATURE:
<223> OTHER INFORMATION: chemically synthesized primer sequence

<400> SEQUENCE: 3
ggcagtcata caaaagttgg c                                                 21

<210> SEQ ID NO 4
<211> LENGTH: 23
<212> TYPE: DNA
<213> ORGANISM: Artificial Sequence
<220> FEATURE:
<223> OTHER INFORMATION: chemically synthesized primer sequence

<400> SEQUENCE: 4
gtacagtatt tatcgtccgc aga                                               23

<210> SEQ ID NO 5
<211> LENGTH: 21
<212> TYPE: DNA
<213> ORGANISM: Artificial Sequence
<220> FEATURE:
<223> OTHER INFORMATION: chemically synthesized primer sequence
```

<400> SEQUENCE: 5
caggagttgt caaggcagag a                                              21

<210> SEQ ID NO 6
<211> LENGTH: 20
<212> TYPE: DNA
<213> ORGANISM: Artificial Sequence
<220> FEATURE:
<223> OTHER INFORMATION: chemically synthesized primer sequence

<400> SEQUENCE: 6
cttaagcctc gggctccaaa                                                20

<210> SEQ ID NO 7
<211> LENGTH: 20
<212> TYPE: DNA
<213> ORGANISM: Artificial Sequence
<220> FEATURE:
<223> OTHER INFORMATION: chemically synthesized primer sequence

<400> SEQUENCE: 7
gaccaacccc cgbggcgcac                                                20

<210> SEQ ID NO 8
<211> LENGTH: 20
<212> TYPE: DNA
<213> ORGANISM: Artificial Sequence
<220> FEATURE:
<223> OTHER INFORMATION: chemically synthesized primer sequence

<400> SEQUENCE: 8
tgggcccgaa tcattgtctg                                                20

<210> SEQ ID NO 9
<211> LENGTH: 20
<212> TYPE: DNA
<213> ORGANISM: Artificial Sequence
<220> FEATURE:
<223> OTHER INFORMATION: chemically synthesized primer sequence

<400> SEQUENCE: 9
gccttgttga tatcccgagt                                                20

<210> SEQ ID NO 10
<211> LENGTH: 21
<212> TYPE: DNA
<213> ORGANISM: Artificial Sequence
<220> FEATURE:
<223> OTHER INFORMATION: chemically synthesized primer sequence

<400> SEQUENCE: 10
gcccatcatg atcatctctc g                                              21

<210> SEQ ID NO 11
<211> LENGTH: 20
<212> TYPE: DNA
<213> ORGANISM: Artificial Sequence
<220> FEATURE:
<223> OTHER INFORMATION: chemically synthesized primer sequence

<400> SEQUENCE: 11
tgtgtaagca gagctcatgc                                                20

<210> SEQ ID NO 12

<211> LENGTH: 18
<212> TYPE: DNA
<213> ORGANISM: Artificial Sequence
<220> FEATURE:
<223> OTHER INFORMATION: chemically synthesized primer sequence

<400> SEQUENCE: 12
catagggtct cggggtct                                                      18

<210> SEQ ID NO 13
<211> LENGTH: 20
<212> TYPE: DNA
<213> ORGANISM: Artificial Sequence
<220> FEATURE:
<223> OTHER INFORMATION: chemically synthesized primer sequence

<400> SEQUENCE: 13
tgagagggat agctgtgagc                                                    20

<210> SEQ ID NO 14
<211> LENGTH: 19
<212> TYPE: DNA
<213> ORGANISM: Artificial Sequence
<220> FEATURE:
<223> OTHER INFORMATION: chemically synthesized primer sequence

<400> SEQUENCE: 14
gttccaagcc acgacctac                                                     19

<210> SEQ ID NO 15
<211> LENGTH: 20
<212> TYPE: DNA
<213> ORGANISM: Artificial Sequence
<220> FEATURE:
<223> OTHER INFORMATION: chemically synthesized primer sequence

<400> SEQUENCE: 15
cacgtacagt gctttgccac                                                    20

<210> SEQ ID NO 16
<211> LENGTH: 20
<212> TYPE: DNA
<213> ORGANISM: Artificial Sequence
<220> FEATURE:
<223> OTHER INFORMATION: chemically synthesized primer sequence

<400> SEQUENCE: 16
aactccgccc attcactgac                                                    20

<210> SEQ ID NO 17
<211> LENGTH: 21
<212> TYPE: DNA
<213> ORGANISM: Artificial Sequence
<220> FEATURE:
<223> OTHER INFORMATION: chemically synthesized primer sequence

<400> SEQUENCE: 17
cgtaagtcct tcaccagctt g                                                  21

<210> SEQ ID NO 18
<211> LENGTH: 21
<212> TYPE: DNA
<213> ORGANISM: Artificial Sequence
<220> FEATURE:
<223> OTHER INFORMATION: chemically synthesized primer sequence

<400> SEQUENCE: 18

```
gaatccaaag ctcacatcca c                                              21

<210> SEQ ID NO 19
<211> LENGTH: 20
<212> TYPE: DNA
<213> ORGANISM: Artificial Sequence
<220> FEATURE:
<223> OTHER INFORMATION: chemically synthesized primer sequence

<400> SEQUENCE: 19
gagacttcac caggggagat                                                20

<210> SEQ ID NO 20
<211> LENGTH: 21
<212> TYPE: DNA
<213> ORGANISM: Artificial Sequence
<220> FEATURE:
<223> OTHER INFORMATION: chemically synthesized primer sequence

<400> SEQUENCE: 20
aaaaccacat gcttgccatc c                                              21

<210> SEQ ID NO 21
<211> LENGTH: 21
<212> TYPE: DNA
<213> ORGANISM: Artificial Sequence
<220> FEATURE:
<223> OTHER INFORMATION: chemically synthesized primer sequence

<400> SEQUENCE: 21
cagcaaggac actgagcaag a                                              21

<210> SEQ ID NO 22
<211> LENGTH: 21
<212> TYPE: DNA
<213> ORGANISM: Artificial Sequence
<220> FEATURE:
<223> OTHER INFORMATION: chemically synthesized primer sequence

<400> SEQUENCE: 22
gcccctcctg ttattatggg g                                              21

<210> SEQ ID NO 23
<211> LENGTH: 22
<212> TYPE: DNA
<213> ORGANISM: Artificial Sequence
<220> FEATURE:
<223> OTHER INFORMATION: chemically synthesized primer sequence

<400> SEQUENCE: 23
gcggtctggc agtaaaacta tc                                             22

<210> SEQ ID NO 24
<211> LENGTH: 23
<212> TYPE: DNA
<213> ORGANISM: Artificial Sequence
<220> FEATURE:
<223> OTHER INFORMATION: chemically synthesized primer sequence

<400> SEQUENCE: 24
gtgaaacagc attgctgtca ctt                                            23

<210> SEQ ID NO 25
<211> LENGTH: 17
<212> TYPE: DNA
```

<213> ORGANISM: Artificial Sequence
<220> FEATURE:
<223> OTHER INFORMATION: chemically synthesized primer sequence

<400> SEQUENCE: 25
cgacctgcag gtcctcg                                                17

<210> SEQ ID NO 26
<211> LENGTH: 24
<212> TYPE: DNA
<213> ORGANISM: Artificial Sequence
<220> FEATURE:
<223> OTHER INFORMATION: chemically synthesized primer sequence

<400> SEQUENCE: 26
ctcgagtttg tccaattatg tcac                                        24

<210> SEQ ID NO 27
<211> LENGTH: 24
<212> TYPE: DNA
<213> ORGANISM: Artificial Sequence
<220> FEATURE:
<223> OTHER INFORMATION: chemically synthesized primer sequence

<400> SEQUENCE: 27
ccaaagtcgc tctgagttgt tatc                                        24

<210> SEQ ID NO 28
<211> LENGTH: 20
<212> TYPE: DNA
<213> ORGANISM: Artificial Sequence
<220> FEATURE:
<223> OTHER INFORMATION: chemically synthesized primer sequence

<400> SEQUENCE: 28
gagcgggaga aatggatatg                                             20

<210> SEQ ID NO 29
<211> LENGTH: 21
<212> TYPE: DNA
<213> ORGANISM: Artificial Sequence
<220> FEATURE:
<223> OTHER INFORMATION: chemically synthesized primer sequence

<400> SEQUENCE: 29
ctctgctgcc tcctggcttc t                                           21

<210> SEQ ID NO 30
<211> LENGTH: 19
<212> TYPE: DNA
<213> ORGANISM: Artificial Sequence
<220> FEATURE:
<223> OTHER INFORMATION: chemically synthesized primer sequence

<400> SEQUENCE: 30
tcaatgggcg ggggtcgtt                                              19

<210> SEQ ID NO 31
<211> LENGTH: 21
<212> TYPE: DNA
<213> ORGANISM: Artificial Sequence
<220> FEATURE:
<223> OTHER INFORMATION: chemically synthesized primer sequence

```
<400> SEQUENCE: 31
cgaggcggat cacaagcaat a                                                      21
```